(12) United States Patent
Robinson et al.

(10) Patent No.: US 7,521,551 B2
(45) Date of Patent: Apr. 21, 2009

(54) CHLORINS POSSESSING FUSED RING SYSTEMS USEFUL AS PHOTOSELECTIVE COMPOUNDS FOR PHOTODYNAMIC THERAPY

(75) Inventors: Byron C. Robinson, Santa Barbara, CA (US); Dipanjan Sengupta, Goleta, CA (US); Avinash Phadke, Goleta, CA (US)

(73) Assignee: Miravant Pharmaceuticals, Inc., Santa Barbara, CA (US)

( * ) Notice: Subject to any disclaimer, the term of this patent is extended or adjusted under 35 U.S.C. 154(b) by 601 days.

(21) Appl. No.: 10/922,974

(22) Filed: Aug. 23, 2004

(65) Prior Publication Data
US 2005/0020560 A1  Jan. 27, 2005

Related U.S. Application Data

(62) Division of application No. 09/538,980, filed on Mar. 30, 2000, now Pat. No. 6,794,505.

(51) Int. Cl.
C07B 47/00 (2006.01)
(52) U.S. Cl. .................. 540/145; 540/121; 534/15; 534/16
(58) Field of Classification Search ........... 540/145, 540/121; 534/15, 16
See application file for complete search history.

(56) References Cited

U.S. PATENT DOCUMENTS

| 4,649,151 A | 3/1987 | Dougherty et al. | 514/410 |
|---|---|---|---|
| 5,171,749 A | 12/1992 | Levy et al. | 514/410 |
| 5,198,460 A | 3/1993 | Pandey et al. | 514/410 |
| 5,225,433 A | 7/1993 | Dougherty et al. | 514/410 |
| 5,399,583 A | 3/1995 | Levy et al. | 514/410 |
| 5,459,159 A | 10/1995 | Pandey et al. | 514/410 |
| 5,489,590 A | 2/1996 | Gulliya et al. | 514/224.8 |
| 6,794,505 B1 * | 9/2004 | Robinson et al. | 540/145 |

FOREIGN PATENT DOCUMENTS

CA  2221912  11/1997

OTHER PUBLICATIONS

Amould, J.C., et al., "New Applications of the Mitsunobu Reaction in the Synthesis of C-2 N-Methyl Carbapenems," *Tetrahedron Letters*, 33(47): 7133-7136 (1992).
Barloy, Laurent et al., "Anomalous Double Cyclization Reactions of beta-Formylporphyrins," J. Org. Chem. (1994) 59(26), 7976-85.

(Continued)

*Primary Examiner*—James O. Wilson
*Assistant Examiner*—Paul V. Ward
(74) *Attorney, Agent, or Firm*—Finnegan, Henderson, Farabow, Garrett & Dunner LLP

(57) ABSTRACT

The present invention provides a process of preparation of naphthochlorins and other chlorins with annelated ring systems useful for photodynamic therapy and the compounds themselves. The method for producing naphthochlorin compounds include contacting compounds such as meso-(2'-hydroxymethyl)phenyl porphyrin or meso-(2'-N,N,N-trialkylaminomethyl)phenyl porphyrin precursors with at least one acid catalyst at sufficient temperature for a sufficient time to yield the desired conversion. In a similar manner chlorins possessing annelated ring systems may be made from compounds such as meso-(2'-hydroxymethyl)aryl porphyrins or meso-(2'-N,N,N-trialkylaminomethyl)phenyl porphyrin. The procedures described herein provide new routes for synthesizing naphthochlorins and chlorins with annelated ring systems.

6 Claims, 2 Drawing Sheets

OTHER PUBLICATIONS

Dolphin, "The Porphyrins," table of contents, pp. 235-264, 341-387, Academic Press, vol. 1, Structure and Synthesis, Part A, New York, (1978).

Dubowchik, G.M., et al., "Controlled Conformational Changes in Covalently-linked Dimeric Porhyrins," *J. Chem. Soc., Chem. Commun.*, 13:904-906 (1985).

Faustino et al., "New Naphthochlorins from the Intramolecular Cyclization of β-Vinyl-meso-Tetraarylporphyrins," *Tetrahedron Letters*, vol. 36:33, pp. 5977-5978 (1995).

Green, Eds, et al., "Protective Groups in Organic Synthesis," 2nd, table of contents, John Wiley & sons, Inc., New York, (1991).

Gunter M.J., et al., "Synthesis and Atropisomer Separation of Porphyrins Containing Functionalization at the 5, 15-Meso Positions: Application to the Synthesis of Binuclear Ligand Systems," *J. Org. Chem.*, 46:4792-4795 (1981).

Harris D., et al., "A Convenient Synthesis of meso-Substituted Porphyrins," *Bioorganic Chemistry*, 9:63-70 (1980).

Ishkov, Yu. V. et al., "Porphyrins and their derivatives. XVII. Intramolecular cyclization of 2-formyl-5, 10, 15, 20-tetraphenylporphyrin complexes," ZH, ORG. KHIM. (1995), 31(1), 136-9.

Krattinger B., et al., "Novel Synthesis and New Chemistry of Naphthochlorins," *Chem. Comm.* (7) pp. 757-758 (1998).

Lash, T.D., et al., "Synthesis of Novel Porphyrin Chromophores from Nitroarenes: Further Applications of the Barton-Zard Pyrrole Condensation," *Tetrahedron Letters*, 38(12): 2031-2034 (1997).

Leznoff, et al. Eds., "Phthalocyanines Properties and Applications," VCH Publishers, Inc., vol. 1-4, table of contents, North York, Ontario, Canada, (1989).

Meier H., et al., "Synthesis and Chromophoric Interactions of an 'ortho-Gable-porphyrin.' A Novel Tetraphenylporphyrin Dimer," *J. Chem. Soc. Commun.*, 13:923-924 (1989).

Moser, et al., "The Phthalocyanines," table of contents, CRC Press, Inc., vol. II, *Manufacture and Applications*, Boca Raton, Florida, (1983).

Moser, et al., "The Phthalocyanines," table of contents, CRC Press, Inc., vol. I, *Properties*, Boca Raton, Florida, (1983).

Osuka, A., et al., "Synthesis of Strapped, Dimeric, and Trimeric Porphyrins Based on Intramolecular Marcocyclization Reactions," *The Chemical Society of Japan*, 64: 1213-1225 (1991).

Pandey, R.K., et al., "Synthesis, Stability, and Tumorcidal Activity of Porphyrin Dimers and Trimers with Ether Linkages," *Tetrahedron Letters*, 31(51): 7399-7402 (1990).

Sessler, J.L. et al., "The Synthesis and Optical Properties of the First Quinone-Linked Porphyrin Dimer," *Tetrahedron Letters*, 28(52): 6569-6572 (1987).

Shinoda, S. et al: "Energy and Electron Transfer Properties of Methyl Pheophorbide-a in Zinc Porphyrin-Pheophorbide Dyads," Tetrahedron, Elsevier Science Publishers, Amsterdam, NL. vol. 53, No. 40, Oct. 6, 1997, pp. 13657-13666.

Smith Ed., "Porphyrins and Metalloporphyrins," table of contents, pp. 29-55, 729-732, Elsevier Scientific Publishing Company, Amsterdam, (1975).

Tse, Y-H, et al., "Electrochemistry and Spectroelectrochemistry of Substituted tetrabenzotriazaporphine," *Canadian Journal of Chemistry*, 71(5): 742-753 (1993).

Zhang, Xiao-Xiang et al., "Synthesis and Triiron Complexes of PDK, a New Porphyrin-Linked Dicarboxylate Ligand," J. Am. Chem. Soc. (1998), 120(39), 10260-10261.

Zhilin, Z. I. et al., "A new product of intramolecular cyclization of the copper 2-formyl-5, 10, 15, 20-tetraphenylporphyrin complex," DOPOV. NATS. AKAD. NAUK UKR. (2000), (4), 147-150.

Loudon, *Organic Chemistry*, Fouth Edition, pp. 111, 121, 607, 678-682, 696, 913 and 938, (2002).

\* cited by examiner

CHLORINS POSSESSING FUSED RING SYSTEMS USEFUL AS PHOTOSELECTIVE COMPOUNDS FOR PHOTODYNAMIC THERAPY

This is a divisional of application Ser. No. 09/538,980, filed Mar. 30, 2000, now U.S. Pat. No. 6,794,505 the disclosure of which is hereby incorporated herein by reference.

FIELD OF THE INVENTION

The present invention relates to compounds useful as photoselective agents in photodynamic therapy and procedures for synthesizing such compounds.

BACKGROUND OF THE INVENTION

Photodynamic therapy is a procedure that uses photoselective (light-activated) drugs to target and destroy diseased cells. Photoselective drugs transform light energy into chemical energy in a manner similar to the action of chlorophyll in green plants. The photoselective drugs are inactive until switched on by light of a specific wavelength thereby enabling physicians to target specific groups of cells and control the timing and selectivity of treatment. The result of this process is that diseased cells are destroyed with minimal damage to surrounding normal tissues.

Photodynamic therapy begins with the administration, to a patient, of a preferred amount of a photoselective compound which is selectively taken up and/or retained by the biologic target, i.e., tissue or cells. After the photoselective compound is taken up by the target, a light of the appropriate wavelength to be absorbed by the photoselective compound is delivered to the targeted area. This activating light excites the photoselective compound to a higher energy state. The extra energy of the excited photoselective compound can then be used to generate a biological response in the target area by interaction with oxygen. As a result of the irradiation, the photoselective compound exhibits cytotoxic activity, i.e., it destroys cells. Additionally, by localizing in the irradiated area, it is possible to contain the cytotoxicity to a specific target area. For a more detailed description of photodynamic therapy, see U.S. Pat. Nos. 5,225,433; 5,198,460; 5,171,749; 4,649,151; 5,399,583; 5,459,159; and 5,489,590, the disclosures of which are incorporated herein by reference.

One important factor in the effectiveness of photodynamic therapy for some disease indications is the depth of tissue penetration by the activating light. It would therefore be desirable to find photoselective compounds that absorb at wavelengths in which light penetration through the tissue is deep. Thus, there is a need for photoselective compounds, useful for photodynamic therapy, that possess wavelength absorptions between about 300 and about 850 nm, the latter being a region where light penetration through tissues is optimal.

A large number of naturally occurring and synthetic dyes are currently being evaluated as potential photoselective compounds in the field of photodynamic therapy. Perhaps the most widely studied class of photoselective dyes in this field are the tetrapyrrolic macrocyclic compounds generally called porphyrins.

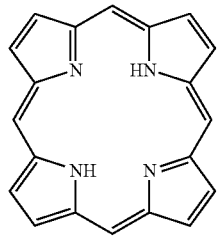

Porphyrin

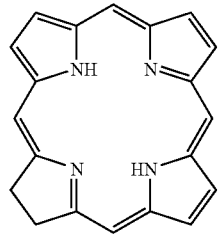

Chlorin

In general, porphyrins typically have low energy absorptions, called band I absorption at ~620-650 nm, with molar extinction coefficients in the order of 100-10,000 $M^{-1}$ $cm^{-1}$. Because of this fact, porphyrins have largely been criticized as having less than optimal wavelength and light absorption properties for use in photodynamic therapy.

Chlorins are compounds that differ from porphyrins in that one of the pyrrole rings has been reduced, either by addition of hydrogen or by carbon bond formation.

Regioselective reduction of porphyrins by hydrogen produces chlorins, examples of which are shown below. Unlike porphyrins, chlorins have strong band I absorptions typically in the range of 30,000-80,000 $M^{-1}$ $cm^{-1}$, and have therefore received much interest in the field of photodynamic therapy. In the compounds shown below, $R_1$ and $R_2$ are independently selected from functional groups having a molecular weight less than about 100,000 daltons.

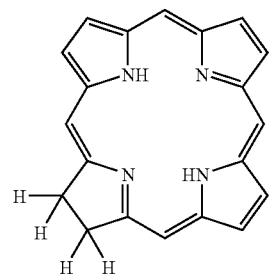

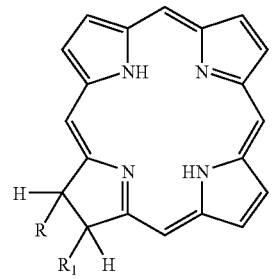

Unfortunately, oxygen is known to oxidize these types of chlorins back to porphyrins, with loss of the valuable high molar extinction coefficients of the longer wavelength band I absorption. For this reason, as well as producing stable pharmaceuticals, several groups have produced chlorins that are produced from porphyrins, via annelation of cyclic ring systems to the reduced pyrrole. Examples of these chlorin types are shown below. In the compounds shown below, R, $R_1$, $R_2$, and $R_3$ are independently selected from functional groups having a molecular weight less than about 100,000 daltons.

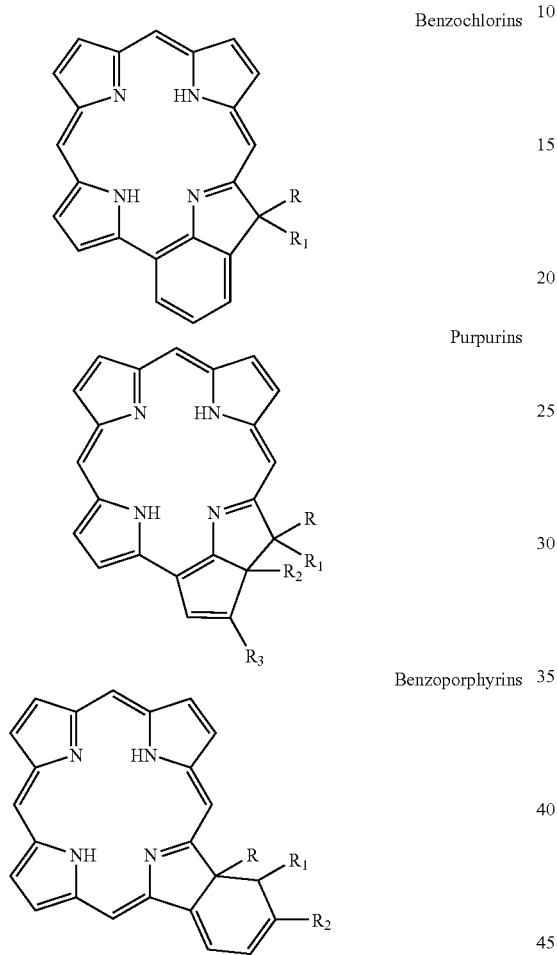

Fusion of the exocyclic rings has the potential advantage of limiting oxidation of the prepared chlorin. In addition and just as importantly, such compounds generally have improved light absorption profiles with longer wavelength absorptions and higher molar extinction coefficients than porphyrins.

Further, it would be advantageous to derivatize or extend the exocyclic rings of such compounds in order to influence the light absorption profiles of these compounds. By influencing the light absorption properties of these compounds it may be possible to generate molecules that absorb light at a wavelength where light penetration through tissues is optimal for specific disease indications. Further functionalization of such molecules will alter biological properties such as solubility and physiological clearance. For instance, increasing the amphilicity or lipophilicity of the molecules enhances the interaction with polar and nonpolar environments. Therefore, there is great interest in developing stable chlorins with improved light absorption profiles that can be used in the field of photodynamic therapy.

SUMMARY OF THE INVENTION

To achieve the advantages and in accordance with the purpose of the invention, as embodied and broadly described herein, the compounds of formulae I, II, III, IV, and V are provided:

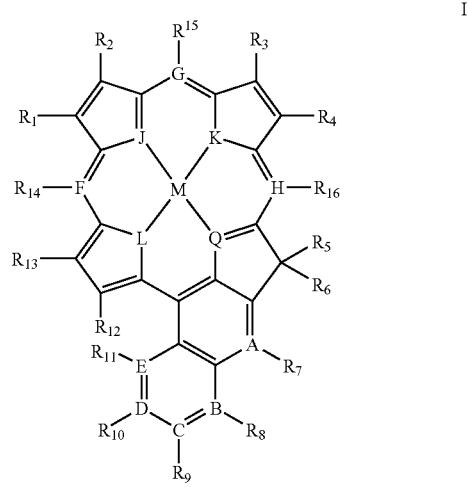

I

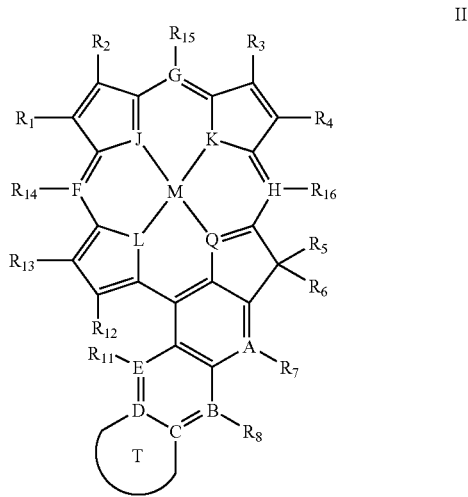

II

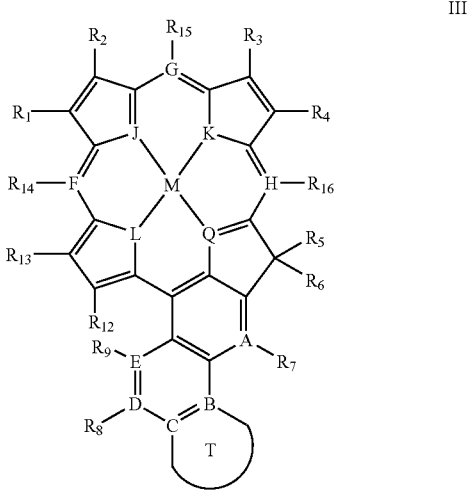

III

-continued

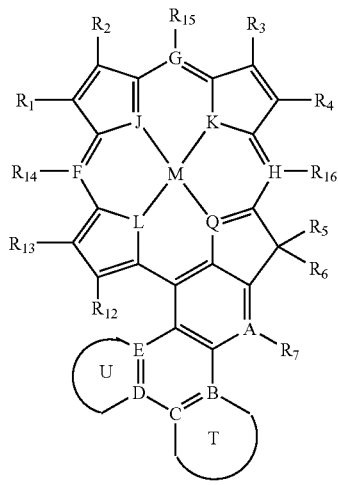

IV

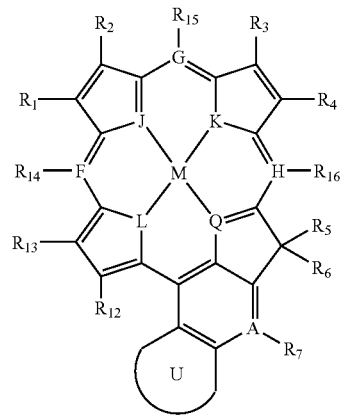

V

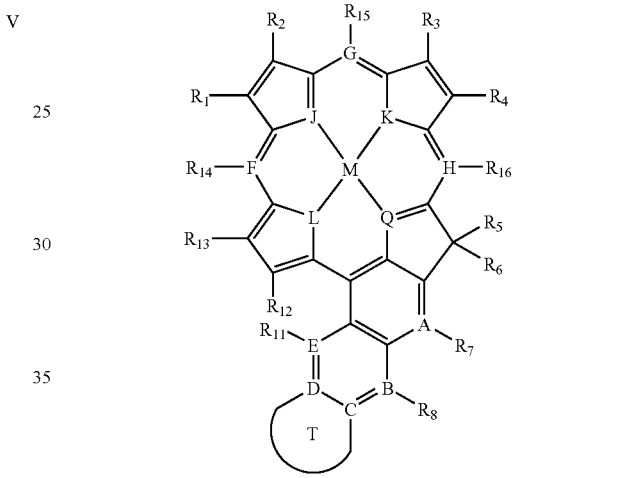

II wherein in formula I:

$R_1$, $R_2$, $R_3$, $R_4$, $R_5$, $R_6$, $R_{12}$, $R_{13}$, $R_{14}$, $R_{15}$, and $R_{16}$ are independently selected from hydrogen, a halogen; unsubstituted or substituted alkyl containing 0 or more carbon atoms, $C_3$-$C_6$ cycloalkyl, acetyl, aryl, alkenyl, alkynyl, amide groups, or ester groups; $NR_{17}R_{18}$; vinyl; $N(R_{17})(R_{18})(R_{19})^+ Z^-$; $CH=CHNR_{17}R_{18}$; $CH_2CH_2NR_{17}R_{18}$; $CH=CHN(R_{17})(R_{18})(R_{19})^+ Z^-$; $CH_2CH_2N(R_{17})(R_{18})(R_{19})^+ Z^-$; $CHOHCH_3$; $CHOR_{17}CH_3$; CN; OH; $OR_{17}$; CHO; $CH=CHCO_2R_{17}$; $(CH_2)_nOH$; $(CH_2)_nSH$; $(CH_2)_n$O-alkoxy; $(CH_2)_nSR_{17}$; $(CH_2)_nOR_{17}$; $(CH_2)_nCO_2R_{17}$; $(CH_2)_nCONHR_{17}$; $(CH_2)_nCON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+ Z^-$;

$R_{15}$ may be additionally selected from a cycloalkyl, aromatic, or hetereoaromatic fused ring system;

$R_{17}$, $R_{18}$, and $R_{19}$ are independently selected from hydrogen, a physiologically acceptable ion; unsubstituted or substituted $C_1$-$C_6$ alkyl, aryl, alkenyl, or alkynyl; and a functional group having a molecular weight less than about 100,000 daltons;

$Z^-$ is a charge balancing ion;

$R_7$, $R_8$, $R_9$, $R_{10}$, and $R_{11}$ are independently selected from hydrogen, an unsubstituted or substituted alkyl containing 0 or more carbon atoms and aryl;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr; and A, B, C, D, E, F, G, H, J, K, L, and Q are independently selected from carbon, nitrogen, sulfur, oxygen, $N^+(R_{20}) Z'^-$, $Se^+$, and $Te^+$; where $R_{20}$ is a functional group having a molecular weight of less than about 100,000 daltons and $Z'$ is a charge balancing ion;

provided that when $R_1$, $R_2$, $R_3$, $R_4$, $R_5$, $R_6$, $R_8$, $R_{10}$, $R_{11}$, $R_{12}$, and $R_{13}$ are hydrogen, and $R_9$ is selected from the group consisting of hydrogen and $OCH_3$, and J, K, L, and Q are nitrogen, and A, B, C, D, E, F, G, and H are carbon, and M is Ni, and $R_7$ is selected from the group consisting of $CH_3$, $CO_2^tBu$, $CO_2Et$, $CO_2^iPr$, and $CO_2Bu$, then $R_{14}$, $R_{15}$, and $R_{16}$ cannot simultaneously be $C_6H_4X$ where X is selected from the group consisting of hydrogen and $OCH_3$.

In formula II:

$R_1$, $R_2$, $R_3$, $R_4$, $R_5$, $R_6$, $R_7$, $R_8$, $R_{11}$, $R_{12}$, $R_{13}$, $R_{14}$, $R_{15}$, and $R_{16}$ are independently selected from hydrogen; halogen; unsubstituted or substituted alkyl acetyl containing 0 or more carbon atoms, $C_3$-$C_6$ cycloalkyl, acetyl, aryl, alkenyl, alkynyl, amide groups, or ester groups; $NR_{17}R_{18}$; vinyl; $N(R_{17})(R_{18})(R_{19})^+ Z^-$; $CH=CHNR_{17}R_{18}$; $CH_2CH_2NR_{17}R_{18}$; $CH=CHN(R_{17})(R_{18})(R_{19})^+ Z^-$; $CH_2CH_2N(R_{17})(R_{18})(R_{19})^+ Z^-$; $CHOHCH_3$; $CHOR_{17}CH_3$; CN; OH; $OR_{17}$; CHO; $CH=CHCO_2R_{17}$; $(CH_2)_nOH$; $(CH_2)_nSH$; $(CH_2)_n$O-alkoxy; $(CH_2)_nSR_{17}$; $(CH_2)_nOR_{17}$; $(CH_2)_nCO_2R_{17}$; $(CH_2)_nCONHR_{17}$; $(CH_2)_nCON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+ Z^-$;

$R_{17}$, $R_{18}$, and $R_{19}$ are independently selected from hydrogen; a physiologically acceptable ion; unsubstituted or substituted $C_1$-$C_6$ alkyl, aryl, alkenyl, or alkynyl; and a functional group having a molecular weight less than about 100,000 daltons;

$Z^-$ is a charge balancing ion;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr;

A, B, C, D, E, F, G, H, L, J, K, Q are independently selected from carbon, nitrogen, $N^+(R_{20}) Z'^-$, O, $Se^+$, and $Te^+$; where $R_{20}$ is a functional group having a molecular weight of less than about 100,000 daltons and $Z'^-$ is a charge balancing ion; and T is selected from a substituted or unsubstituted aromatic, heteroaromatic, polyaromatic, polyheteroaromatic, cycloalkyl, and a heterocycloalkyl group.

In formula III:

$R_1, R_2, R_3, R_4, R_5, R_6, R_7, R_8, R_9, R_{12}, R_{13}, R_{14}, R_{15}$, and $R_{16}$ are independently selected from hydrogen; halogen; unsubstituted or substituted alkyl, $C_3$-$C_6$ cycloalkyl, acetyl, aryl, alkenyl, alkynyl, amide groups, or ester groups; $NR_{17}R_{18}$; vinyl; $N(R_{17})(R_{18})(R_{19})^+Z^-$; $CH=CHNR_{17}R_{18}$; $CH_2CH_2NR_{17}R_{18}$; $CH=CHN(R_{17})(R_{18})(R_{19})^+Z^-$; $CH_2CH_2N(R_{17})(R_{18})(R_{19})^+Z^-$; $CHOHCH_3$; $CHOR_{17}CH_3$; $CN$; $OH$; $OR_{17}$; $CHO$; $CH=CHCO_2R_{17}$; $(CH_2)_nOH$; $(CH_2)_nSH$; $(CH_2)_nO$-alkoxy; $(CH_2)_nSR_{17}$; $(CH_2)_nOR_{17}$; $(CH_2)_nCO_2R_{17}$; $(CH_2)_nCONHR_{17}$; $(CH_2)_nCON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+Z^-$;

$R_{17}, R_{18}$, and $R_{19}$ are independently selected from hydrogen; a physiologically acceptable ion; unsubstituted or substituted $C_1$-$C_6$ alkyl, aryl, alkenyl or alkynyl; and a functional group having a molecular weight less than about 100,000 daltons;

$Z^-$ is a charge balancing ion;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr;

A, B, C, D, E, F, G, H, L, J, K, and Q are independently selected from carbon, nitrogen, $N^+(R_{20})Z'^-$, oxygen, $Se^+$, and $Te^+$;

$Z'^-$ is a charge balancing ion;

$R_{20}$ is a functional group having a molecular weight of less than about 100,000 daltons; and T is selected from a substituted and unsubstituted aromatic, heteroaromatic, polyaromatic, polyheteroaromatic cycloalkyl, and a heterocycloalkyl group.

In formula IV:

$R_1, R_2, R_3, R_4, R_5, R_6, R_7, R_{12}, R_{13}, R_{14}, R_{15}$, and $R_{16}$ are independently selected from hydrogen; halogen; unsubstituted or substituted alkyl containing 0 or more carbon atoms, $C_3$-$C_6$ cycloalkyl, acetyl, aryl, alkenyl, alkynyl, amides; or ester groups; $NR_{17}R_{18}$; vinyl; $N(R_{17})(R_{18})(R_{19})^+Z^-$; $CH=CHNR_{17}R_{18}$; $CH_2CH_2NR_{17}R_{18}$; $CH=CHN(R_{17})(R_{18})(R_{19})^+Z^-$; $CH_2CH_2N(R_{17})(R_{18})(R_{19})^+Z^-$; $CHOHCH_3$; $CHOR_{17}CH_3$; $CN$; $OH$; $OR_{17}$; $CHO$; $CH=CHCO_2R_{17}$; $(CH_2)_nOH$; $(CH_2)_nSH$; $(CH_2)_nO$-alkoxy; $(CH_2)_nSR_{17}$; $(CH_2)_nOR_{17}$; $(CH_2)_nCO_2R_{17}$; $(CH_2)_nCONHR_{17}$; $(CH_2)_nCON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+Z^-$;

$R_{17}, R_{18}$, and $R_{19}$ are independently selected from hydrogen, a physiologically acceptable ion; and unsubstituted or substituted $C_1$-$C_6$ alkyl, aryl, alkenyl or alkynyl;

$Z^-$ is a charge balancing ion;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr;

A, B, C, D, E, F, G, H, L, K, and Q are independently selected from carbon, nitrogen, $N^+(R_{20})Z'^-$, oxygen, $Se^+$, and $Te^+$;

$R_{20}$ is selected from alkyl and aryl;

$Z'^-$ is a charge balancing ion; and

U and T are independently selected from a substituted or unsubstituted aromatic, heteroaromatic, polyaromatic, polyheteroaromatic, cycloalkyl, and a heterocycloalkyl group.

In formula V:

$R_1, R_2, R_3, R_4, R_5, R_6, R_7, R_{12}, R_{13}, R_{14}, R_{15}$, and $R_{16}$ are independently selected from hydrogen; halogen; unsubstituted or substituted alkyl containing 0 or more carbon atoms, $C_3$-$C_6$ cycloalkyl, acetyl, aryl, alkenyl, alkynyl, amide groups, or ester groups; $NR_{17}R_{18}$; vinyl; $N(R_{17})(R_{18})(R_{19})^+Z^-$; $CH=CHNR_{17}R_{18}$; $CH_2CH_2NR_{17}R_{18}$; $CH=CHN(R_{17})(R_{18})(R_{19})^+Z^-$; $CH_2CH_2N(R_{17})(R_{18})(R_{19})^+Z^-$; $CHOHCH_3$; $CHOR_{17}CH_3$; $CN$; $OH$; $OR_{17}$; $CHO$; $CH=CHCO_2R_{17}$; $(CH_2)_nOH$; $(CH_2)_nSH$; $(CH_2)_nO$-alkoxy; $(CH_2)_nSR_{17}$; $(CH_2)_nOR_{17}$; $(CH_2)_nCO_2R_{17}$; $(CH_2)_nCONHR_{17}$; $(CH_2)_nCON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+Z^-$;

$R_{17}, R_{18}$, and $R_{19}$ are independently selected from hydrogen; a physiologically acceptable ion; unsubstituted or substituted $C_1$-$C_6$ alkyl, aryl, alkenyl or alkynyl; and a functional group having a molecular weight less than about 100,000 daltons; $Z^-$ is a charge balancing ion;

n is an integer ranging from 1 to 4;

A, F, G, H, L, K, Q are independently selected from carbon, nitrogen, $N^+(R_{20})Z'^-$, oxygen, $Se^+$, and $Te^+$; $R_{20}$ is selected from alkyl or aryl; $Z'^-$ is a charge balancing ion;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr; and U is selected from a substituted or unsubstituted aromatic, heteroaromatic, polyaromatic, polyheteroaromatic, cycloalkyl, and a heterocycloalkyl group.

Also provided are processes for producing the compounds of formulae I, II, III, IV, V, and VI comprising contacting compounds such as the corresponding meso-(2'-hydroxymethyl)aromatic or heteroaromatic porphyrin or meso-(2'-N,N,N-trialkylaminomethyl)aromatic or heteroaromatic porphyrin precursor with at least one acid catalyst for a sufficient time and at a sufficient temperature to form the compounds of formulae I, II, III, IV, V, and VI:

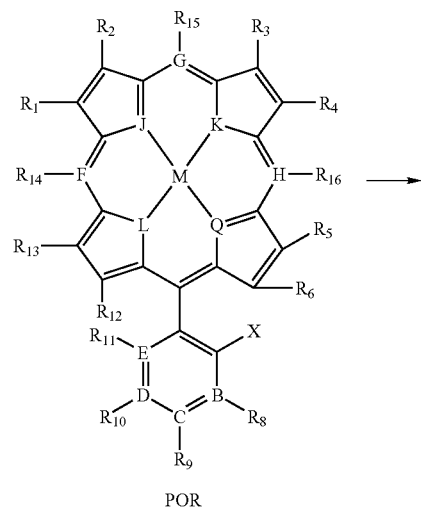

POR

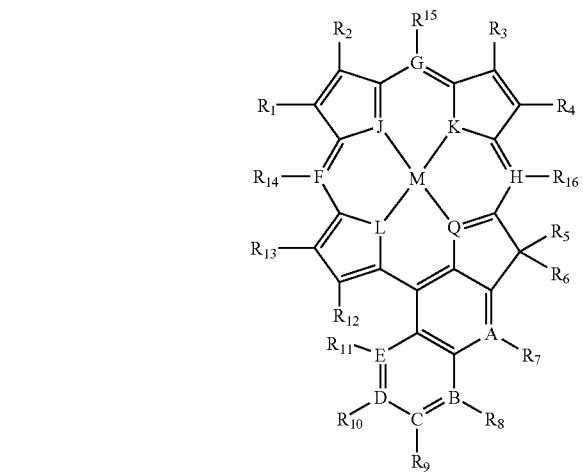
I
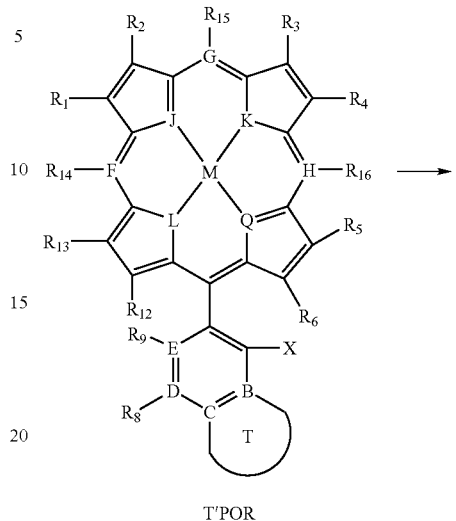
T'POR
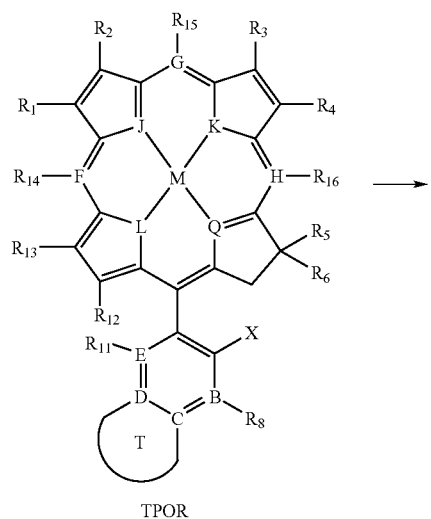
TPOR
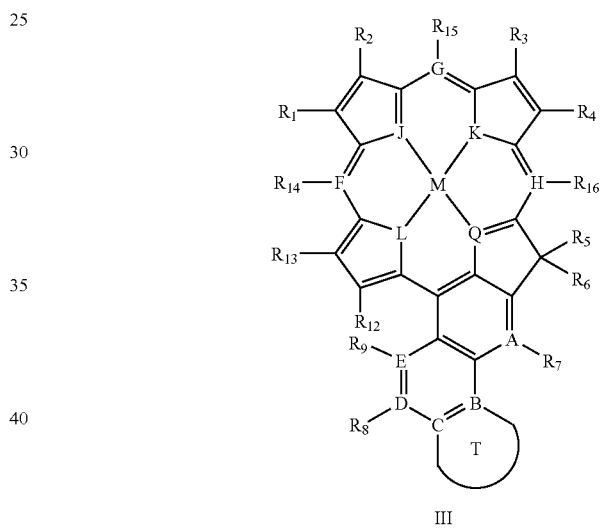
III
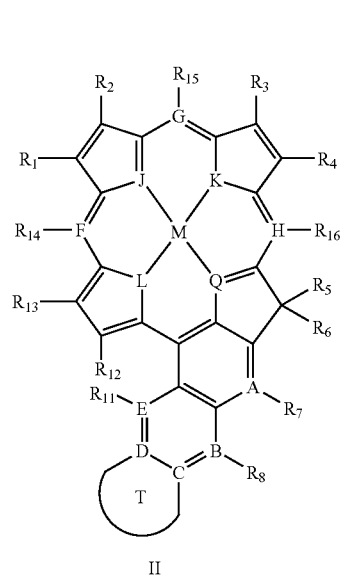
II
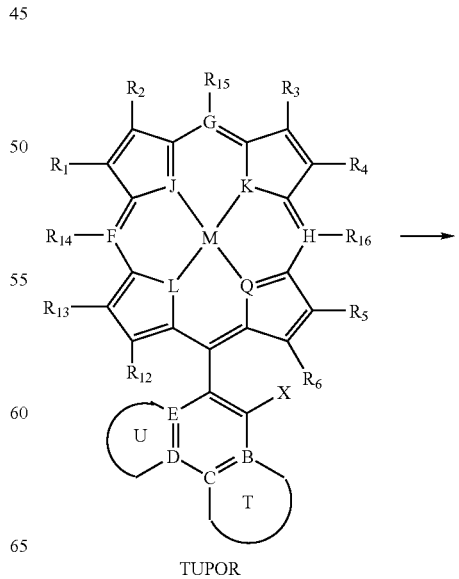
TUPOR

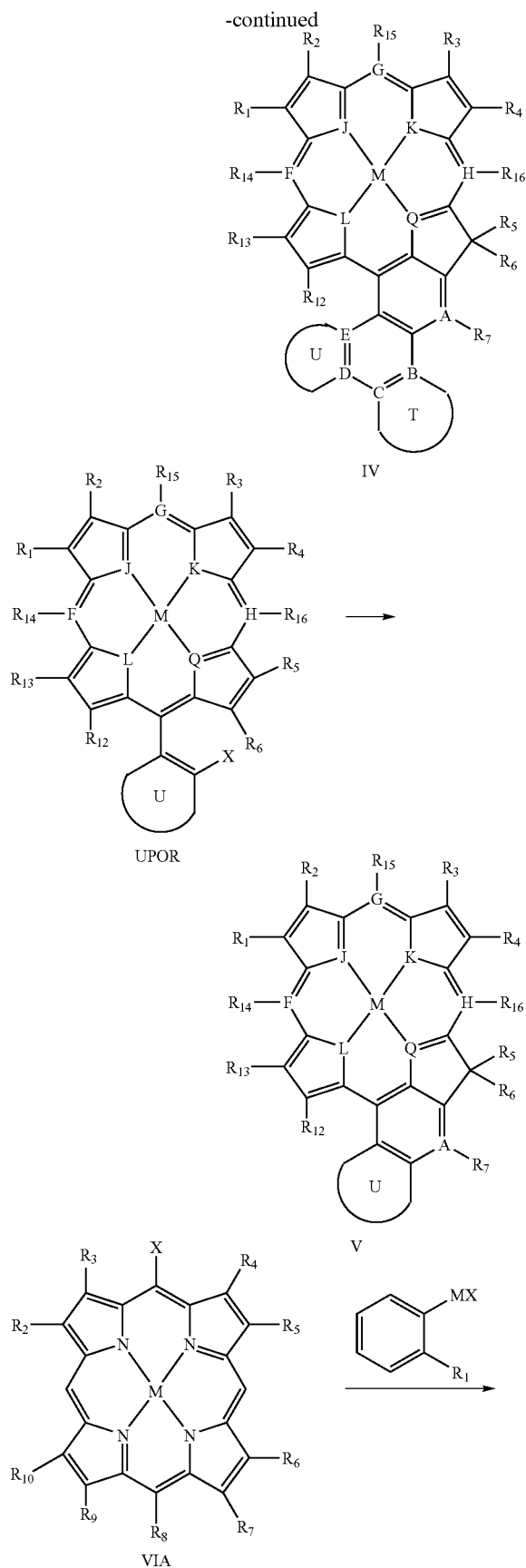
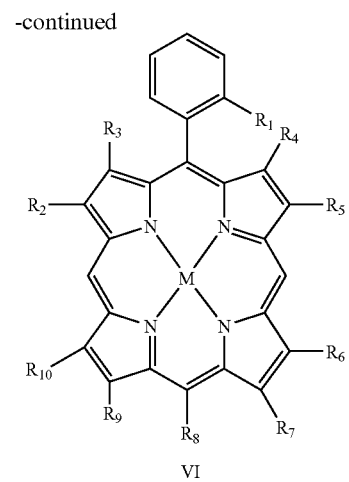

wherein the R groups are as defined above for reactions producing formulae I, II, III, IV, and V; X is $CH_2OH$, $CH_2N(R_\alpha)_3{}^+Z'''^-$, $CH_2OR_\alpha$, $CHR_7OR_\alpha$, or $CHR_7N(R_\alpha)_3{}^+Z'''^-$, or $CH_2\Phi$ where $\Phi$ is a halogen;

$Z'''^-$ is a charge balancing ion; and $R_\alpha$ is hydrogen, alkyl, or aryl.

In formula VI, $R_1$, $R_2$, $R_3$, $R_4$, $R_5$, $R_6$, $R_7$, $R_8$, $R_9$, and $R_{10}$ are independently selected from hydrogen; halogen; unsubstituted or substituted alkyl, $C_3$-$C_6$ cycloalkyl, acetyl, aryl, alkenyl, alkynyl, amide groups, or esters gropus; $NR_{17}R_{18}$; $CH_2NR_{17}R_{18}$; vinyl; $N(R_{17})(R_{18})(R_{19})^+Z^-$; $CH=CHNR_{17}R_{18}$; $CH_2CH_2NR_{17}R_{18}$; $CH=CHN(R_{17})(R_{18})(R_{19})^+Z^-$; $CH_2CH_2N(R_{17})(R_{18})(R_{19})^+Z^-$; $CHOHCH_3$; $CHOR_{17}CH_3$; $CN$; $OH$; $OR_{17}$; $CHO$; $CH=CHCO_2R_{17}$; $(CH_2)_nOH$; $(CH_2)_nSH$; $(CH_2)_nO$-alkoxy; $(CH_2)_nSR_{17}$; $(CH_2)_n$ $OR_{17}$; $(CH_2)_nCO_2R_{17}$; $(CH_2)_nCONHR_{17}$; $(CH_2)_n$ $CON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+Z^-$;

$R_{17}$, $R_{18}$, and $R_{19}$ are independently selected from hydrogen; a physiologically acceptable ion; unsubstituted or substituted $C_1$-$C_6$ alkyl, aryl, alkenyl or alkynyl; and a functional group having a molecular weight less than about 100,000 daltons;

$Z^-$ is a charge balancing ion;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr; and X' is a halogen.

The reation of a compound of formula VIA to form a compound of formula VI may proceed in the presence of a catalyst.

The invention also includes a process for preparing a porphyrin comprising contacting a compound selected from pyrroles; dipyrromethanes; dipyrromethenes; 1, 19-dideoxybilanes; 1, 19-dideoxybilenes-b; 1, 19-dideoxybiladienes-ac; and 1, 19-dideoxybilatrienes-abc; with a compound selected from

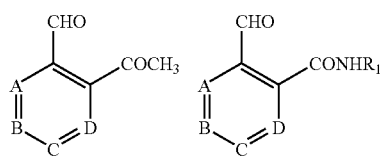

-continued

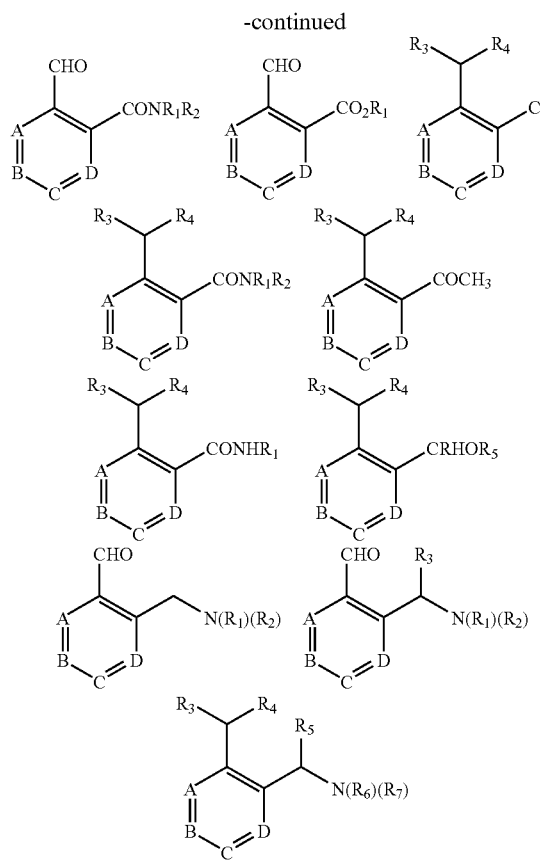

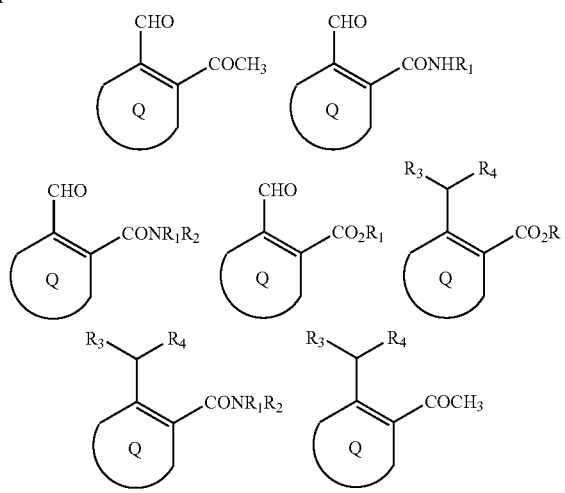

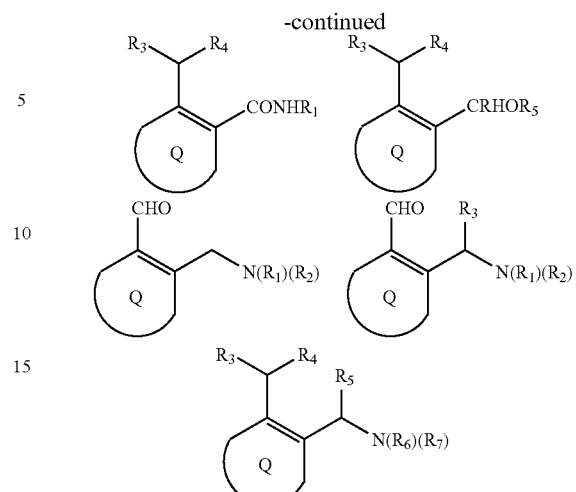

wherein $R_1$, $R_2$, $R_3$, $R_4$, $R_5$, $R_6$, and $R_7$ are independently selected from hydrogen; substituted or unsubstituted alkyl containing 0 or more carbon atoms, aryl, O(alkyl), $OCOCH_3$; and a protecting group;

A, B, C, D are independently selected from carbon, nitrogen, sulfur, selenium, telurium, oxygen, and phosphorous;

under sufficient conditions to form a porphyrin.

In another aspect of the invention, a process is provided for preparing a porphyrin comprising contacting at least one compound selected from pyrroles; dipyrromethanes; 1,1-dideoxybilanes; 1,19-dideoxybilenes-b; 1,19-dideoxybiladienes-ac; and 1,19-dideoxybilatrienes-abc; with a compound selected from wherein $R_1$, $R_2$, $R_3$, $R_4$, $R_5$, $R_6$, and $R_7$ are independently selected from hydrogen; substituted or unsubstituted alkyl containing 0 or more carbon atoms, aryl, O(alkyl), $OCOCH_3$; and a protecting group; and Q is selected from a substituted or unsubstituted aryl, heteroaryl, cycloalkyl, and a heterocycloalkyl group;

under sufficient conditions to form a porphyrin, is provided.

In another aspect, the invention provides a process for preparing a porphyrin comprising contacting at least one compound selected from pyrroles; dipyrromethanes; dipyrromethenes; 1,19-dideoxybilanes; 1,19-dideoxybileses-b; 1,19-dideoxybiladienes-ac; and 1, 19-dideoxybilatrienes-abc; with ester derivatives of 2-formylbenzoate under sufficient conditions to form a porphyrin.

Additional advantages of the invention will be set forth in the detailed description which follows, and in part will be obvious from the description or may be learned by practice of the invention. The advantages of the invention can be realized and attained by means of the elements and combinations particularly pointed out in the appended claims.

DETAILED DESCRIPTION OF THE INVENTION

The compounds of the present invention are useful for the photodiagnosis and phototherapy of unwanted tissue, tumor, cancer and malignant tissue (hereinafter referred to as a "tumor"). When a human or animal with a tumor is treated with doses of a compound of the present invention and when appropriate light rays or electromagnetic waves are applied, the compound emits light (i.e., it fluoresces). The existence, position and size of the tumor can thereby be detected. This is called photodiagnosis.

When the tumor is irradiated with light of proper wavelength and intensity, the compound is activated to exert a cell killing effect against the tumor. This is called phototherapy.

Compounds intended for photodiagnosis and phototherapy ideally should have the following properties:

(a) non-toxic at normal therapeutic dosage unless and until activated by light;

(b) selectively photoactive;

(c) emit characteristic and detectable fluorescence when light rays or electromagnetic waves are applied;

(d) activated to an extent sufficient to exert a cell killing effect against tumors when irradiated with light rays or electromagnetic waves are applied;

(e) easily metabolized or excreted after treatment.

The compounds of the invention can be used for diagnosis and the therapeutic treatment of a broad range of tumors.

Examples of such tumors are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, cancer of the tongue, cerebral tumor, skin cancer, malignant goiter, prostatic cancer, cancer of the parotid gland, Hodgkin's disease, multiple myeloma, renal cancer, leukemia, and malignant lymphocytoma. For diagnosis, the sole requirement is that the tumor be capable of selectively fluorescing when exposed to proper light. For treatment, the tumor must be penetratable by the activation energy. For diagnosis, light of shorter wavelength is used whereas for therapeutic purposes, light of longer wavelength is used to permit ready penetration of the tumor tissue. The light rays should have sufficient intensity to cause the compounds to emit fluorescence for diagnosis and to exert a cell killing effect for therapy.

The compounds of the present invention are also useful for the treatment of ophthalmological disorders such as age-related macular degeneration, diabetic retinopathy and choroidal neovascularization; dermatological disorders such as psoriasis; gynecological disorders such as dysfunctional uterine bleeding; urological disorders such as condyloma virus; cardiovascular disorders such as restenosis and atherosclerotic plaques; and for hair removal.

The source of irradiation for photodiagnosis and phototherapy is not limited, but a laser beam is preferable because intensive light rays in a desired wavelength range can be selectively applied. For example, in photodiagnosis, the compound of the invention is administered to a human or animal body, and after a certain period of time, light rays are applied to the part to be examined. When an endoscope can be used for the affected part, such as lungs, gullet, stomach, womb, urinary baldder or rectum, it is irradiated using the endoscope, and the tumor portion selectively emits fluorescence. This portion is observed visually, or observed through an adapted fiber scope by eye or on a CRT screen.

In phototherapy, after administration of the dosage, the irradiation is carried out by laser light from the tip of quartz fibers. Besides the irradiation of the surface of the tumor, the internal part of the tumor can be irradiated by inserting the tip of quartz fibers into the tumor. The irradiation can be visually observed or imaged on a CRT screen.

For photodiagnosis, light of wavelength between about 300 and about 850 nm is suitable for activating the compounds of the invention. Of course, each compound has a specific optimal wavelength of activation. A long wavelength ultraviolet lamp is particularly suitable for photodiagnosis. Similar methods for viewing the treated tumor can be used as already described for phototherapy.

The tetrapyrroles can be prepared by various synthetic methods which are found in the literature, e.g., "Porphyrins and Metalloporphyrins" ed. Kevin M. Smith, Elsevier 1975 N.Y.; "The Porphyrins", Ed. D. Dolphin, Academic Press, 1978, NY. References to the synthesis of 5-aryl substituted porphyrins are; Harris, D, Johnson, A. W., Gaete-Holmes, R., Bioorganic Chemistry, 9, 63-70, 1980. Routes to the synthesis of the ubiquitous tetrapyrrolic macrocycles that contain in their macrocyclic ring system 11 double bonds (excluding peripheral substituents), is outlined in detail in several books including "Porphyrins and Metalloporphyrins" Ed. K. M. Smith, Elsevier Publishing Company, New York, 1975, Chapter 2, p29-55; chapter 19, p778-785 and "The Porphyrins" Ed. D. Dolphin, Academic Press, 1978, Volume I. References within these volumes provide actual experimental details. A very large number of porphyrinic compounds have been synthesized. As they are prevalent in nature, a large number of studies on the chemical modification of these compounds have been undertaken ("The Porphyrins" Ed. D. Dolphin, Academic Press, 1978, Volume I, p 289-339.). A great deal of work has been undertaken on the synthesis of porphyrins from mono-pyrrols ("The Porphyrins" Ed. D. Dolphin, Academic Press, 1978, Volume I, chapter 3, 85-100; chapter 4, 101-234, chapter 5, 235-264; chapter 6, 265-288). Notable valuable examples of such work are in the synthesis of mono, di, tri and tetraphenyl porphyrins ("The Porphyrins" Ed. D. Dolphin, Academic Press, 1978, Volume I, chapter 3, 88-90; Gunter, M. J., Mander, L. N., J. Org. Chem. 46, 4792-4795, 1981.). Such compounds can be widely functionalized as the aromatic rings may possess different substituents or have incorporated in them heteroatoms. Porphyrins also can be synthesized that possess annelated aromatic rings on the β-pyrrole positions (T. D. Lash, C. Wijesinghe, A. T. Osuma, J. R. Patel, Tetrahedron Letters, 38(12), 2031-2034, 1997), which can have the effect of extending conjugation and modifying the absorption and photophysical properties of the compounds. Porphyrin-type compounds have been synthesized from pyrroles and 5-membered ring heterocycles (such as thiophenes or furans for example) which incorporated one or more heteroatom besides nitrogen within the central porphyrin "core" ("Porphyrins and Metalloporphyrins" Ed. K. M. Smith, Elsevier Publishing Company, New York, 1975, Chapter 18, 729-732). Such compounds can be modified similarly to produce highly functionalized derivatives. In addition, porphyrin dimers, trimers or oligomers have been synthesized in large numbers. (H. Meier, Y. Kobuke, S. Kugimiya, J. Chem. Soc. Chem. Commun., 923, 1989; G. M. Dubowchik, A. D. Hamilton, J. Chem. Soc. Chem. Commun.,904, 1985; R. K. Pandey, F-Y. Shaiu, C. J. Medforth, T. J. Dougherty, K. M. Smith, Tetrahedron Letters, 31, 7399, 1990; D. R. Arnold, L. J. Nitschinsk, Tetrahedron Letters, 48, 8781, 1992; J. L. Sessler, S. Piering, Tetrahedron Letters, 28, 6569, 1987; A. Osaku, F. Kobayashi, K. Maruyama, Bull. Chem. Soc. Jpn, 64, 1213, 1991).

Porphyrins that possess at least one meso-nitrogen linking atom are called azoporphyrins. The number of meso-nitrogen linking atoms may be extended from one to four. Phthalocyanines and naphthalocyanine may be regarded as tetraazoporphyrins with extended conjugation due to annelated benzene and naphthalene rings. The synthesis of mono, di, tri and tetra-azoporphyrin analogues is discussed in "The Porphyrins," Ed. D. Dolphin, Academic Press, 1978, Volume I, Chapter 9, p 365-388; "Phthalocyanines Properties and Applications," Eds. C. C. Leznoff, A. B. P. Lever, VCH Publishers Inc., 1989; "The Phthalocyanines", Eds, F. H. Moser, A. L. Thomas, CRC Press, Volumes I and II, 1983. References within these volumes provide actual experimental details. The synthesis of a series of terabenzotriazoporphyrins has recently been published (Tse, A. Goel, M. Hue, A. B. P, Lever, C. C. Leznoff, Can. J. Chem. 71, 742, 1993.) and clearly it can be envisaged that chemistry typical of phthalocyanine chemistry may be applied to these compounds, such that hetero atoms may be introduced into the annelated aromatic ring systems.

Figure 1:
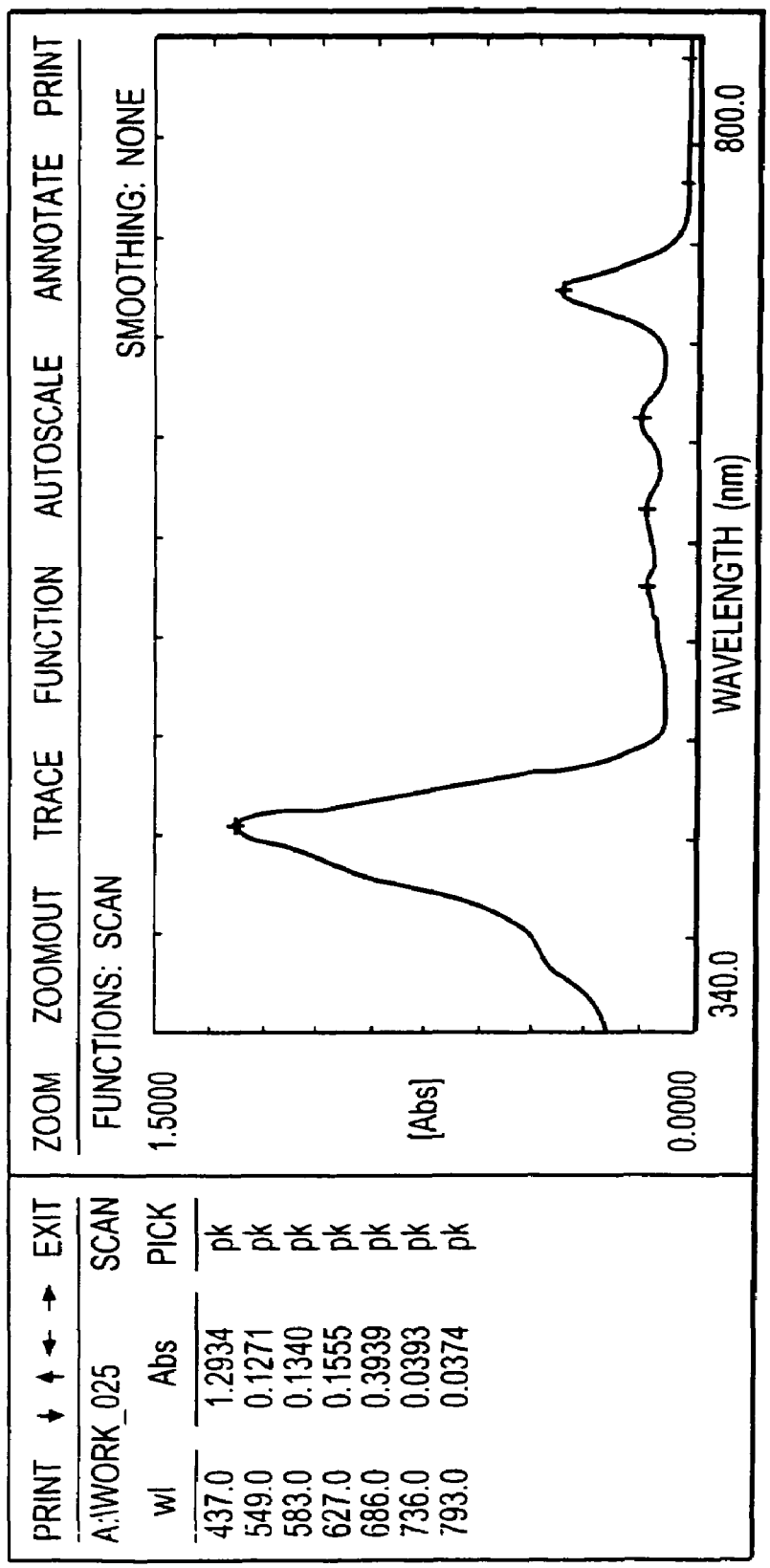
FIG. 1 is a UV/Visible spectrum of compound 7.

In accordance with the invention, as embodied and broadly described herein, naphthochlorins and chlorins possessing fused ring systems are provided that are particularly useful as photoselective compounds in photodynamic therapy. The present invention includes naphthochlorins of formula I and chlorins possessing fused ring systems of formulae II, III, IV, and V.

A) Napthachlorins (Formula I)

In accordance with the invention, as embodied and broadly described herein, the present inventors discovered that the naphthochlorins can be successfully synthesized by cyclization of compounds such as meso-(2'-hydroxymethyl)phenyl porphyrins in the presence of at least one acid catalyst for a sufficient time and at a sufficient temperature.

Synthesis of Napthochlorins from Compounds such as meso-(2'-methoxycarbonyl)phenyl porphyrins.

Scheme 1 outlines the chemistry involved in the synthesis of naphthochlorins from meso-(2'-methoxycarbonyl)phenyl porphyrins

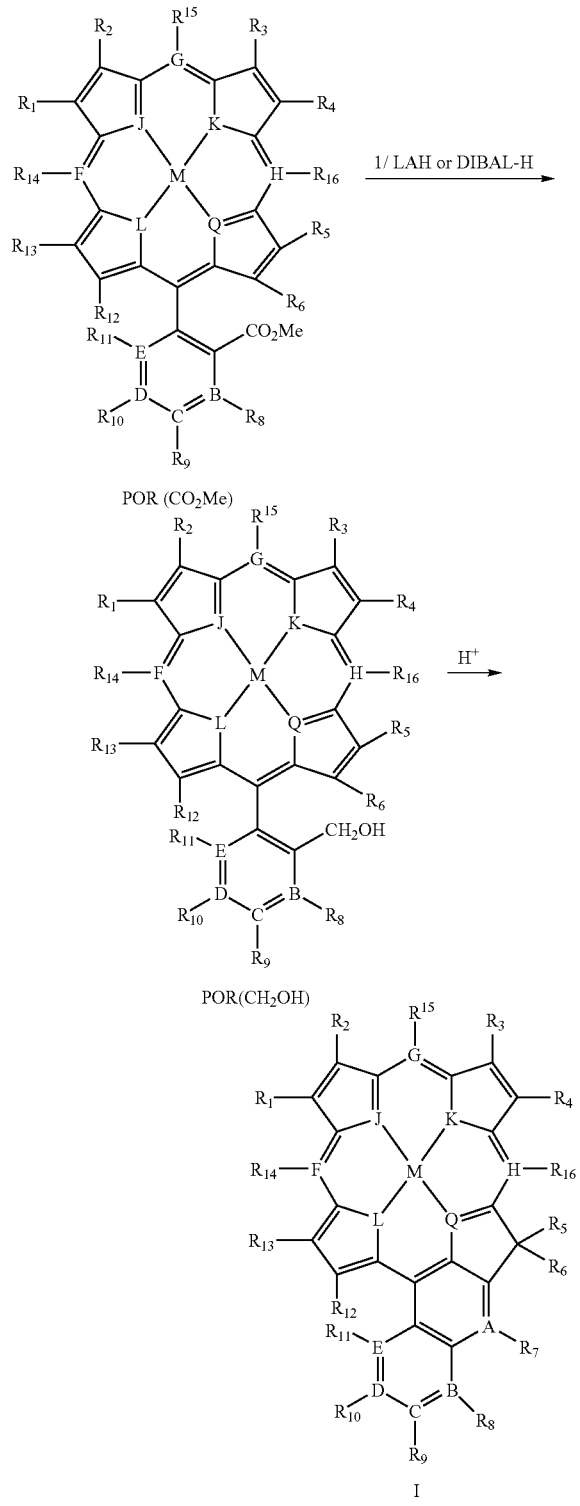

Porphyrins of formulae POR($CH_2OH$) may be used to prepare the compounds outlined in scheme 1 wherein, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are independently selected from hydrogen; halogen; unsubstituted or substituted alkyl containing 0 or more carbon atoms, $C_3$-$C_6$ cycloalkyl, acetyl, aryl, alkenyl, alkynyl, amide groups or ester groups; $NR_{17}R_{18}$; vinyl; $N(R_{17})(R_{18})(R_{19})^+Z^-$; $CH=CHNR_{17}R_{18}$; $CH_2CH_2NR_{17}R_{18}$; $CH=CHN(R_{17})(R_{18})(R_{19})^+Z^-$; $CH_2CH_2N(R_{17})(R_{18})(R_{19})^+Z^-$; $CHOHCH_3$; $CHOR_{17}CH_3$; $CN$; $OH$; $OR_{17}$; $CHO$; $CH=CHCO_2R_{17}$; $(CH_2)_nOH$; $(CH_2)_nSH$; $(CH_2)_n$O-alkoxy; $(CH_2)_nSR_{17}$; $(CH_2)_nOR_{17}$; $(CH_2)_nCO_2R_{17}$; $(CH_2)_n$ $CONHR_{17}$; $(CH_2)_nCON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+Z^-$;

$R_{17}$, $R_{18}$, and $R_{19}$ are independently selected from hydrogen, a physiologically acceptable salt; unsubstituted or substituted $C_1$-$C_6$ alkyl, aryl, alkenyl or alkynyl; and a functional group having a molecular weight less than about 100,000 daltons;

$Z^-$ is a charge balancing ion;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr;

A, B, C, D, E, F, G, H, J, K, L, Q are independently selected from carbon, sulfur, nitrogen, $N^+(R_{20})Z'^-$, oxygen, Se, and Te;

$R_{20}$ is a functional group having a molecular weight less than about 100,000 daltons, and $Z'^-$ is a charge balancing ion.

The invention includes compounds of formula IA

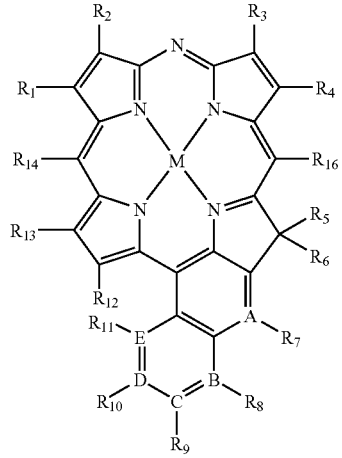

wherein:

$R_1$, $R_2$, $R_3$, $R_4$, $R_5$, $R_6$, $R_{12}$, and $R_{13}$ are independently selected from hydrogen, methyl, ethyl, $(CH_2)_nOH$, $(CH_2)_n$O-alkoxy, $(CH_2)_nOR_{17}$, $(CH_2)_nCO_2R_{17}$, $(CH_2)_nCONHR_{17}$, $(CH_2)_nCON(R_{17})(R_{18})$, where $R_{17}$ and $R_{18}$ are independently selected from a functional group having a molecular weight less than about 100,000 daltons, and n is an integer ranging from 1 to 4;

$R_7$, $R_8$, $R_9$, $R_{10}$, and $R_{11}$ are independently selected from an alkyl group containing 0 or more carbon atoms, hydrogen, $SO_3H$, $SO_3R_{17}$, $SO_2NHR_{17}$, $SO_2N(R_{17})(R_{18})$, and $SO_2N(R_{17})(R_{18})(R_{19})^+Z^-$;

$R_{17}$, $R^{18}$, and $R_{19}$ are independently selected from hydrogen; a physiologically acceptable ion; unsubstituted or substituted $C_1$-$C_6$ alkyl or aryl; and a functional group having a molecular weight less than about 100,000 daltons;

$Z^-$ is a charge balancing ion;

$R_{14}$ and $R_{16}$ are independently selected from hydrogen and methyl; and

M is two hydrogens or a metal ion selected from In, Pd, Pt, Sn, Zn, Ga, Al, and Mg.

Another embodiment of formula IA is found when $R_1$, $R_4$, $R_5$, $R_6$, $R_{12}$, $R_{13}$ are independently selected from methyl and ethyl;

$R_7$, $R_8$, $R_9$, $R_{10}$, $R_{11}$, $R_{14}$, and $R_{16}$ are independently selected from hydrogen and methyl;

$R_2$ and $R_3$ are independently selected from methyl, ethyl, $(CH_2)_2OH$, $(CH_2)_2OMe$, $(CH_2)_3OH$, $(CH_2)_3OMe$, $(CH_2)_2CO_2Me$, $(CH_2)_2CO_2Na$, $(CH_2)_2CO_2K$, $(CH_2)_2CONHR_{17}$, $(CH_2)_2CON(R_{17})(R_{18})$, $(CH_2)_3OH$, $(CH_2)_3OMe$, $CH_2CO_2Me$, $CH_2CO_2Na$, and $CH_2CO_2K$;

$R_{17}$ and $R_{18}$ are independently selected from $CH_3$, $CH_2CH_3$, $CH_2OCH_2OH$, $CH_2CH_2N(CH_3)_2$, and $CH_2CH_2N(CH_3)_3{}^+S^-$, where $S^-$ is a physiologically acceptable ion; and M is two hydrogens or a metal ion selected from In, Pd, Pt, Sn, Zn, Ga, Al, and Mg.

In one embodiment of formula IB,

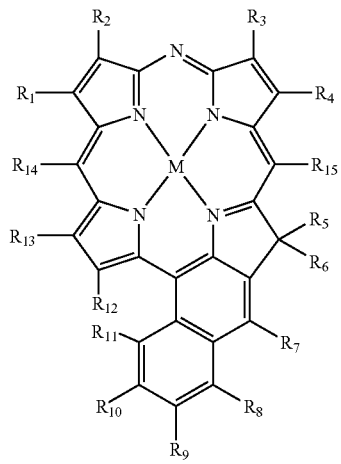

IB $R_1$-$R_{14}$, $R_{16}$, and M are defined as in formula I.

In another embodiment of formula IB, $R_1$, $R_2$, $R_3$, $R_4$, $R_5$, $R_6$, $R_{12}$, and $R_{13}$ are independently selected from hydrogen, methyl, ethyl, $(CH_2)_nOH$, $(CH_2)_nO$-alkoxy, $(CH_2)_nOR_{17}$, $(CH_2)_nCO_2R_{17}$, $(CH_2)_nCONHR_{17}$, $(CH_2)_nCON(R_{17})(R_{18})$;

$R_7$, $R_8$, $R_9$, $R_{10}$, and $R_{11}$ are independently selected from hydrogen, $SO_3H$, $SO_3R_{17}$, $SO_2NHR_{17}$, $SO_2N(R_{17})(R_{18})$, and $SO_2N(R_{17})(R_{18})(R_{19})^+Z^-$;

$R_{14}$ and $R_{16}$ are hydrogen; and

M is two hydrogens or a metal ion selected from In, Pd, Pt, Sn, Zn, Ga, Al, and Mg.

In another embodiment of formula IB, $R_1$, $R_4$, $R_5$, $R_6$, $R_{12}$, and $R_{13}$ are independently selected from methyl and ethyl;

$R_7$, $R_8$, $R_9$, $R_{10}$, $R_{11}$, $R_{14}$, and $R_{16}$ are independently selected from hydrogen and methyl;

$R_2$ and $R_3$ are independently selected from methyl, ethyl, $(CH_2)_2OH$, $(CH_2)_2OMe$, $(CH_2)_3OH$, $(CH_2)_3OMe$, $(CH_2)_2CO_2Me$, $(CH_2)_2CO_2Na$, $(CH_2)_2CO_2K$, $(CH_2)_2CONHR_{17}$, $(CH_2)_2CON(R_{17})(R_{18})$, $(CH_2)_3OH$, $(CH_2)_3OMe$, $CH_2CO_2Me$, $CH_2CO_2Na$, and $CH_2CO_2K$;

$R_{17}$ and $R_{18}$ are independently selected from $CH_3$, $CH_2CH_3$, $CH_2OCH_2OH$, $CH_2CH_2N(CH_3)_2$, and $CH_2CH_2N(CH_3)_3{}^+S^-$, where $S^-$ is a physiologically acceptable ion; and M is two hydrogens or a metal ion selected from In, Pd, Pt, Sn, Zn, Ga, Al, and Mg.

The invention includes an embodiment of formula IC wherein

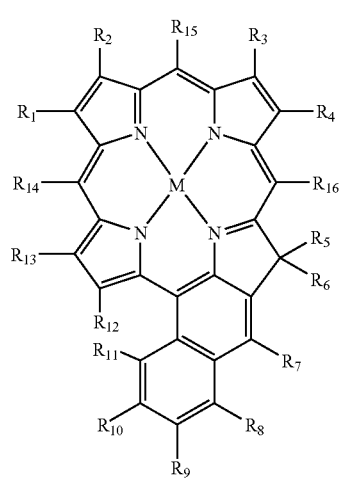

IC $R_1$, $R_2$, $R_3$, $R_4$, $R_5$, $R_6$, $R_{12}$, and $R_{13}$ are independently selected from hydrogen, methyl, ethyl, $(CH_2)_nOH$, $(CH_2)_nO$-alkoxy, $(CH_2)_nOR_{17}$, $(CH_2)_nCO_2R_{17}$, $(CH_2)_nCONHR_{17}$, and $(CH_2)_nCON(R_{17})(R_{18})$;

$R_7$, $R_8$, $R_9$, $R_{10}$, and $R_{11}$ are independently selected from hydrogen, $SO_3H$, $SO_3R_{17}$, $SO_2NHR_{17}$, $SO_2N(R_{17})(R_{18})$, and $SO_2N(R_{17})(R_{18})(R_{19})^+Z^-$;

$R_{14}$, $R_{15}$, and $R_{16}$ are hydrogen; and

M is selected from two hydrogens and a metal ion selected from In, Pd, Pt, Sn, Zn, Ga, Al, and Mg.

In another embodiment, the invention includes a compound of formula ID

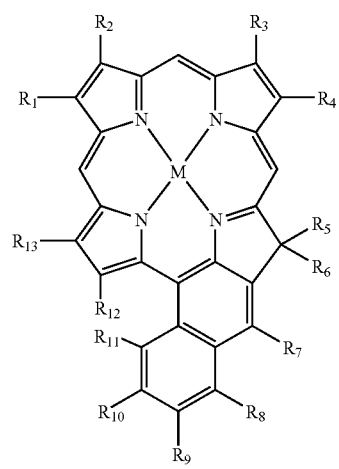

ID wherein:

$R_1$, $R_4$, $R_5$, $R_6$, $R_{12}$, and $R_{13}$ are independently selected from methyl and ethyl;

$R_7$, $R_8$, $R_9$, $R_{10}$, and $R_{11}$ are hydrogen, $R_2$ and $R_3$ are selected from methyl, ethyl, $(CH_2)_2OH$, $(CH_2)_2OMe$, $(CH_2)_3OH$, $(CH_2)_3OMe$, $(CH_2)_2CO_2Me$, $(CH_2)_2CO_2Na$, $(CH_2)_2CO_2K$, $(CH_2)_2CONHR_{17}$, $(CH_2)_2CON(R_{17})(R_{18})$, $(CH_2)_3OH$, $CH_2CO_2Me$, $CH_2CO_2Na$, and $CH_2CO_2K$;

$R_{17}$ and $R_{18}$ are independently selected from $CH_3$, $CH_2CH_3$, $CH_2OCH_2OH$, $CH_2CH_2N(CH_3)_2$, and $CH_2CH_2N(CH_3)_3{}^+S^-$, where $S^-$ is a physiologically acceptable ion; and M is selected from two hydrogens and a metal ion selected from In, Pd, Pt, Sn, Zn, Ga, Al, and Mg.

In another aspect of the invention, a compound of formula IE is provided

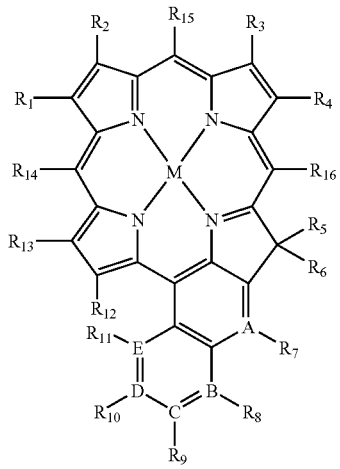

IE wherein $R_1$-$R_{16}$, A-E, and M are as defined as in formula I.

In another embodiment of formula IE, $R_1$, $R_2$, $R_3$, $R_4$, $R_5$, $R_6$, $R_{12}$, and $R_{13}$ are independently selected from hydrogen, methyl, ethyl, $(CH_2)_nOH$, $(CH_2)_nO$-alkoxy, $(CH_2)_nOR_{17}$, $(CH_2)_nCO_2R_{17}$, $(CH_2)_nCONHR_{17}$, $(CH_2)_nCON(R_{17})(R_{18})$;

$R_7$, $R_8$, $R_9$, $R_{10}$, and $R_{11}$ are independently selected from hydrogen, an alkyl group containing 0 or more carbon atoms, $SO_3H$, $SO_3R_{17}$, $SO_2NHR_{17}$, $SO_2N(R_{17})(R_{18})$, and $SO_2N(R_{17})(R_{18})(R_{19})^+Z'$;

$R_{14}$, $R_{15}$, and $R_{16}$ are hydrogen; and

M is selected from two hydrogens and a metal ion selected from In, Pd, Pt, Sn, Zn, Ga, Al, and Mg.

In another embodiment of formula IE, $R_1$, $R_4$, $R_5$, $R_6$, $R_{12}$, and $R_{13}$ are independently selected from methyl and ethyl;

$R_7$, $R_{14}$, $R_{15}$, $R_{16}$ are hydrogen;

$R_2$ and $R_3$ are independently selected from $(CH_2)_2OH$, $(CH_2)_2OMe$, $(CH_2)_3OH$, $(CH_2)_3OMe$, $(CH_2)_2CO_2Me$, $(CH_2)_2CO_2Na$, $(CH_2)_2CO_2K$, $CH_2)_2CONHR_{17}$, $(CH_2)_2CON(R_{17})(R_{18})$, $(CH_2)_3OH$, $(CH_2)_3OMe$, $CH_2 CO_2Me$, $CH_2 CO_2Na$, and $CH_2 CO_2K$;

$R_{17}$ and $R_{18}$ are independently selected from $CH_3$, $CH_2CH_3$, $CH_2OCH_2OH$, $CH_2CH_2N(CH_3)_2$, and $CH_2CH_2N(CH_3)_3{}^+S^-$, where $S^-$ is a physiologically acceptable ion; and M is selected from two hydrogens and a metal ion selected from In, Pd, Pt, Sn, Zn, Ga, Al and Mg.

In yet another aspect of the invention, a compound of formula IF is provided

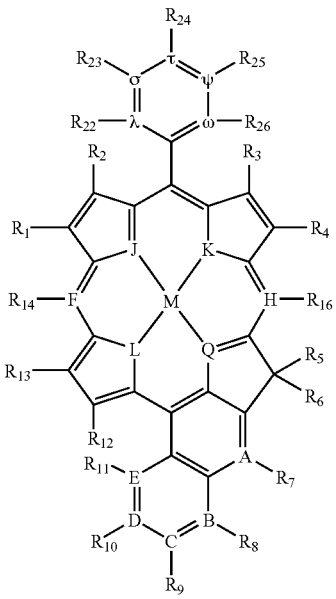

IF wherein:

$R_1$-$R_{14}$, and $R_{16}$ are defined as in formula I;

$R_{22}$, $R_{23}$, $R_{24}$, $R_{25}$, and $R_{26}$ are independently selected from hydrogen; halogen; unsubstituted or substituted alkyl containing 0 or more carbon atoms, $C_3$-$C_6$ cycloalkyl, acetyl, aryl, alkenyl, alkynyl, amide groups, or ester groups; $NR_{27}R_{28}$; vinyl; $N(R_{27})(R_{28})(R_{29})^+Y^-$; $CH=CHNR_{27}R_{28}$; $CH_2CH_2NR_{27}R_{28}$; $CH=CHN(R_{27})(R_{28})(R_{29})^+Y^-$; $CH_2CH_2N(R_{27})(R_{28})(R_{29})^+Y^-$; $CHOHCH_3$; $CHOR_{27}CH_3$; CN; OH; $OR_{27}$; CHO; $CH=CHCO_2R_{27}$; $(CH_2)_nOH$; $(CH_2)_nSH$; $(CH_2)_nO$-alkoxy; $(CH_2)_nSR_{27}$; $(CH_2)_nOR_{27}$; $(CH_2)_nCO_2R_{27}$; $(CH_2)_nCONHR_{27}$; $(CH_2)_nCON(R_{27})(R_{28})$; $CO_2R_{27}$; $CONHR_{27}$; $CONR_{27}R_{28}$; $SR_{27}$, $SO_3H$, $SO_3R_{27}$; $SO_2NHR_{27}$; $SO_2N(R_{27})(R_{28})$; and $SO_2N(R_{27})(R_{28})(R_{29})^+Y^-$;

$R_{27}$, $R_{28}$, and $R_{29}$ are independently selected from hydrogen, a physiologically acceptable salt; unsubstituted or substituted $C_1$-$C_6$ alkyl, aryl, alkenyl, or alkynyl; and a functional group having a molecular weight less than about 100,000 daltons;

$Y^-$ is a charge balancing ion;

$\lambda$, $\sigma$, $\tau$, $\psi$, $\omega$, are independently selected from carbon, nitrogen, $N^+(R_{21})Y^{1-}$, O, $Se^+$, $Te^+$; $R_{21}$ is selected from alkyl, aryl, and a functional group having a molecular weight less than about 100,000 daltons; $Y^{1-}$ is a charge balancing ion;

A, B, C, D, E, F, H, J, K, L, and Q are as defined in formula I; and

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr.

In one embodiment of formula IF,

J, K, L, and Q are nitrogen and F and H are carbon and the remaining variables are as defined immediately above.

In another embodiment of formula IF

A, B, C, D, and E are carbon;

$R_1$, $R_2$, $R_3$, $R_4$, $R_5$, $R_6$, $R_{12}$, and $R_{13}$ are independently selected from hydrogen, methyl, ethyl, $(CH_2)_2OH$, $(CH_2)_2OMe$, $(CH_2)_3OH$, $(CH_2)_3OMe$, $(CH_2)_2CO_2Me$, $(CH_2)_2CO_2Na$, $(CH_2)_2CO_2K$, $CH_2)_2CONHR_{27}$, $(CH_2)_2 CON(R_{27})(R_{28})$, $(CH_2)_3OH$, $(CH_2)_3OMe$, $CH_2CO_2Me$, $CH_2 CO_2Na$, and $CH_2CO_2K$;

$R_{27}$ and $R_{28}$ are independently selected from $CH_3$, $CH_2CH_3$, $CH_2OCH_2OH$, $CH_2CH_2N(CH_3)_2$, and $CH_2CH_2(N(CH_3)_3^+)S^-$, where $S^-$ is a physiologically acceptable ion; and $R_{14}$ and $R_{16}$ are hydrogen;

$R_7$, $R_8$, $R_9$, $R_{10}$, $R_{11}$, $R_2$ and $R_3$ are independently selected from hydrogen and methyl; and M is two hydrogens or a metal ion selected from In, Pd, Pt, Sn, Zn, Ga, Al, and Mg.

In yet another embodiment of formula IF

A, B, C, D, E, F, and H are carbon;

Q, T, U, and V are nitrogen;

$R_1$, $R_2$, $R_3$, $R_4$, $R_5$, $R_6$, $R_{12}$, and $R_{13}$ are independently selected from hydrogen, methyl, ethyl, $(CH_2)_nOH$, $(CH_2)_nO$-alkoxy, $(CH_2)_nOR_{27}$, $(CH_2)_nCO_2R_{27}$, $(CH_2)_nCONHR_{27}$, $(CH_2)_nCON(R_{27})(R_{28})$;

$R_7$, $R_8$, $R_9$, $R_{10}$, and $R_{11}$ are independently selected from $SO_3H$, $SO_3R_{27}$, $SO_2NHR_{27}$, $SO_2N(R_{28})(R_{29})$, and $SO_2N(R_{27})(R_{28})(R_{29})^+Y^-$;

$R_{27}$, $R_{28}$, and $R_{29}$ are independently selected from a functional group having a molecular weight less than about 100,000 daltons;

$R_{14}$ and $R_{16}$ are hydrogen;

$R_{22}$, $R_{23}$, $R_{24}$, $R_{25}$, and $R_{26}$ are independently selected from hydrogen, OH, $OR_{27}$, $N(R_{27})_2$, $N(R_{27})_3^+Z^-$, $CO_2H$, $CO_2Na$, $CO_2K$, $CO_2R_{27}$, $CONHR_{27}$, $CON(R_{27})_2$, $CON(R_{27})_3^+$; and M is selected from two hydrogens or a metal ion selected from In, Pd, Pt, Sn, Zn, Ga, Al, and Mg.

In another aspect of the invention, a compound of formula IG is provided

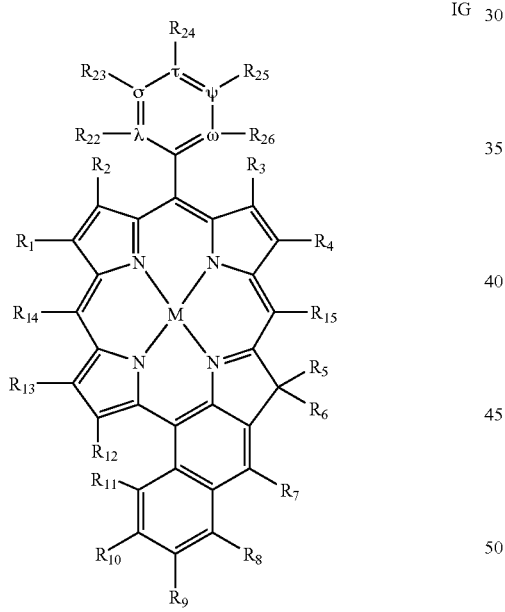

IG wherein:

$R_1$, $R_2$, $R_3$, $R_4$, $R_5$, $R_6$, $R_{12}$, and $R_{13}$ are independently selected from hydrogen, methyl, ethyl, $(CH_2)_2OH$, $(CH_2)_2OMe$, $(CH_2)_3OH$, $(CH_2)_2CO_2Me$, $(CH_2)_2CO_2Na$, $(CH_2)_2CO_2K$, $(CH_2)_2CONHR_{27}$, $(CH_2)_2CON(R_{27})(R_{28})$, $(CH_2)_3OH$, $(CH_2)_3OMe$, $CH_2CO_2Me$, $CH_2CO_2Na$, and $CH_2CO_2K$;

$R_{22}$, $R_{23}$, $R_{24}$, $R_{25}$, and $R_{26}$ are independently selected from hydrogen, aryl, OH, $OR_{27}$, $N(R_{27})_2$, $N(R_{27})_3Y^-$, $CO_2H$, $CO_2Na$, $CO_2K$, $CO_2R_{27}$, $CONHR_{27}$, $CON(R_{27})_2$, $CON(R_{27})_3^+Y^-$; and $R_{27}$, $R_{28}$, and $R_{29}$ are independently selected from a functional group having a molecular weight of less than about 100,000 daltons;

$R_7$, $R_8$, $R_9$, $R_{10}$, $R_{11}$, $R_{14}$, and $R_{15}$ are independently selected from hydrogen and methyl.

Preferred embodiments according to the invention include the following compounds:

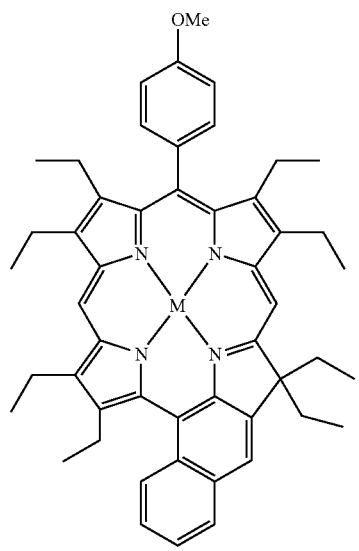

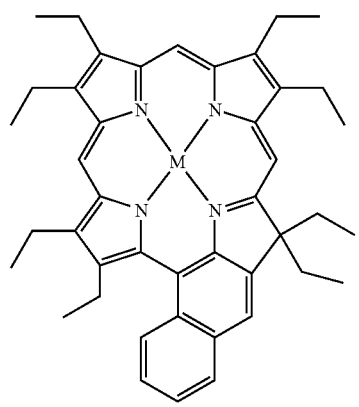

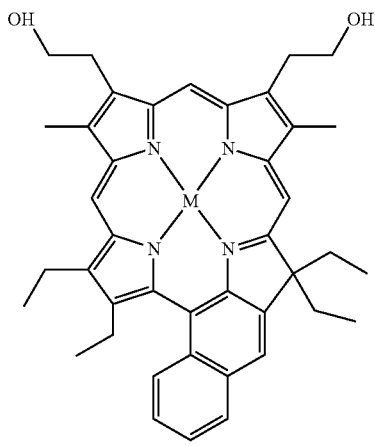

-continued

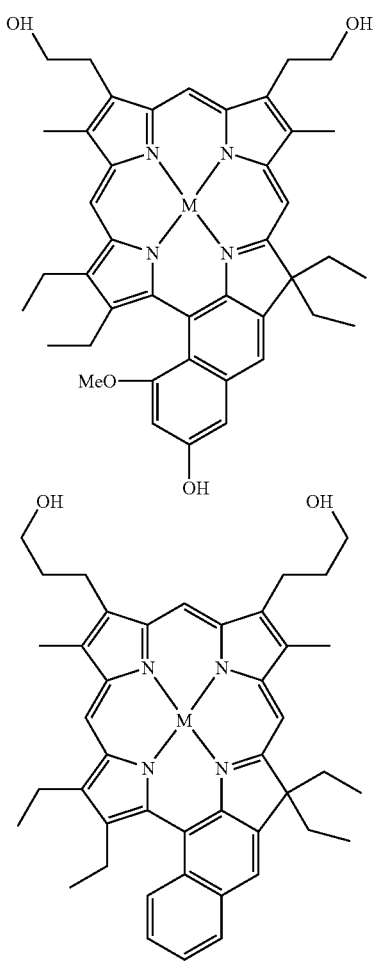

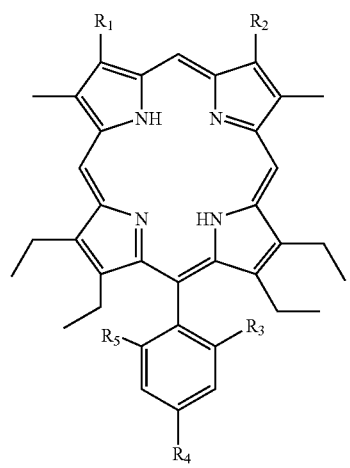

In one preferred embodiment, compounds such as meso-(2'-methoxycarbonyl)phenyl porphyrins may be reduced with lithium aluminium hydride (LAH), dibal-H (diisobutylaluminium hydride) or a suitable reducing agent to give meso-(2'-hydroxymethyl)phenyl porphyrins (PORCH$_2$OH) which may be used as a precursor to form a compound of formula I. Examples of the types of porphyrins used as precursors in the invention are shown below.

1) $R_1=R_2=CH_2COOCH_3$, $R_3=COOCH_3$, $R_4=R_5=OCH_3$
2) $R_1=R_2=CH_2CH_2OH$, $R_3=CH_2OH$, $R_4=R_5=OCH_3$
3) $R_1=R_2=CH_2CH_2COOCH_3$, $R_3=COOCH_3$, $R_4=R_5=H$
4) $R_1=R_2=CH_2CH_2CH_2OH$, $R_3=CH_2OH$, $R_4=R_5=H$

LAH reduction of porphyrins 1 and 3 gave porphyrins 2 and 4 respectively.

The invention further provides for the synthesis of the aforementioned compounds by contacting porphyrin precursors with at least one acid catalyst for a sufficient time at a sufficient temperature to form a compound of the invention.

While not limited, in preferred embodiments, the acid catalyst is selected from HCl, $H_2SO_4$, $H_3PO_4$, $CF_3CO_2H$, and MeSO$_3$H. $H_3PO_4$ is particularly preferred.

The invention includes reacting a compound of formula PORA with at least one acid catalyst for a sufficient time and at a sufficient temperature to form a compound of formula IA

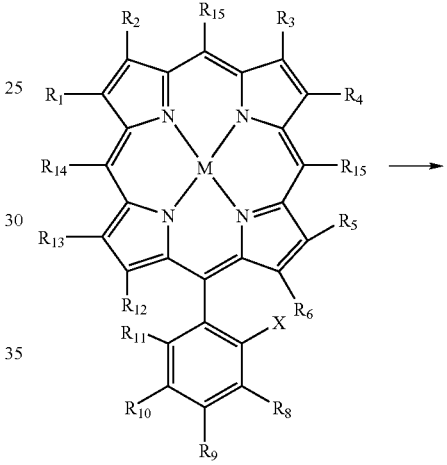

PORA

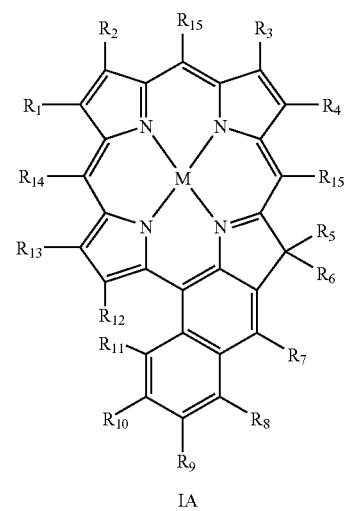

IA wherein $R_1$-$R_{16}$ and X have been previously defined.

In other embodiments, as shown below, porphyrin precursors are contacted with at least one acid catalyst for a sufficient time and at a sufficient temperature to form compounds of the invention:

27
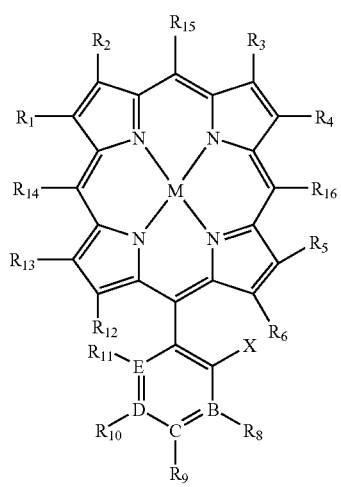
PORH
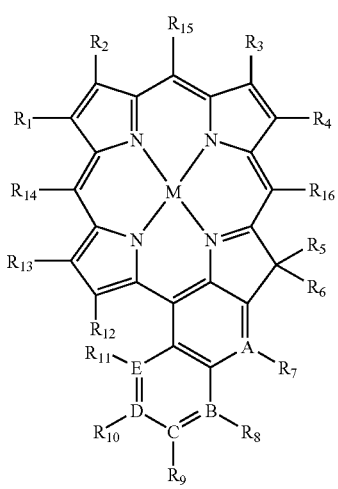
IH
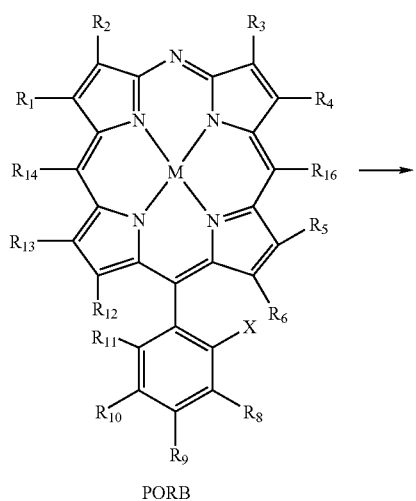
PORB
28
-continued
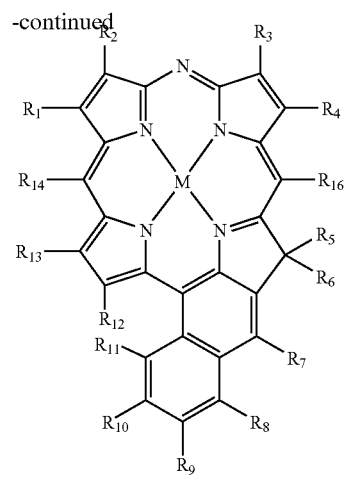
IB
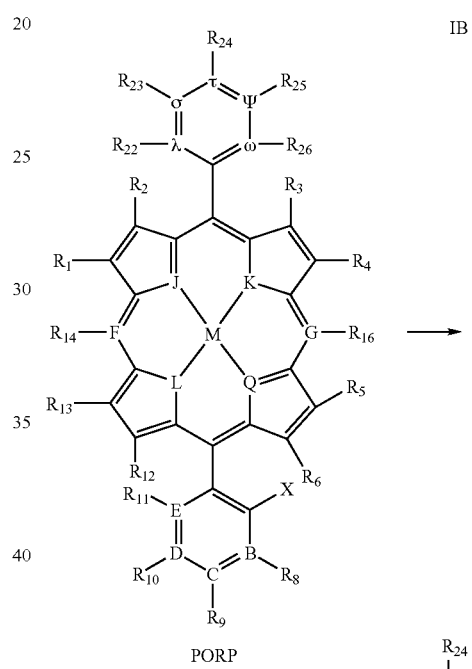
PORP
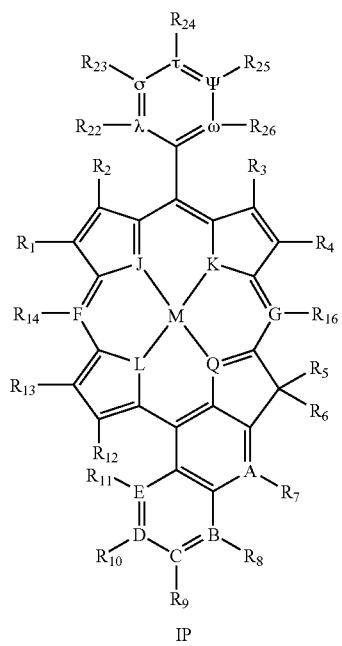
IP

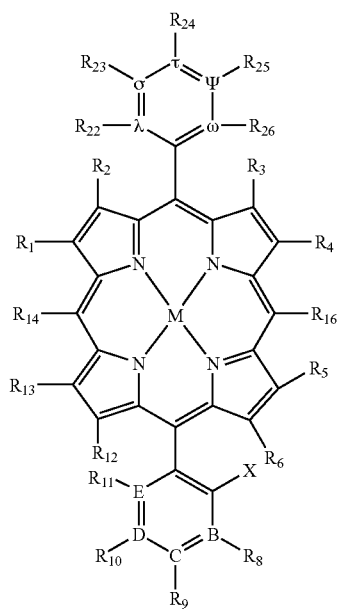

PORL

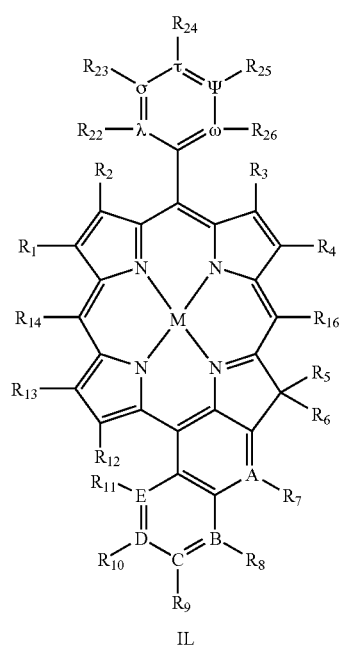

IL

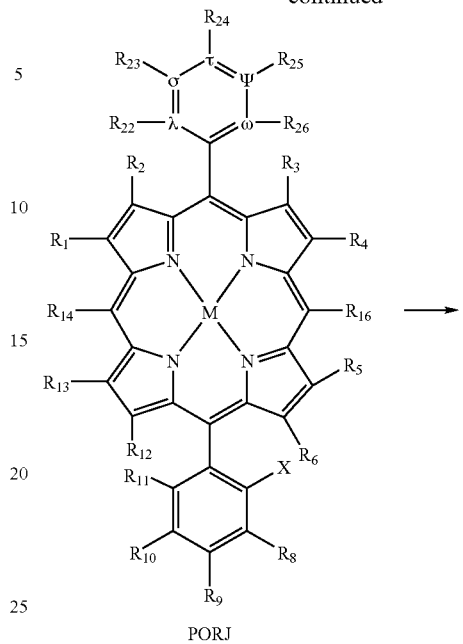

PORJ

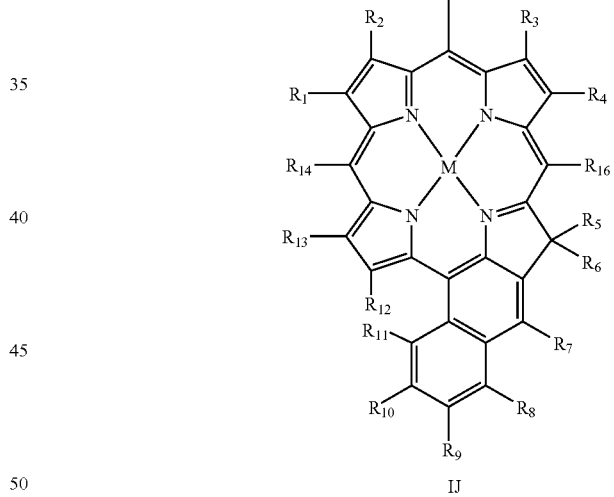

IJ wherein $R_1$-$R_{16}$, $\lambda$, $\sigma$, $\tau$, $\psi$, $\omega$, and X have been previously defined.

Biladiene 5 (A. W. Johnson and I. T. Kay, *J. Chem. Soc.*, 1965, 1620) on reaction with 3,5-dimethoxy-2-formyl methylbenzoate in methanol in the presence of HBr gave porphyrin 1 (Scheme 2). Following similar reaction conditions, porphyrin 3 was synthesized from biladiene 6 (R. Grigg et al., *J. Chem. Soc.* (C), 1969, 176) and methyl 2-formyl benzoate in presence of HBr (cat.) (Scheme 3).

The synthesis of naphthochlorins 7 and 8 was achieved by cyclization of the meso-(2'-hydroxymethyl)phenyl porphyrins 2 and 4 respectively in phosphoric acid at 90°-100° C., under argon atmosphere (Schemes 2 and 3 below). The reaction time preferably ranged from 1.5 hours to 2 hours.

Figure 2:
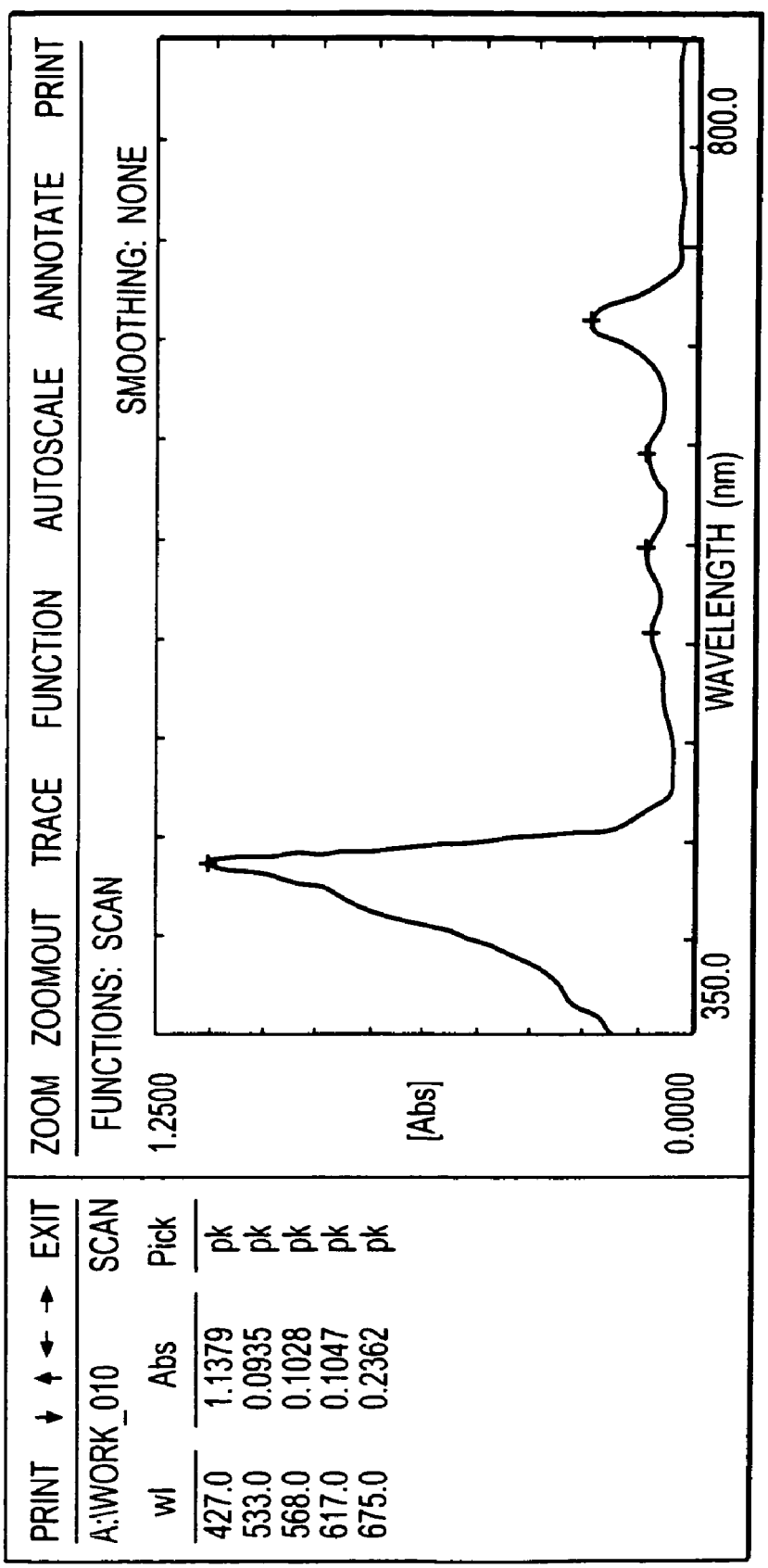
FIG. 2 is a UV/Visible spectrum of compound 8.
Reference will now be made in detail to several embodiments of the present invention.

The structures of compounds 7 and 8 were assigned by $^1$H NMR spectra. It was observed, in compound 7 that demethylation occurred (Scheme 4) on one of the methoxyl groups of the exocyclic naphthalene moiety during the acid catalyzed cyclization step. The structure of 7 was further confirmed by NOE enhancement experiments. The UV/Visible absorption spectra of compounds 7 and 8 are shown in FIGS. 1 and 2. These naphthochlorins display prominent absorption in the UV/Visible spectrum at ~675-686 nm and a broad Soret absorption band at ~424-434 nm.

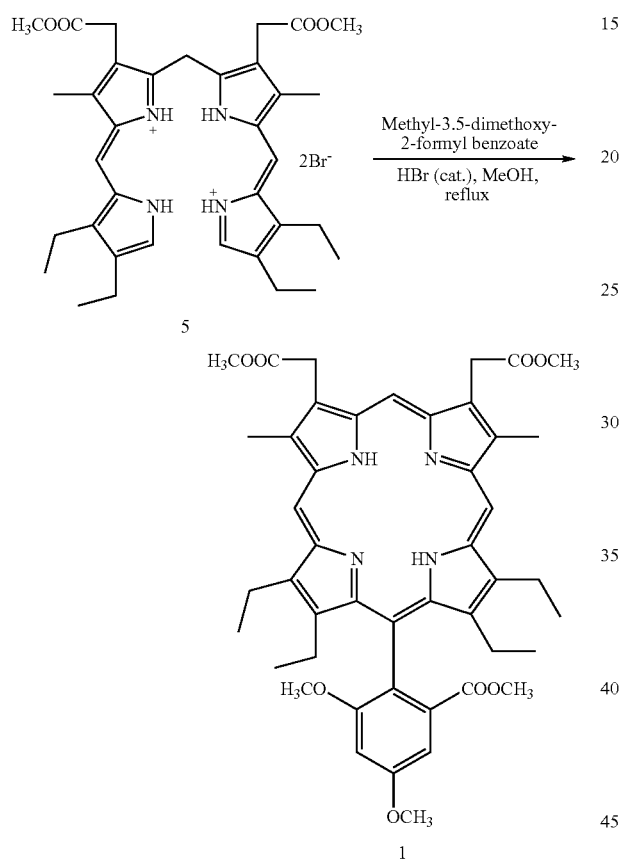

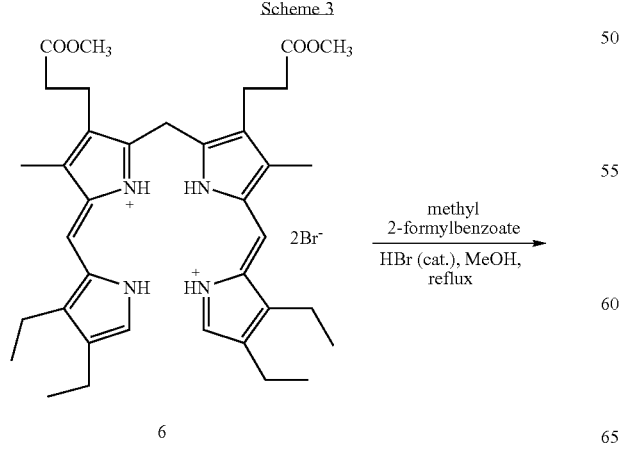

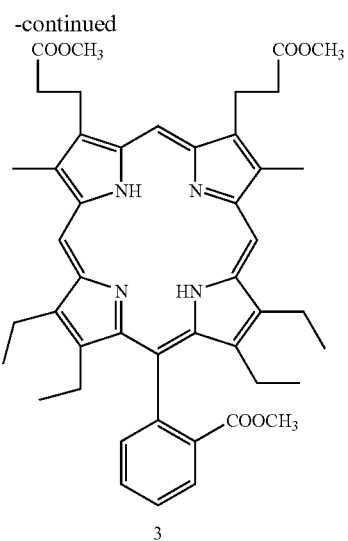

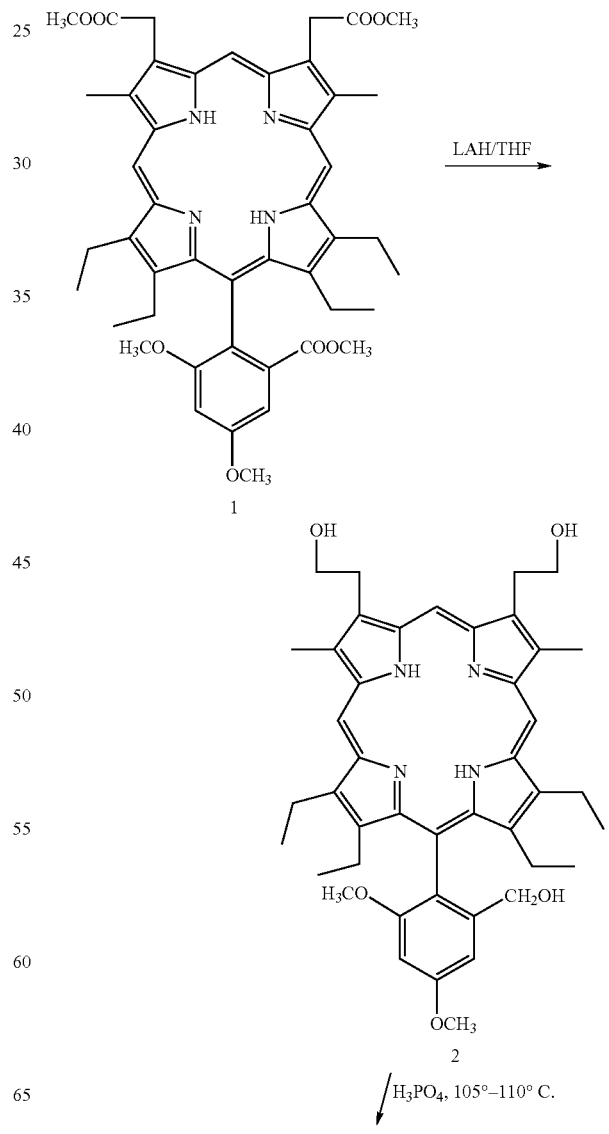

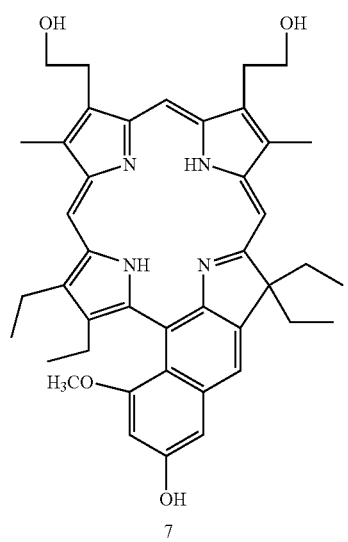
7
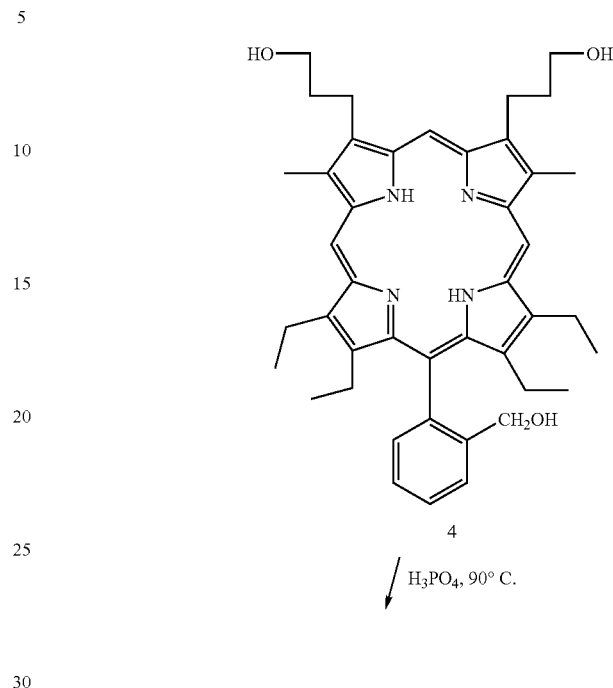
4
↓ H₃PO₄, 90° C.
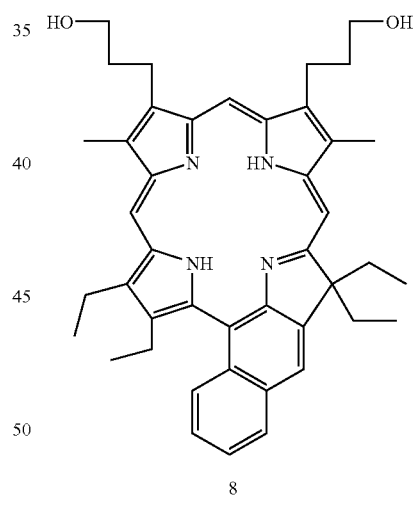
8
Scheme 5
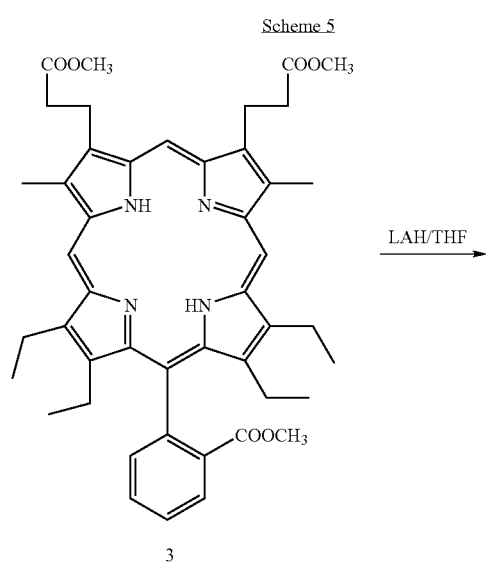
3
LAH/THF →
Reaction of 3,4,3',4'-tetraethyldipyrromethane with methyl-2-formyl benzoate in methanol and toluene sulfonic acid gives porphyrin 9 after oxidation of the solution with DDQ (scheme 6). Reduction of 9 with DIBAL-H in dichloromethane, followed by acid catalysed cyclization with phosphoric acid ($H_3PO_4$), gave the napthochlorin 10 in 60% yield.

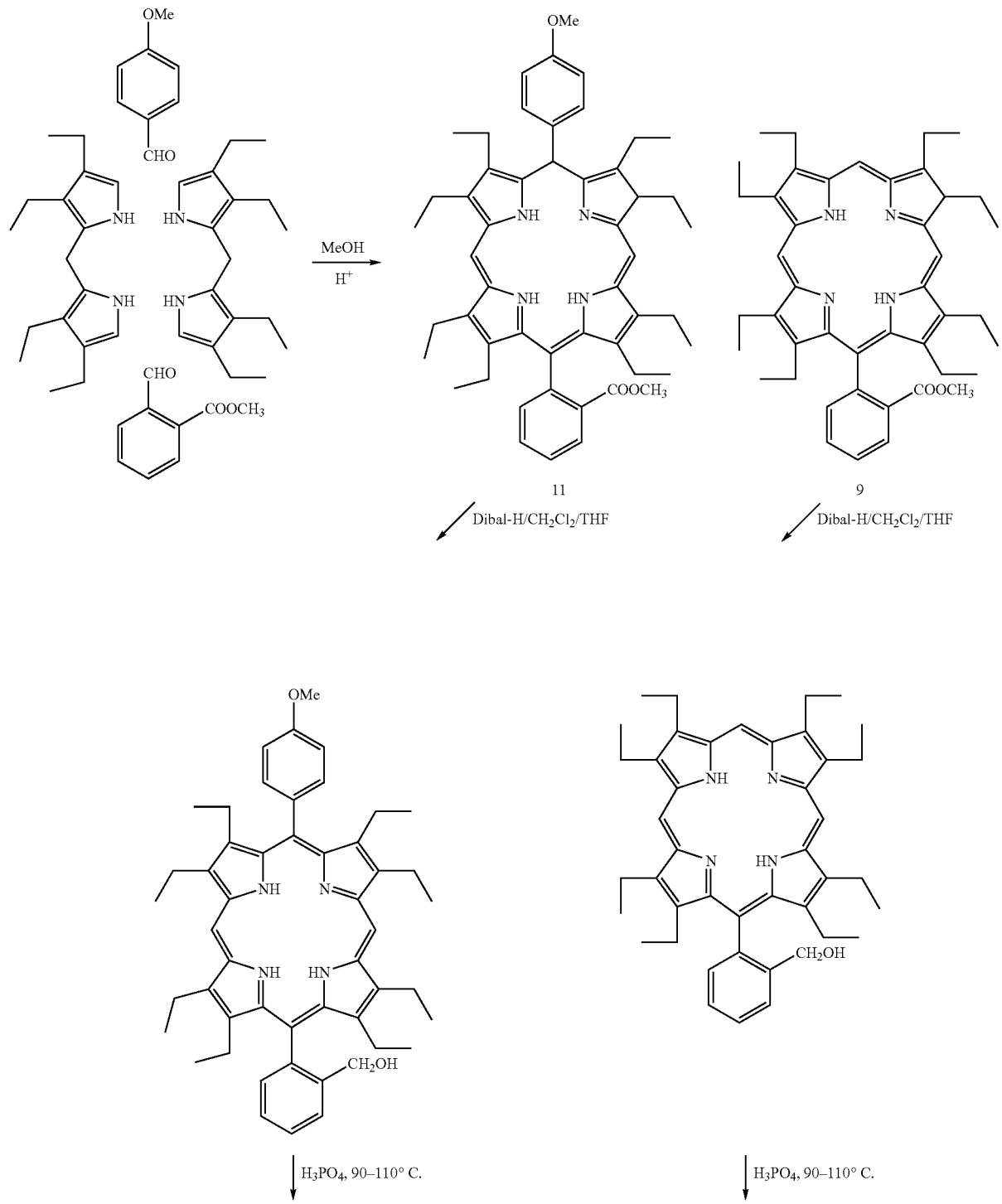
Scheme 6

-continued

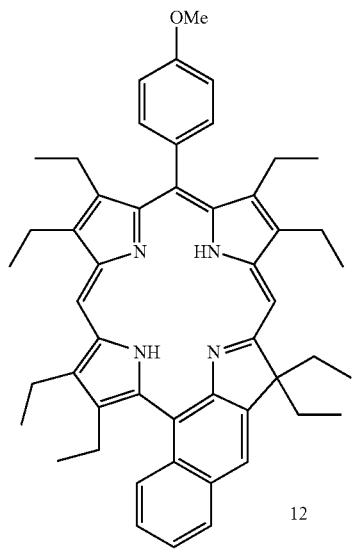

12

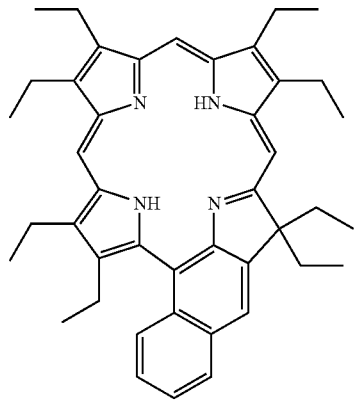

10

In yet another aspect of the invention, 5, 15-diaryl porphyrins such as 11 may be reduced to give the 15-aryl, 5-(2'-hydroxymethyl) porphyrin by DIBALD reduction in dichloromethane. Subsequent reaction of the 11 in $H_3PO_4$ at 90-110° C. produces the 15-aryl napthachlorin 12. This example of cyclizing 5, 15-aryl functionalized porphyrins lays the foundation for other aryl functionalized napthachlorins that may be synthesized from asymmetrical 5,15-diarylporphyrins.

In yet another aspect of the invention the synthesis of naphthochlorins from porphyrins bearing at least one (2'-cyano)phenyl group should be possible. Indeed, once the hydroxymethyl porphyrins have been synthesized, we have deomonstrated the cyclization is feasible. In addition to (2-hydroxymethyl)aryl porphyrins, those of ordinary skill in the art will recognize that the (2-hydroxymethyl) group on the aryl group may be modified prior to reaction with an acid, by reaction with, for example, toluene sulfonyl chloride or another modifying chemical. Such "analogues" may be isolated prior to acid treatment or formed in situ, and fall within the scope of the invention.

Synthesis of napthochlorins from Compounds such as meso-(2'-N,N,N-trialkylaminomethyl)phenyl porphyrins In yet another aspect of the invention, different synthetic routes to the synthesis of porphyrins bearing a "cyclizable" aromatic unit may be employed. Examples of these reactions are shown in Schemes 7a, 7b and 7c. In schemes 7a, 7b the well known MacDonald synthetic method may be utilized to produce the corresponding aromatic substituted porphyrins. In should be noted that the ortho substituent on the benzaldehyde (or protected benzaldehyde) may be any functional group capable of undergoing cyclization to produce the desired fused ring chlorins. Schemes 7a, 7b have been given as examples of MacDonald's synthetic method and should in no way be used to limit the scope of the invention. In Scheme 7a, an aromatic substituted dipyrromethane is formed via the condensation of two α-free pyrroles. In the scheme presented, both pyrroles bear an ester functionality. Dipyrromethanes with ester functionalities (e.g. 13) may be converted to the α-free dipyrromethane (e.g. 14) and to the diformyl dipyrromethanes (e.g. 15) via decarboxylation and formylation, or alternatively converted to the dihydroxymethyl dipyrromethane by reduction. Condensation of either the diformyl or dihydroxymethyl dipyrromethane with α-free dipyrromethanes, followed by oxidation yields the desired porphyrin bearing a "cyclizable" aromatic unit. In this instance the dialkylated amine on the aromatic ring system may be cyclized or converted to a dihydroxymethyl group (via the quaternary salt followed by base hydrolysis) and modified to cyclizable groups or converted. Alternatively, α-free dipyrromethanes (e.g. 14) may be coupled with formyl pyrroles to form biladienes or coupled with diformyl or dihydroxymethyl dipyrromethanes to give porphyrins. These porphyrins may then be cyclized to produce the desired napthochlorin or fused ring chlorin of choice. The coupling of such dipyrromethanes is well recognized in the literature (see for example; John Paine in "The Porphyrins" Ed. D. Dolphin, Vol. 1, Part A Chapter 4, p101-234, Academic Press, 1978).

Alternatively, utilizing the chemistry shown in scheme 7a, the dipyrromethane bearing the "cyclizable" aromatic unit may be converted to the α-free dipyrromethane and then cyclized with a second diformyl or dihydroxymethyl dipyrromethane to give the desired porphyrin (Scheme 7b). Alternatively, the diformyldipyrromethanes may be reacted with dipyrromethanes bearing aromatic substituents (for example 20) to give the desired 5, 15 substituted porphyrins. As another alternative, halogenated porphyrin as shown in scheme 7c may be reacted with organic zinc complexes in the presence of palladium to give the corresponding aryl substituted porphyrins.

The scope of the invention is not limited to the examples described herein. For example, utilizing this chemistry one may make modifications to the pyrroles, dipyrromethanes and aromatic aldehydes. Such modifications may be used to produce an array of molecules possessing different functionalities and different fused ring systems.

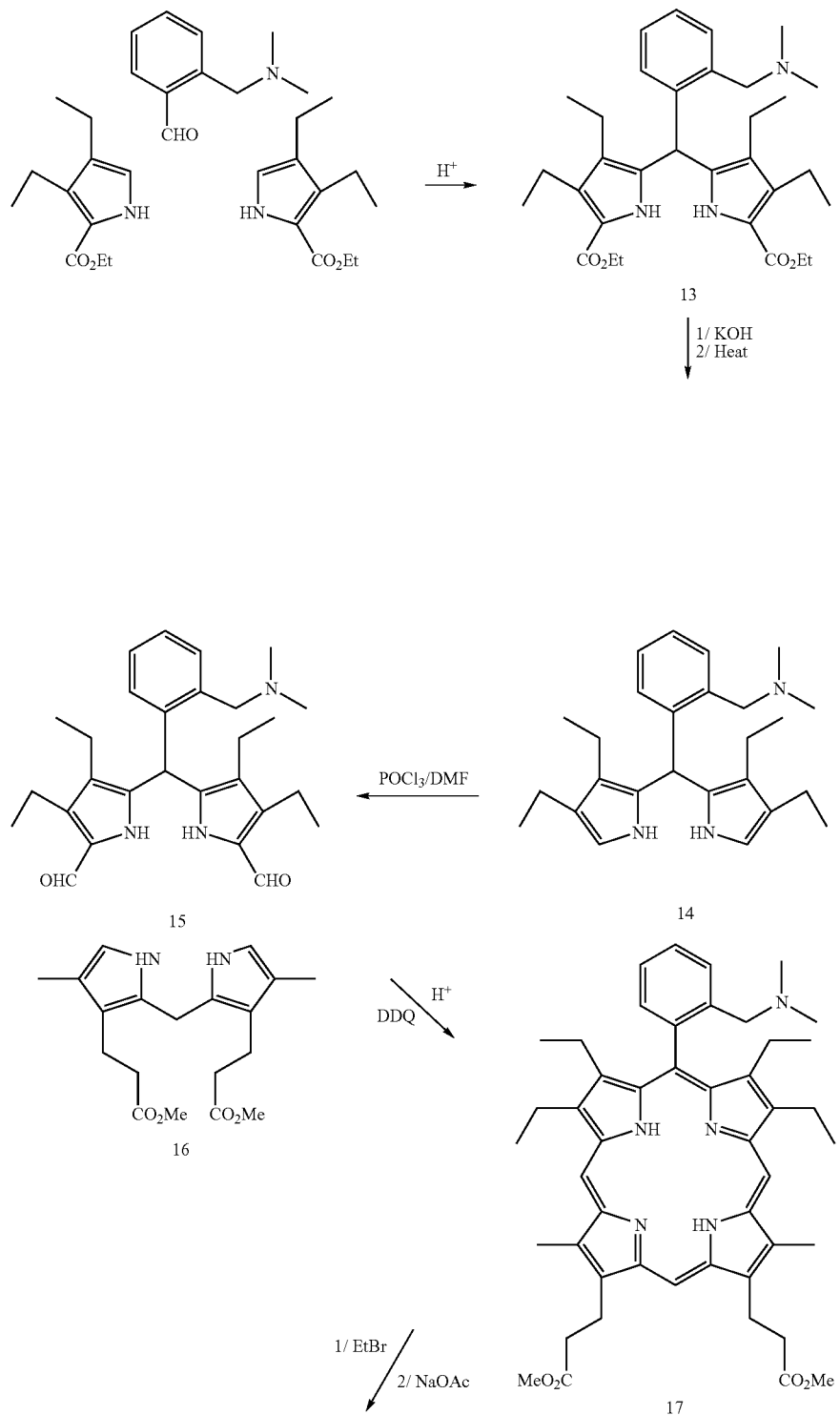

-continued
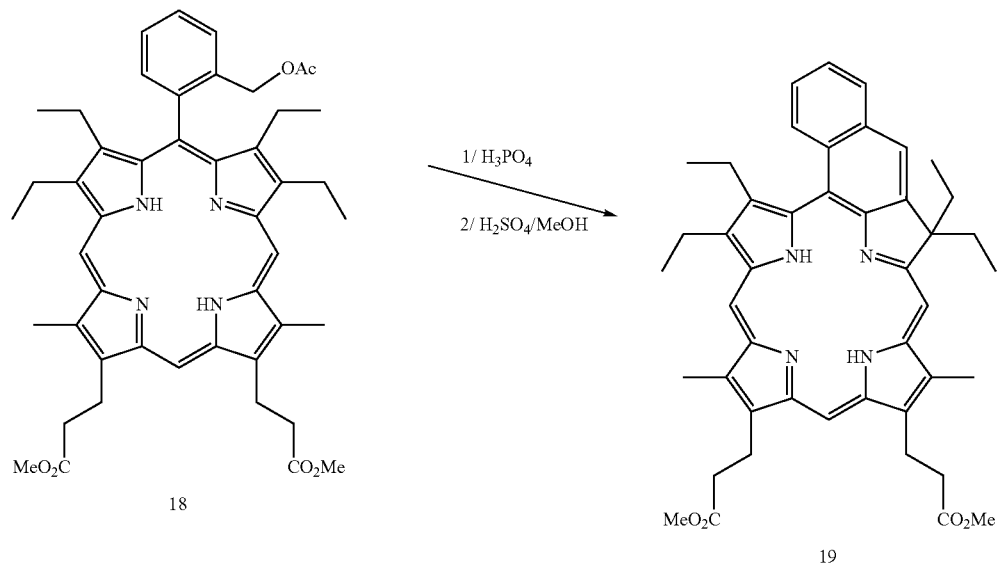
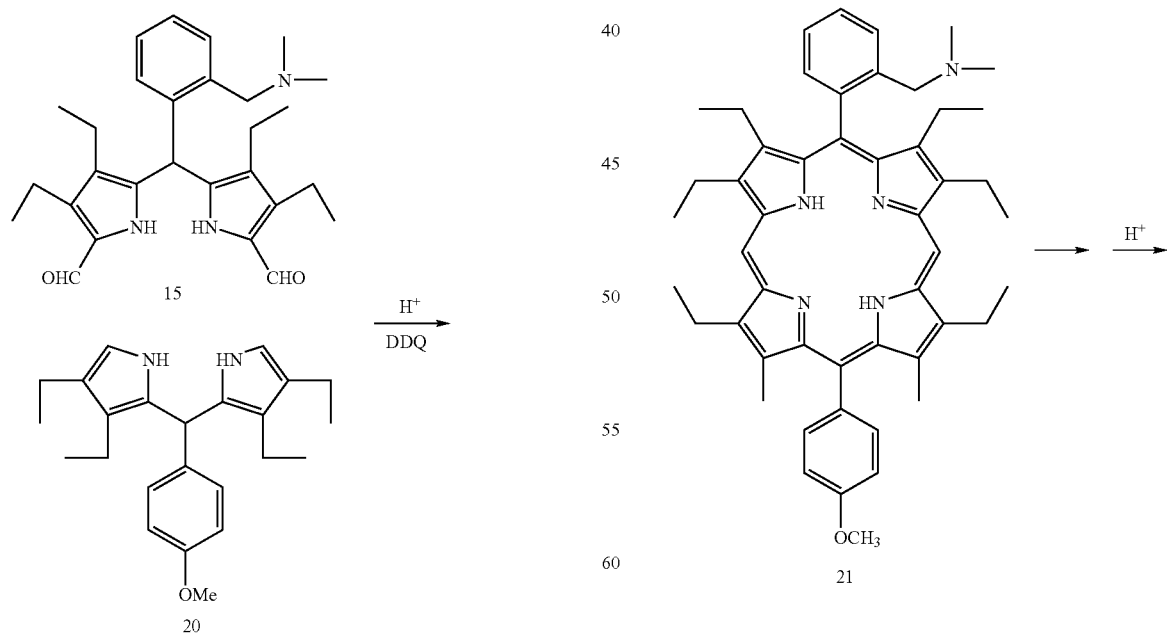

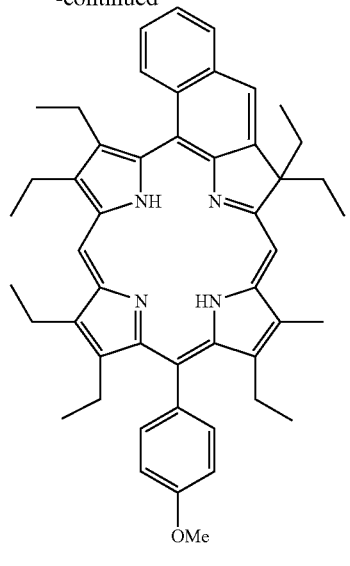

12

Scheme 7c

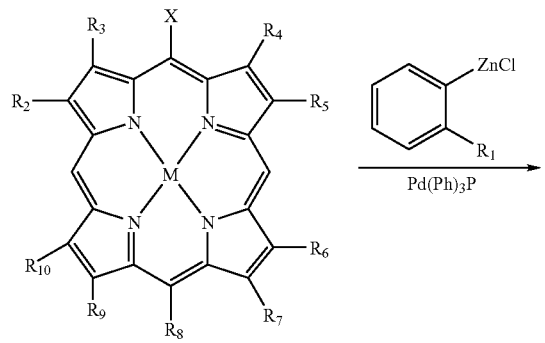

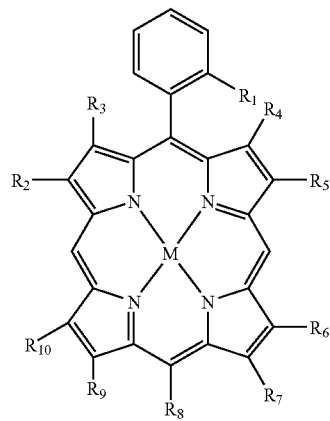

Because compounds such as meso-(2-methoxycarbonyl) phenyl porphyrins and meso-(2-(N,N,N-trialkylaminomethyl) porphyins can be synthesized and can be modified to give napthochlorins, one may substitute heteroatoms such as nitrogen into one or more positions in the phenyl rings (posi tions B, C, D, E) of the porphyrin precursors and form napthochlorins as shown in scheme 8 below.

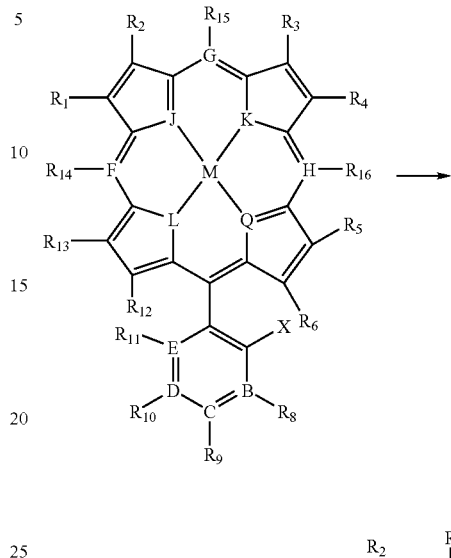

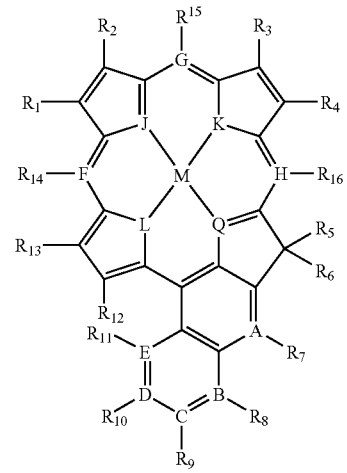

Furthermore, porphyrins bearing one or more heteroatoms such as nitrogen at positions F, G and H may be synthesized and cyclized according to the invention to give the corresponding napthochlorins. Alternatively, porphyrins bearing one or more heteroatoms in positions B, C, D, E, F, G, H may be synthesized and cyclized accordingly to give the corresponding napthochlorin. In addition to these combinations, it is possible to synthesize porphyrins with heteroatoms such as S, O, Te, Se in one or more of the positions J, K, L, Q shown in scheme 8. Such compounds may also be cyclized according to the invention to give the corresponding napthochlorins.

B) Anthrachlorins, benzanthachlorins and Chlorins with Fused Ring Systems (Formulae II, III, IV, and V)

In addition to naphthochorins, using the same or similar chemistry as outlined in section A), one may cyclize other aromatic ring systems that possess a group such as a 2'-hydroxymethyl group, (for example a (2'-hydroxymethyl)naphthyl group) or a 2-(N,N,N-trialkylaminomethyl) group according to the invention. Such cyclization produces compounds of formulae II, III, IV, and V. The following illustrates examples of chlorins with fused ring systems that fall within the scope of the invention.

The invention also includes compounds of formulae IIA, IIB, IIIA, IIIB, IVA, and IVB as shown below:

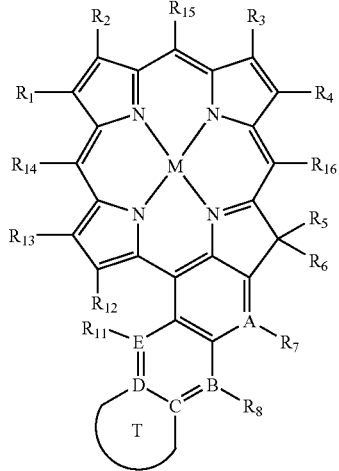
IIA

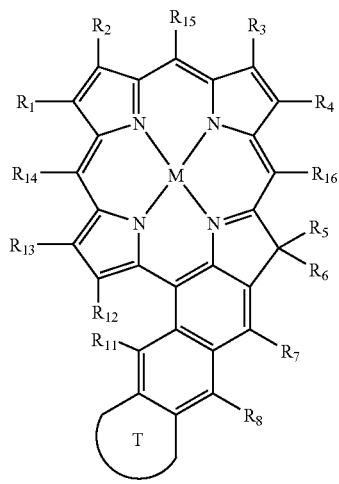
IIB

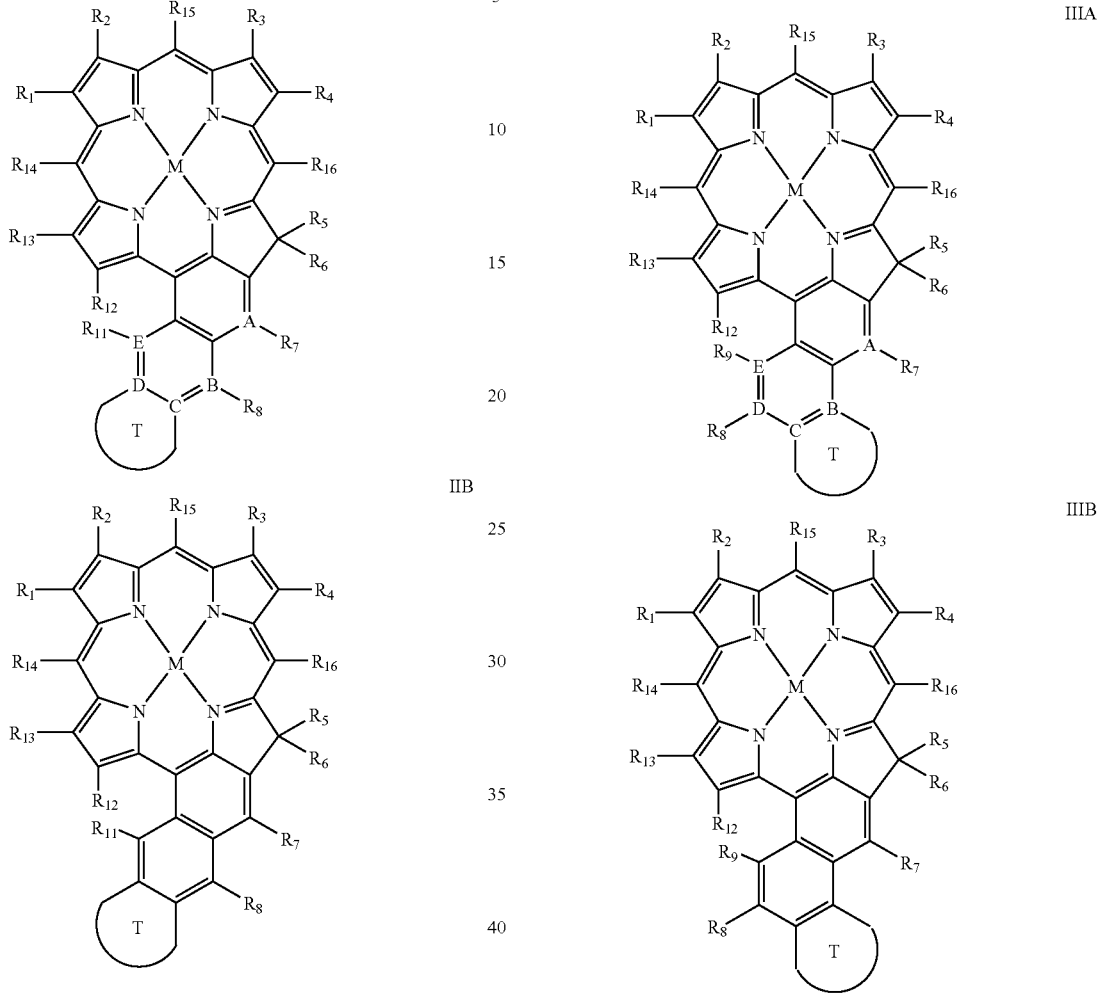
IIIA

IIIB wherein:

$R_1$, $R_2$, $R_3$, $R_4$, $R_5$, $R_6$, $R_7$, $R_8$, $R_{11}$, $R_{12}$, $R_{13}$, $R_{14}$, $R_{15}$, and $R_{16}$ are independently selected from hydrogen; halogen; unsubstituted or substituted alkyl containing 0 or more carbon atoms, $C_3$-$C_6$ cycloalkyl, acetyl, aryl, alkenyl, alkynyl, amide groups, or ester groups; $NR_{17}R_{18}$; vinyl; $N(R_{17})(R_{18})(R_{19})^+Z^-$; $CH=CHNR_{17}R_{18}$; $CH_2CH_2NR_{17}R_{18}$; $CH=CHN(R_{17})(R_{18})(R_{19})^+Z^-$; $CH_2CH_2N(R_{17})(R_{18})(R_{19})^+Z^-$; $CHOHCH_3$; $CHOR_{17}CH_3$; CN; OH; $OR_{17}$; CHO; $CH=CHCO_2R_{17}$; $(CH_2)_nOH$; $(CH_2)_nSH$; $(CH_2)_nO$-alkoxy; $(CH_2)_nSR_{17}$; $(CH_2)_nOR_{17}$; $(CH_2)_nCO_2R_{17}$; $(CH_2)_nCONHR_{17}$; $(CH_2)_nCON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+Z^-$;

$Z^-$ is a physiologically acceptable ion;

$R_{17}$, $R_{18}$, and $R_{19}$ are independently selected from hydrogen; a physiologically acceptable ion; unsubstituted or substituted $C_1$-$C_6$ alkyl, aryl, alkenyl, or alkynyl; and a functional group having a molecular weight less than about 100,000 daltons;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr;

T is selected from a substituted or unsubstituted aromatic, heteroaromatic, polyaromatic, polyheteroaromatic, cycloalkyl, and a heterocycloalkyl group.

wherein:

$R_1$, $R_2$, $R_3$, $R_4$, $R_5$, $R_6$, $R_7$, $R_8$, $R_9$, $R_{12}$, $R_{13}$, $R_{14}$, $R_{15}$, and $R_{16}$ are independently selected from hydrogen; halogen; unsubstituted or substituted alkyl, $C_3$-$C_6$ cycloalkyl, acetyl, aryl, alkenyl, alkynyl, amide groups or ester groups; $NR_{17}R_{18}$, vinyl; $N(R_{17})(R_{18})(R_{19})^+Z^-$; $CH=CHNR_{17}R_{18}$; $CH_2CH_2NR_{17}R_{18}$; $CH=CHN(R_{17})(R_{18})(R_{19})^+Z$; $CH_2CH_2N(R_{17})(R_{18})(R_{19})^+Z^-$; $CHOHCH_3$; $CHOR_{17}CH_3$; CN; OH; $OR_{17}$; CHO; $CH=CHCO_2R_{17}$; $(CH_2)_nOH$; $(CH_2)_nSH$; $(CH_2)_nO$-alkoxy; $(CH_2)_nSR_{17}$; $(CH_2)_nOR_{17}$; $(CH_2)_nCO_2R_{17}$; $(CH_2)_nCONHR_{17}$; $(CH_2)_nCON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+Z^-$;

$R_{17}$, $R_{18}$, and $R_{19}$, are independently selected from hydrogen; a physiologically acceptable ion; unsubstituted or substituted $C_1$-$C_6$ alkyl, aryl, alkenyl, or alkynyl; and a functional group having a molecular weight less than about 100,000 daltons;

$Z^-$ is a charge balancing ion;

n is an integer ranging from 1 to 4;

A, B, C, D, and E are independently selected from carbon, nitrogen, $N^+(R_{20})$ $Z^-$, oxygen, $Se^+$, and $Te^+$; $R_{20}$ is alkyl or aryl;

$Z'^-$ is a charge balancing ion;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr; and T is selected from a substituted or unsubstituted aromatic, heteroaromatic, polyaromatic, polyheteroaromatic, cycloalkyl, and a heterocycloalkyl group.

IVA

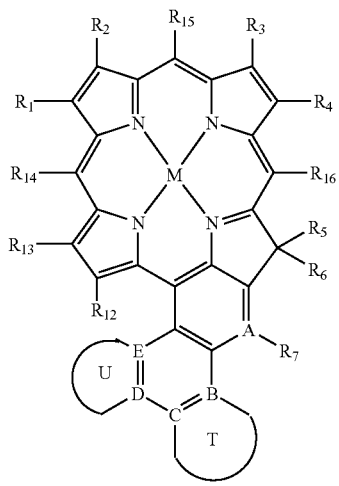

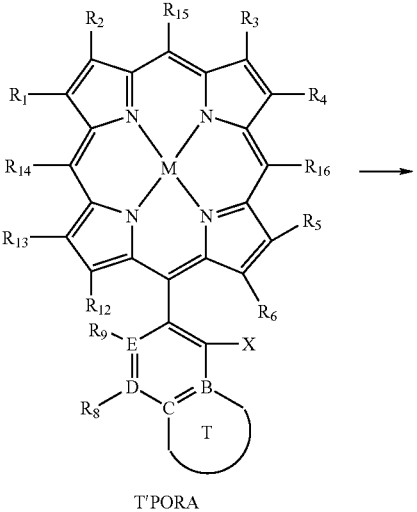

T'PORA

IVB

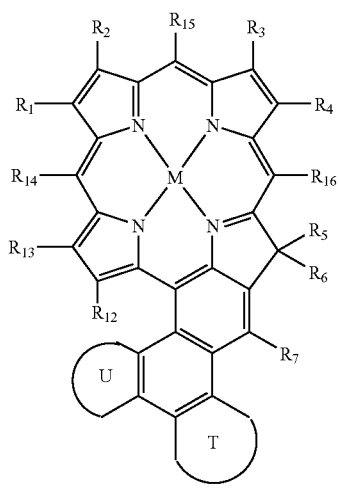

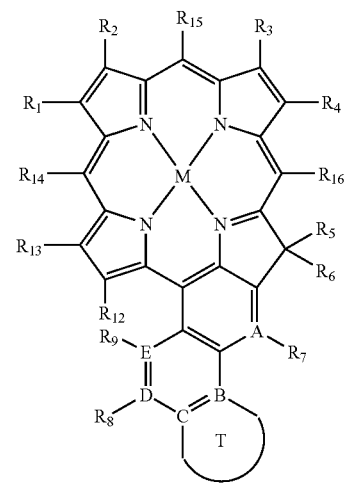

IIIA where $R_1$, $R_2$, $R_3$, $R_4$, $R_5$, $R_6$, $R_7$, $R_{12}$, $R_{13}$, $R_{14}$, $R_{15}$, T, and U are as defined as in formula III.

The scope of the invention is not limited to the examples shown. A large number of porphyrins are known in the literature (for example see "Porphyrins and Metalloporphyrins" ed. K. Smith, Elsevier, 1975, N.Y. and "The Porphyrins", Ed. D. Dolphin, Vol I-V, Academic Press, 1978) which contain various and ranging substituents on the β-pyrrole positions or meso-positions of the porphyrin ring (azoporphyrins, benzoporphyrins, tetraphenylporphyrins for example), either symmetrically or asymmetrically substituted on the ring.

The invention also includes the processes for synthesizing fused chlorin ring systems. Accordingly, the following reactions are within the scope of the invention:

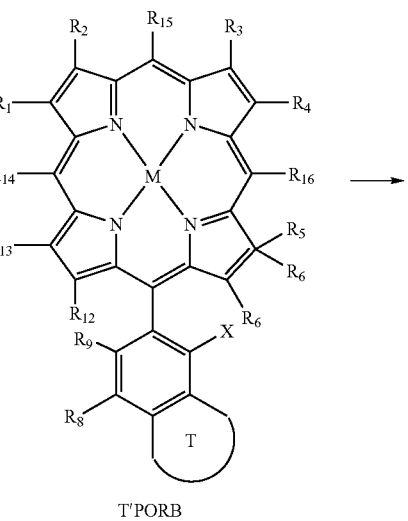

T'PORB

-continued
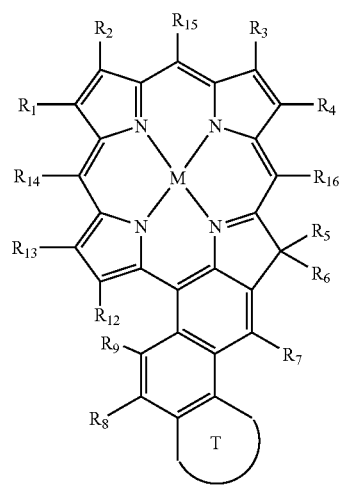
IIIB
Scheme 9 describes methods that may be used to synthesize various chlorin fused ring systems.
Scheme 9
a)
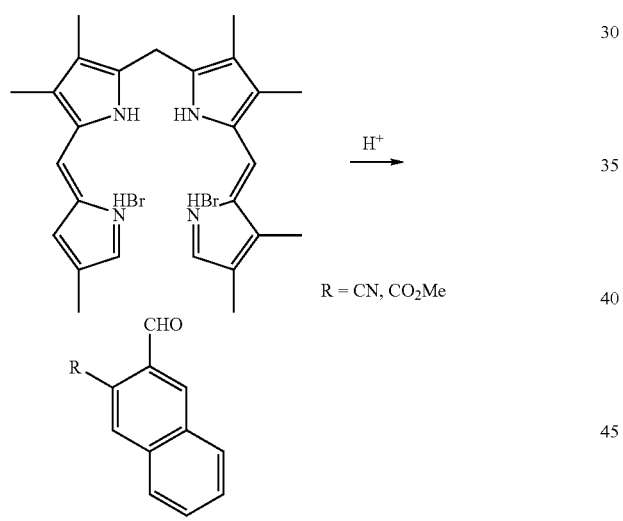
-continued
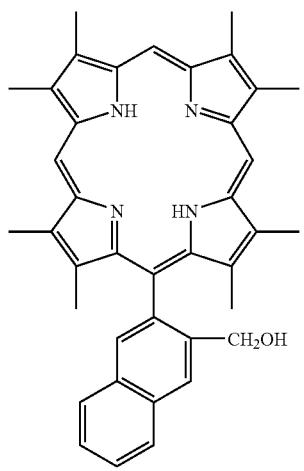
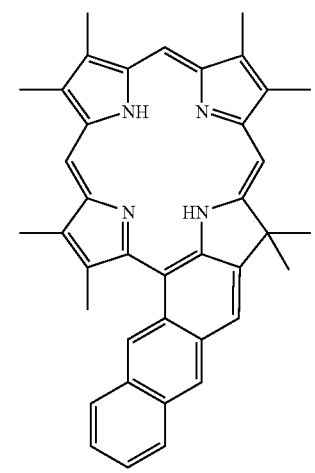
b)
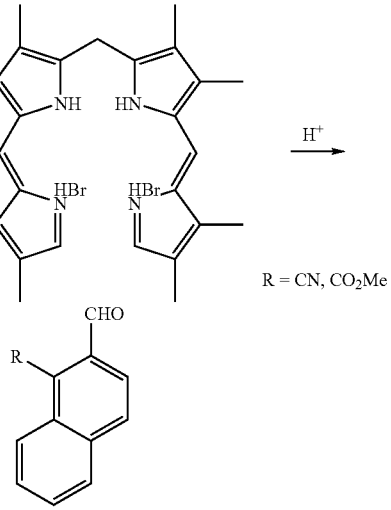
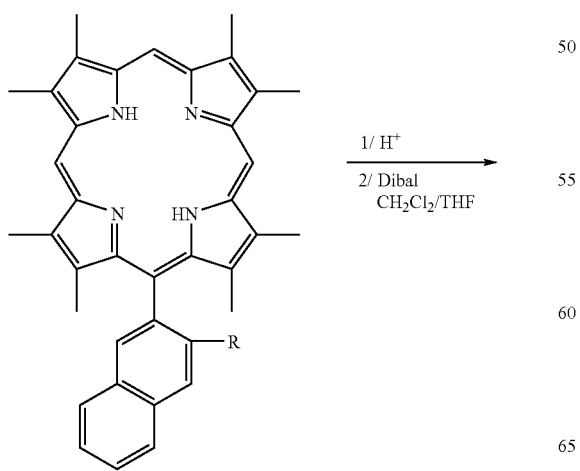

c)
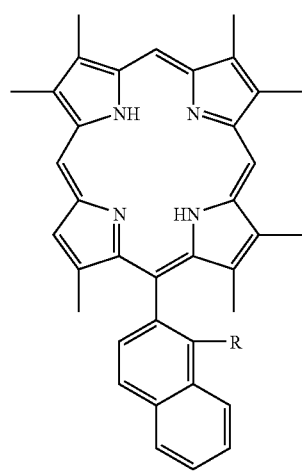
1/ H⁺
2/ Dibal
CH₂Cl₂/THF
→
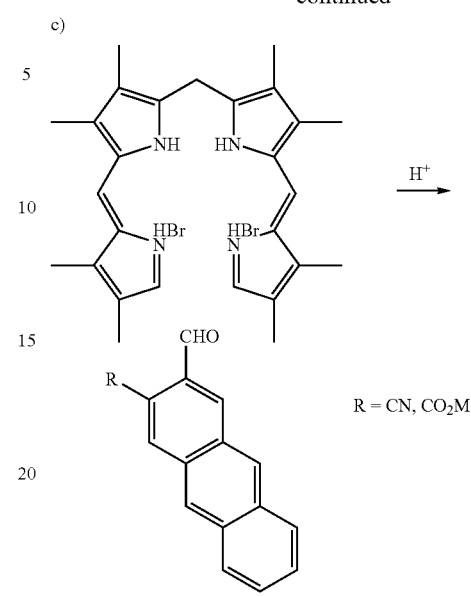
R = CN, CO₂Me
H⁺ →
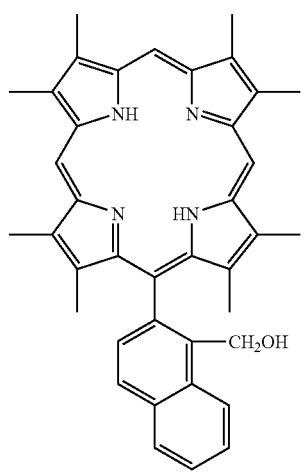
H⁺ →
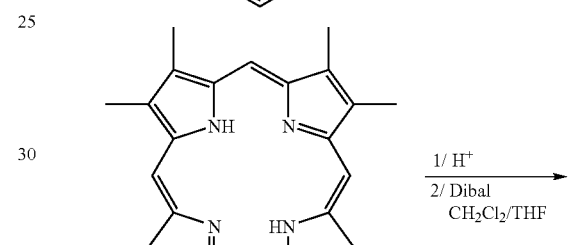
1/ H⁺
2/ Dibal
CH₂Cl₂/THF
→
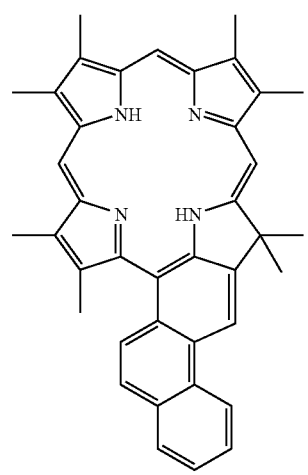
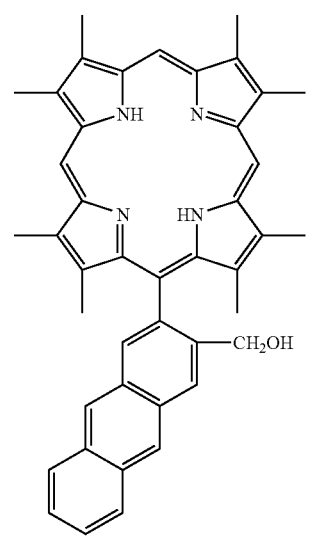
H⁺ →

-continued

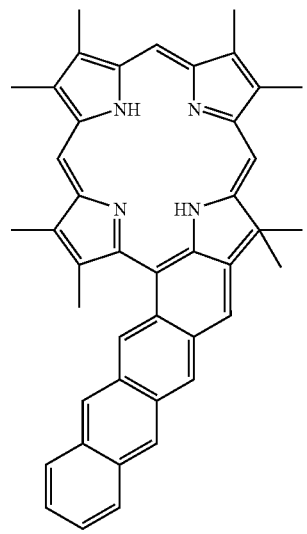

d)

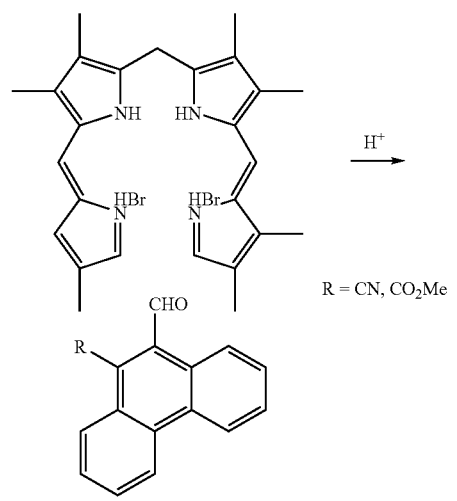

R = CN, CO₂Me

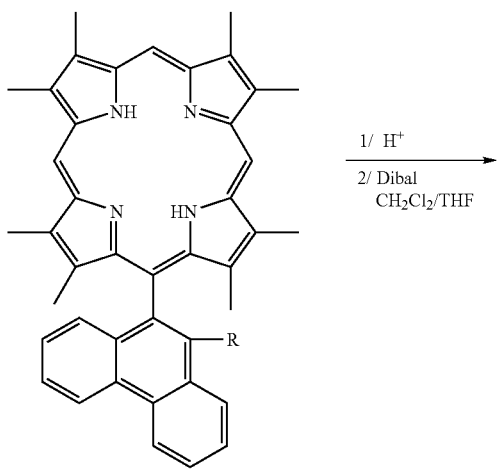

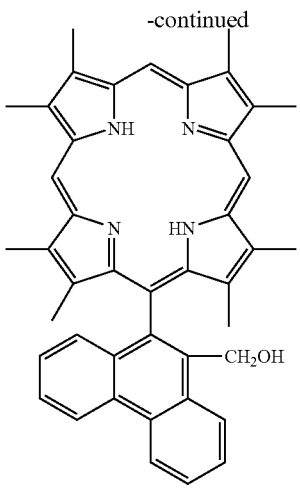

 H⁺ →

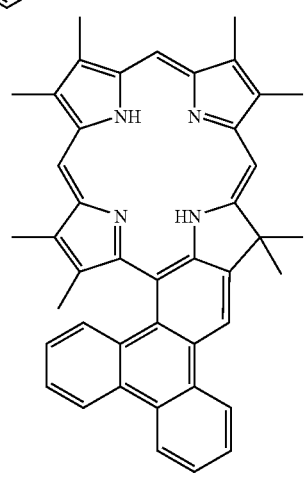

In addition to aromatic rings containing all carbon atoms, one may synthesize porphyrins bearing meso-(2'-methoxycarbonyl)aromatic groups or meso-(2'-(N,N,N,-trialkylaminomethyl) aromatic groups having hetero-atoms incorporated into the aromatic ring. Examples of such ring systems are shown below.

One or more of the carbon positions in the ring systems shown below may be substituted with hetero-atoms and may have other functionalities attached ($R_1$-$R_8$). Examples of such ring systems include napthalenes, anthracenes, benzopyrenes, quinolines, benzoquinolines, benzoperylene, benzofluorenes, fluorenes, benzofurazans, benzodiphenylenes, benzofluoranthenes, benzanthracenes, benzacephenanthrylenes, bathophenanthrolines, indans, benzoquinolines, quinolines, pyrazines, quinolines, quinazoles, quinoxalines, imidazopyridines, indenes, indolines, thiazolines, bezopyrimidines, pyrimidines, benzimidazole, triazolopyrimidines, pyrazoles, tryptophans, phenanthrolines, benzooxadiazoles, benzoselenadiazole, benzocoumarins, chalcones, fluoranthenes, pyridoindoles, pentacenes, perylenes, phenatholines, phenazines, phenoxazines, phenoxathiins, phenothiazines. Porphyrins bearing such ring functionalities may then be cyclized according to the invention to give the corresponding anthrachlorins, benzanthrachlorins or aromatic ring fused chlorins. In addition to these combinations, it is possible to synthesize porphyrins which possess heteroatoms such as S, O, Te or Se in the central porphyrin ring system (e.g thiaporphyrins). Such compounds may also be cyclized according to the invention to give the corresponding fused ring chlorins.

In addition to (2-hydroxymethyl)aryl porphyrins, those of ordinary skill in the art that would recognize that the (2-hydroxymethyl) group on the aryl group may be modified prior to reaction with an acid, by reaction with, for example, toluene sulfonyl chloride or another modifying chemical. Such "analogs" may be isolated prior to acid treatment or formed and fall within the scope of the invention.

DEFINITIONS

As used in the present application, the following definitions apply.

The term "alkyl" as used herein refers to substituted or unsubstituted, straight or branched chain groups, preferably having one to eight, more preferably having one to six, and most preferably having from one to four carbon atoms. The term "$C_1$-$C_6$ alkyl" represents a straight or branched alkyl chain having from one to six carbon atoms. Exemplary $C_1$-$C_6$ alkyl groups include methyl, ethyl, n-propyl, isopropyl, butyl, isobutyl, sec-butyl, t-butyl, pentyl, neo-pentyl, hexyl, isohexyl, and the like. The term "$C_1$-$C_6$ alkyl" includes within its definition the term "$C_1$-$C_4$ alkyl."

As applicants use the term, herein "an alkyl group containing 0 or more carbon atoms" includes the situation where the ring atoms of an aromatic ring system may be selected from atoms including, but not limited to, carbon and nitrogen. When carbon is selected, this definition includes, but is not limited to, radicals such as methyl, ethyl, and propyl. When the ring atom is nitrogen, however, the ring nitrogen contains an electron loan pair. Thus, as applicants use the term herein, the nitrogen contains an alkyl group containing 0 carbon atoms. Other circumstances where this definition may be appropriate will be well understood and recognized by those of ordinary skill in the art.

The term "cycloalkyl" refers to a substituted or unsubstituted, saturated or partially saturated, mono- or poly-carbocyclic ring, preferably having 5-14 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. An exemplary cycloalkyl is a $C_5$-$C_7$ cycloalkyl, which is a saturated hydrocarbon ring structure containing from five to seven carbon atoms.

The term "aryl" as used herein refers to an aromatic, monovalent monocyclic, bicyclic, or tricyclic radical containing 6, 10, 14, or 18 carbon ring atoms, which may be unsubstituted or substituted, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, napthyl, anthryl, phenanthryl, fluoren-2-yl, indan-5-yl, and the like.

The term "halogen" represents chlorine, fluorine, bromine or iodine. The term "halocarbon" represents a halogen bonded to a carbon bearing group.

The term "carbocycle" represents a substituted or unsubstituted aromatic or a saturated or a partially saturated 5-14 membered monocyclic or polycyclic ring, such as a 5- to 7-membered monocyclic or 7- to 10-membered bicyclic ring, wherein all the ring members are carbon atoms.

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulfur, wherein the radical is unsubstituted or substituted, and to which may be fused one or more cycloalkyl groups, aryl groups, or heteroaryl groups, which themselves may be unsubstituted or substituted. Illustrative examples of heterocycloalkyl groups include, but are not limited to azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like.

A "heteroaryl group" is intended to mean an aromatic monovalent monocyclic, bicyclic, or tricyclic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, which may be unsubstituted or substituted, and to which may be fused one or more cycloalkyl groups, heterocycloalkyl groups, or aryl groups, which themselves may be unsubstituted or substituted. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

The term "leaving group" as used herein refers to any group that departs from a molecule in a substitution reaction by breakage of a bond. Examples of leaving groups include, but are not limited to, halides, arenesulfonates, alkylsulfonates, and triflates.

Suitable protecting groups are recognizable to those skilled in the art. Examples of suitable protecting groups can be found in T. Green & P. Wuts, *Protective Groups in Organic Synthesis* (2d ed. 1991), which is incorporated herein by reference in its entirety.

Suitable salt ions include, but are not limited to, inorganics such as halogens, pseudohalogens, sulfates, hydrogen sulfates, nitrates, hydroxides, phosphates, hydrogen phosphates, dihydrogen phosphates, perchlorates, and related complex inorganic ions; and organics such as carboxylates, sulfonates, bicarbonates and carbonates.

Examples of substituents for alkyl and aryl groups include mercapto, thioether, nitro ($NO_2$), amino, aryloxyl, halogen, hydroxyl, alkoxyl, and acyl, as well as aryl, cycloalkyl and saturated and partially saturated heterocycles. Examples of substituents for cycloalkyl groups include those listed above for alkyl and aryl, as well as aryl and alkyl.

Exemplary substituted aryls include a phenyl or naphthyl ring substituted with one or more substituents, preferably one to three substituents, independently selected from halo, hydroxy, morpholino($C_1$-$C_4$)alkoxy carbonyl, pyridyl ($C_1$-$C_4$)alkoxycarbonyl, halo ($C_1$-$C_4$)alkyl, $C_1$-$C_4$ alkyl, $C_1$-$C_4$ alkoxy, carboxy, $C_1$-$C_4$ alkocarbonyl, carbamoyl, N—($C_1$-$C_4$)alkylcarbamoyl, amino, $C_1$-$C_4$alkylamino, di($C_1$-$C_4$) alkylamino or a group of the formula —$(CH_2)_a$—$R_7$ where a is 1, 2, 3 or 4; and $R_7$ is hydroxy, $C_1$-$C_4$ alkoxy, carboxy, $C_1$-$C_4$ alkoxycarbonyl, amino, carbamoyl, $C_1$-$C_4$ alkylamino or di($C_1$-$C_4$)alkylamino.

Another substituted alkyl is halo($C_1$-$C_4$)alkyl, which represents a straight or branched alkyl chain having from one to four carbon atoms with 1-3 halogen atoms attached to it. Exemplary halo($C_1$-$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, and the like.

Another substituted alkyl is hydroxy ($C_1$-$C_4$)alkyl, which represents a straight or branched alkyl chain having from one to four carbon atoms with a hydroxy group attached to it. Exemplary hydroxy($C_1$-$C_4$)alkyl groups include hydroxymethyl, 2-hydroxyethyl, 3-hydroxypropyl, 2-hydroxyisopropyl, 4-hydroxybutyl, and the like.

Yet another substituted alkyl is $C_1$-$C_4$ alkylthio($C_1$-$C_4$) alkyl, which is a straight or branched $C_1$-$C_4$ alkyl group with a $C_1$-$C_4$ alkylthio group attached to it. Exemplary $C_1$-$C_4$ alkylthio($C_1$-$C_4$)alkyl groups include methylthiomethyl, ethylthiomethyl, propylthiopropyl, sec-butylthiomethyl, and the like.

Yet another exemplary substituted alkyl is heterocycle($C_1$-$C_4$)alkyl, which is a straight or branched alkyl chain having from one to four carbon atoms with a heterocycle attached to it. Exemplary heterocycle($C_1$-$C_4$)alkyls include pyrrolylmethyl, quinolinylmethyl, 1-indolylethyl, 2-furylethyl, 3-thien-2-ylpropyl, 1-imidazolylisopropyl, 4-thiazolylbutyl and the like.

Yet another substituted alkyl is aryl($C_1$-$C_4$)alkyl, which is a straight or branched alkyl chain having from one to four carbon atoms with an aryl group attached to it. Exemplary aryl($C_1$-$C_4$)alkyl groups include phenylmethyl, 2-phenylethyl, 3-naphthyl-propyl, 1-naphthylisopropyl, 4-phenylbutyl and the like.

The heterocycloalkyls and the heteroaryls can, for example, be substituted with 1,2 or 3 substituents independently selected from halo, halo($C_1$-$C_4$)alkyl, $C_1$-$C_4$ alkyl, $C_1$-$C_4$ alkoxy, carboxy, $C_1$-$C_4$ alkoxycarbonyl, carbamoyl, —($C_1$-$C_4$)alkylcarbamoyl, amino, $C_1$-$C_4$alkylamino, di($C_1$-$C_4$)alkylamino or a group having the structure —$(CH_2)_a$—$R^7$ where a is 1, 2, 3 or 4 and $R^7$ is hydroxy, $C_1$-$C_4$ alkoxy, carboxy, $C_1$-$C_4$ alkoxycarbonyl, amino, carbamoyl, $C_1$-$C_4$alkylamino or di($C_1$-$C_4$)alkylamino.

Examples of substituted heterocycloalkyls include, but are not limited to, 3-N-t-butyl carboxamide decahydroisoquinolinyl and 6-N-t-butyl carboxamide octahydro-thieno[3,2-c]pyridinyl. Examples of substituted heteroaryls include, but are not limited to, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

A "pharmaceutically acceptable solvate" is intended to mean a solvate that retains the biological effectiveness and properties of the biologically active components of the inventive compounds.

Examples of pharmaceutically acceptable solvates include, but are not limited to, compounds prepared using water, isopropanol, ethanol, methanol, DMSO, ethyl acetate, acetic acid, or ethanolamine.

In the case of solid formulations, it is understood that the compounds of the invention may exist in different forms, such as stable and metastable crystalline forms and isotropic and amorphous forms, all of which are intended to be within the scope of the present invention.

A "pharmaceutically acceptable salt" is intended to mean those salts that retain the biological effectiveness and properties of the free acids and bases and that are not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, hydroxybutyrates, glycolates, tartrates, methanesulfoantes, propanesulfonates, naphthalene-1-sulfonates, naphthalene-2-sulfonates, and mandelates.

A "pharmaceutically acceptable ion" is intended to mean those ions that may be used to form pharmaceutically acceptable salts.

Pharmaceutically acceptable ions include, but are not limited to, sodiium and potassium.

If a compound of the present invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hyrodoxy acids such as citric acid and tartaric acid, amino acids such as aspartic acid and glutamic acid, aromatic acids such as benzoic acid and cinnamic acid, sulfonic acids such as p-toluenesulfonic acid or ethanesulfonic acid, or the like.

If a compound of an inventive method of the present invention is an acid, the desired salt may be prepared by any suitable method known to the art, including treatment of the free acid with an inorganic or organic base, such as an amine (primary, secondary or tertiary), or an alkali metal or alkaline earth metal hydroxide or the like. Illustrative examples of suitable salts include organic salts derived from amino acids such as glycine and arginine; ammonia; primary, secondary and tertiary amines; cyclic amines such as piperidine, morpholine and piperazine; and inorganic salts derived from sodium, calcium, potassium, magnesium, manganese, iron, copper, zinc, aluminum, and lithium.

Functional groups falling within the scope of the invention having a molecular weight less than about 100,000 daltons include:

(1) hydrogen; (2) halogen, such as fluoro, chloro, iodo and bromo; (3) lower alkyl, such as methyl, ethyl, n-propyl, isopropyl, t-butyl, n-pentyl and the like groups; (4) lower alkoxy, such as methoxy, ethoxy, isopropoxy, n-butoxy, t-entoxy and the like; (5) hydroxy, alkylhydroxy, alkylethers; (6) carboxylic acid or acid salts, such as —$CH_2COOH$, —$CH_2COO^-Na^+$, —$CH_2CH_2COOH$, —$CH_2CH_2COONa$, —$CH_2CH_2CH(Br)COOH$, —$CH_2CH_2CH(CH_3)COOH$, —$CH_2CH(Br)COOH$ —$CH_2CH(CH_3)COOH$, —$CH(Cl)$—$CH_2$—$CH(CH_3)$—$COOH$, —$CH_2$—$CH_2$—$C(CH_3)_2$—$COOH$, —$CH_2$—$CH_2$—$C(CH_3)_2$—$COO^-K^+$, —$CH_2$—$CH_2$—$CH_2$—$COOH$, $C(CH_3)_3$—$COOH$, $CH(Cl)_2COOH$ and the like; (7) carboxylic acid esters, such as —$CH_2CH_2COOCH_3$, —$CH_2CH_2COOCH_2CH_3$, —$CH_2CH(CH_3)COOCH_2CH_3$, —$CH_2CH_2CH_2COOCH_2CH_2CH_3$, —$CH_2CH(CH_3)_2COOCH_2CH_3$, and the like; (8) sulfonic acid or acid salts, for example, group I and group 11 salts, ammonium salts, and organic cation salts such as alkyl and quaternary ammonium salts; (9) sulfonylamides such as substituted and unsubstituted benzene sulfonamides; (10) sulfonic acid esters, such as methyl sulfonate, ethyl sulfonate, cyclohexyl sulfonate and the like; (11) amino, such as unsubstituted primary amino, methylamino, ethylamino, n-propylamino, isopropylamino, 5-butylamino, sec-butylamino, dimethylamino, trimethylamino, diethylamino, triethylamino, di-n-propylamino, methylethylamino, dimethyl-sec-butylamino, 2-aminoethanoxy, ethylenediamino, 2-(N-methylamino) heptyl, cyclohexylamino, benzylamino, phenylethylamino, anilino, -methylanilino, N,N-dimethylanilino, N-methyl-N ethylanilino, 3, 5-dibromo4-anilino, p-toluidino, diphenylamino, 4,4'-dinitrodiphenylamino and the like; (12) cyano; (13) nitro; or (14) a biologically active group; or (15) any other substituent that increases the amphiphilic nature of the compounds shown in the compounds of the invention.

The term "biologically active group" can be any group that selectively promotes the accumulation, elimination, binding rate, or tightness of binding in a particular biological environment. For example, one category of biologically active groups is the substituents derived from sugars, specifically, (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, verbose, and tagatose; (3) pyranoses such as glucopyranose; (4) furanoses such as fructo-furanose; (5) O-acyl derivatives such as penta-O-acetyl-a-glucose; (6) O-methyl derivatives such as methyl a-glucoside, methyl p-glucoside, methyl a-glucopyranoside and methyl-2,3,4,6-tetra-O-methyl glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, o-gluconolactone, 5-glucuronolactone, ascorbic acid, and dehydroascorbic acid; (10) phosphoric acid esters such as a-glucose 1-phosphoric acid, a-glucose 6-phosphoric acid, a-fructose 1,6-diphosphoric acid, and a-fructose 6-phosphoric acid; (11) deoxy sugars such as 2-deoxy-ribose, rhammose (deoxymannose), and fructose (6-deoxy-galactose); (12) amino sugars such as glucosamine and galactosamine; muramic acid and neurarninic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as a-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyquanosine, 2'-deoxycytidine, and 2'-deoxythymidine.

Another category of biologically active groups that is particularly useful is any ligand that is specific for a particular biological receptor. The term "ligand specific for a receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; (4) neurotransmitters, such as acetylcholine, serotonin, dopamine, and the like; and (5) antibodies. Any analog of these substances that also succeeds in binding to a biological receptor is also included. Particularly useful examples of substituents tending to increase the amphiphilic nature of the compounds of formulae I-V include: (1) long chain alcohols, for example, —$C_{12}H_{24}$—OH where —$C_{12}H_{24}$ is hydrophobic; (2) fatty acids and their salts, such as the sodium salt of the long-chain fatty acid oleic acid; (3) phosphoglycerides, such as phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidal choline; (4) sphingolipids, such as sphingomyelin; and (5) glycolipids, such as glycosyidiacylglycerols, cerebrosides, sulfate esters of cerebrosides or gangliosides.

The compounds of the present invention can be administered to the host in a variety of forms adapted to the chosen route of administration, i.e., orally, intravenously, intramuscularly, subcutaneously or topically.

The active compound may be orally administered, for example, with an inert diluent or with an assimilable edible carrier, or it may be enclosed in hard or soft shell gelatin capsule, or it may be compressed into tablets, or it may be incorporated directly with food. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least about 0.1% of active compound.

The percentage of the compositions and preparations may, of course, be varied and may conveniently be between about 2 to about 60% of the weight of the administered product. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potatostarch, alginic acid and the like; a lubricant such as magnesium stearate; a sweetening agent such as sucrose, lactose or saccharin; or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulation.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions, dispersions, or liposomal or emulsion formulations. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required additional ingredients from those enumerated above. In the case of sterile powders for the preparation of sterile injectable solutions, the preferred methods of preparation are vacuum drying and the freeze-drying technique, which yield a powder of the active ingredient plus any additional desired ingredient from previously sterile-filtered solutions thereof.

The present new compounds may also be applied directly to tumors in the host whether internal or external, in topical compositions. Exemplary compositions include solutions of the new compounds in solvents, particularly aqueous solvents, most preferably water. Alternatively, for topical application particularly to skin tumors, the present new compounds may be dispersed in the usual cream or salve formulations commonly used for this purpose (such as liposomes, ointments, gels, hydrogels, and oils) or may be provided in the form of spray solutions or suspensions which may include a propellant usually employed in aerosol preparations.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifications for the novel dosage unit forms of the invention are dictated by and directly dependent on (a) the unique characteristics of the active material and the particular therapeutic effect to be achieved, and (b) the limitations inherent in the art of compounding such an active material for the treatment of tumors in living subjects.

The following examples are given to highlight some preferred modes of synthesizing naphthochlorin molecules and are not intended to limit the scope of the invention.

EXAMPLES

In the following examples silica gel 60 (230-400 mesh) was used for column chromatography. Analytical thin layer chromatography was performed on Merck 60F254 silica gel (precoated on aluminum). $^1$H spectra were recorded using a Unity Inova Varian 500 MHz or Bruker Avance 300 MHz spectrometer, chemical shifts of proton spectra are expressed in parts per million relative to the chloroform signal in deuterated chloroform (set at 7.24 ppm) or DMSO-$d_6$ (set at 2.5 ppm). Electronic spectra were recorded on a Beckman DU 640 spectrophotometer. High resolution mass spectra were obtained on a VG 70SE double focussing mass spectrometer equipped with an oversize data system.

Example 1

8,12-di(methoxycarbonylmethyl)-2,3,17,18-tetraethyl-7,13-dimethyl-20-(4',6'-dimethoxy-2'-methoxycarbonyl)phenyl porphyrin (1)

To a solution of biladiene (5) (500 mg, 0.67 mmol) and methyl 2-formyl-3,5-dimethoxy methylbenzoate (1.8 g, 8 mmol) in methanol (125 ml) was added 31% HBr (in acetic acid) (500 ml). The mixture was refluxed with stirring for 2 h 20 min., cooled to room temperature, poured into water (200 ml), basified with $NaHCO_3$ and extracted with methylene chloride (3×100 ml). The combined methylene chloride layer was washed with water (2×100 ml), dried ($Na_2SO_4$) and solvent removed. The residue was purified by flash column (silica; 10% acetone-hexane, then 3% acetone-methylene chloride) to get porphyrin (1), 345 mg (65%); $\lambda_{max}$ 407, 505, 539, 575, 628 nm; MS(FAB) m/z 789 (M+H$^+$); $^1$H NMR (500 MHz, CDCl$_3$) δ 10.11 (s, 2H, meso-H), 9.91 (s, 1H, meso-H), 7.44 (d, 1H, J=2.5 Hz, Ar—H), 6.98 (d, 1H, J=2.5 Hz), 5.04 (d, 2H, J=16 Hz, —CH$_2$—), 5.0 (d, 2H, J=16 Hz, —CH$_2$—), 4.15 (s, 3H, —COOCH$_3$), 3.97 (q, 4H, J=7.5 Hz, —CH$_2$—), 3.76 (s, 6H, —COOCH$_3$), 3.65 (s, 6H, pyrrole-CH$_3$), 3.54 (s, 3H, —OCH$_3$), 3.02 (m, 2H, —CH$_2$—), 2.75 (m, 2H, —CH$_2$—), 2.29 (s, 3H, —OCH$_3$), 1.82 (t, 6H, J=7 Hz, —CH$_3$), 1.11 (t, 6H, J=7.5 Hz, —CH$_3$), -2.86 (br, 1H, —NH), -2.98 (br, 1H, —NH).

Example 2

8,12-di(hydroxyethyl)-2,3,17,18-tetraethyl-7,13-dimethyl-20-(4',6'-dimethoxy-2'-hydroxymethyl)phenyl porphyrin (2)

A solution of porphyrin 1 (327 mg, 0.41 mmol) in anhydrous THF (tetrahydrofuran) (7 ml) was added (in drops) to a stirred slurry of LAH (129 mg, 3.4 mmol) in anhydrous THF (5 ml) at room temperature. Stirring was continued for 50 min. The excess LAH was decomposed by dropwise addition of 0.2N HCl in cold condition (ice-bath), diluted with water (50 ml) and extracted with methylene chloride (3×25 ml). The combined methylene chloride layer was washed with water (2×30 ml), dried ($Na_2SO_4$) and solvent removed to get the reduced product (2), 286 mg (98%); $\lambda_{max}$ 405, 504, 538, 573, 626 nm; MS(FAB) m/z 705 (M+H$^+$); $^1$H NMR (500 MHz, DMSO-$d_6$) δ 10.18 (s, 2H, meso-H), 10.11(s, 1H, meso-H), 7.16 (d, 1H, J=2.5 Hz, Ar—H), 6.92 (d, 1H, J=2.5 Hz, Ar—H), 5.19 (t, 2H, J=5 Hz, —CH$_2$), 4.9 (t, 1H, J=5.5 Hz, —OH), 4.24 (m, 8H, —CH$_2$—CH$_2$—), 4.07 (s, 3H, —OCH$_3$), 4.03 (q, 4H, J=7.5 Hz, —CH$_2$), 3.65 (s, 6H, pyrrole-CH$_3$), 3.57 (s, 3H, —OCH$_3$), 3.12 (m, 2H, —CH$_2$), 2.8 (m, 2H, —CH$_2$), 1.82 (t, 6H, J=7.5 Hz, —CH$_3$), 1.162 (t, 6H, J=7.5 Hz, —CH$_3$), -3.14 (s, 1H, —NH), -3.28 (s, 1H, —NH).

Example 3

Synthesis of Naphthochlorin (7)

A mixture of porphyrin (2) (178 mg, 0.2 mmol) and phosphoric acid (15 ml) was stirred and heated at 105-110° C. for 1 hour and 40 minutes. After cooling to room temperature the mixture was poured into water (50 ml), basified with 20% aqueous NaOH and extracted with pyridine:methylene chloride (40:60) (3×50 ml). The combined organic layer was washed with water (2×50 ml), dried ($Na_2SO_4$) and solvent removed. The residue was purified by flash column (silica; 3% methanol-methylene chloride, 5% methanol-methylene chloride, then 8% methanol-methylene chloride) to get naphthochlorin (7), 36 mg (21%); $\lambda_{max}$ 436, 549, 583, 627, 686 nm; MS(FAB) m/z 673 (M+H$^+$), $^1$H NMR (500 MHz, DMSO-$d_6$) δ 10.02 (s, 1H, Ar—OH), 9.29 (s, 1H, meso-H), 8.85 (s, 1H, meso-H), 8.30 (s, 1H, meso-H), 8.28 (s, 1H, Ar—H), 7.31 (d, 1H, J=2 Hz, Ar—H), 6.75 (d, 1H, J=2.5 Hz, Ar—H), 5.08 (t, 1H, J=5 Hz, —OH), 5.02 (t, 1H, J=5.5 Hz, —OH), 4.06 (m, 2H, —$CH_2$—), 3.97 (m, 2H, —$CH_2$—), 3.82 (m, 4H, —$CH_2$—$CH_2$—), 3.71 (s, 3H, —$OCH_3$), 3.62-3.53 (m, 2H, —$CH_2$), 3.42 (m, 1H, —$CH_2$), 3.19 (s, 3H, pyrrole-$CH_3$), 3.16 (s, 3H, pyrrole-$CH_3$), 2.19 (m, 2H, —$CH_2$), 2.66 (m, 2H, —$CH_2$), 2.56 (m, 1H, —$CH_2$), 1.53 (t, 3H, J=8 Hz, —$CH_3$), 0.39 (t, 3H, J=7.5 Hz, —$CH_3$), 0.094 (t, 3H, J=7.5 Hz, —$CH_3$), -0.08 (t, 3H, J=7.5 Hz, —$CH_3$).

Example 4

8,12-di(methoxycarbonylethyl)-2,3,17,18-tetraethyl-7,13-dimethyl-20-(2'-methoxycarbonyl)phenyl porphyrin (3)

To a solution of biladiene (6) (200 mg, 0.25 mmol) and methyl 2-formyl benzoate (847 mg, 5.16 mmol) in methanol (32 ml) was added 31% HBr (in acetic acid) (170 ml). The mixture was refluxed with stirring for 23 hours, cooled to the room temperature, poured into water (70 ml), basified with $NaHCO_3$ and extracted with methylene chloride (3×50 ml). The combined methylene chloride layer was washed with water (2×75 ml), dried ($Na_2SO_4$) and solvent removed. The residue was purified by flash column (silica; 7% acetone-hexane, then 3% acetone-methylene chloride) to get porphyrin (3), 87 mg (46%); $\lambda_{max}$ 406, 504, 537, 574, 626 nm; $^1$H NMR (300 MHz, CDCl$_3$) δ 10.12 (s, 2H, meso-H), 9.87 (s, 1H, meso-H), 8.4 (d, 1H, J=7.5 Hz, Ar—H), 8.29 (d, 1H, J=7.5 Hz, Ar—H), 7.92 (t, 1H, J=7.2 Hz, Ar—H), 7.81 (t, 1H, J=7.5 Hz, Ar—H), 4.39 (t, 4H, J=7.5 Hz, —$CH_2$—), 3.95 (m, 4H, —$CH_2$—), 3.66 (s, 9H, —$COOCH_3$), 3.64 (s, 6H, —$CH_3$), 3.28 (t, 4H, J=7.5 Hz, —$CH_2$—), 2.69 (m, 4H, —$CH_2$—), 1.83 (t, 6H, J=7 Hz, —$CH_3$), 1.05 (t, 6H, J=7 Hz, —$CH_3$).

Example 5

Synthesis of Naphthochlorin (8)

A solution of porphyrin (3) (84 mg, 0.11 mmol) in anhydrous THF (4 ml) was added (in drops) to a stirred slurry of LAH (28 mg, 0.73 mmol) in anhydrous THF (5 ml) at room temperature. Stirring was continued for 15 min. The excess LAH was decomposed by addition of 0.2N HCl in cold condition (ice-bath), diluted with water (15 ml) and extracted with methylene chloride (3×15 ml). The combined methylene chloride layer was washed with water (2×15 ml), dried ($Na_2SO_4$) and solvent removed to get the reduced product 4, 46 mg (62%), which was carried over directly to the next step.

A mixture of porphyrin (4) (46 mg, 0.06 mmol) and phosphoric acid (10 ml) was stirred and heated at 90° C. for 1.5 hour. After cooling to room temperature the mixture was poured into water (50 ml), basified with 20% aqueous NaOH and extracted with pyridine-methylene chloride mixture (40:60) (3×40 ml). The combined organic layer was washed with water (2×25 ml), dried ($Na_2SO_4$) and solvent removed. The residue was purified by flash column (silica; 3% methanol-methylene chloride) to get naphthochlorin (8), 20 mg (45%); $\lambda_{max}$ 428, 533, 569, 620, 676 nm; $^1$H NMR (300 MHz, DMSO-$d_6$) δ 9.26 (s, 1H, meso-H), 8.74 (s, 1H, Ar—H), 8.71 (d, 1H, J=7.5 Hz, Ar—H), 8.54 (s, 1H, meso-H), 8.44 (d, 1H, J=7.5 Hz, Ar—H), 8.23 (s, 1H, meso-H), 7.89 (t, 1H, J=8.1 Hz, Ar—H), 7.75 (t, 1H, J=7.2 Hz, Ar—H), 4.8 (t, 1H, J=5 Hz, —OH), 4.72 (t, 1H, J=5 Hz, —OH), 3.69-3.44 (m, 12H, —$CH_2$—), 2.53 (s, 6H, —$CH_3$), 2.14 (m, 8H, —$CH_2$—), 1.48 (t, 3H, J=6.9 Hz, —$CH_3$), 0.56 (t, 3H, J=7.2 Hz, —$CH_3$), 0.16 (t, 3H, J=2.5 Hz, —$CH_3$), 0.001 (t, 3H, J=2.5 Hz, —$CH_3$).

Example 6

Meso-(2'-methoxycarbonyl)phenyl octaethylporphyrin (9)

To a solution of octaethylbiladiene (500 mg) and methyl 2-formylbenzoate (1.8 g) in methanol (125 ml) was added 31% HBr (in acetic acid) (500 ml). The mixture was refluxed with stirring for 3 hrs, cooled to the room temperature, poured into water (200 ml), basified with $NaHCO_3$ and extracted with methylene chloride (3×100 ml). The combined methylene chloride layer was washed with water (2×100 ml), dried ($Na_2SO_4$) and solvent removed. The residue was purified by flash column (silica; 5% ethylacetate-methylene chloride) to get porphyrin (9), 400 mg; $\lambda_{max}$ 407, 505, 539, 575, 628 nm; $^1$H NMR (300 MHz), (CDCl$_3$) δ -2.98 (brs, 1H, NH), -2.79 (brs, 1H, NH), 1.17(t, 6H, CH$_3$), 1.93(t, 6H, CH$_3$), 1.99(t, 6H, CH$_3$), 2.00(t, 6H, CH$_3$), 2.66(s, 3H, CO$_2$CH$_3$), 2.84(om, 4H, CH$_2$), 4.0-4.3(om, 12H, CH$_2$), 7.89(st, 1H, Ar—H), 8.00(st, 1H, Ar—H), 8.38(d, 1H, Ar—H), 8.49(d, 1H, Ar—H), 9.99(s, 1H, meso-H), 10.22(s, 2H, meso-H). MS(FAB) m/z 677 (M+H$^+$).

Example 7

Octaethylnaphthachlorin (10)

A solution of porphyrin (9) (111 mg) in dichloromethane (25 ml) was added (in drops) to a solution of DIBAL in THF (2M, 5 ml) at room temperature. Stirring was continued for 50 min. The excess DIBAL was decomposed by dropwise addition of ethyl acetate (10 ml). Phosphoric acid (80%), (15 ml) was then added and the organic solvents removed by rotary evaporator. The phosphoric acid solution was heated at 100° C. for 2 hrs after which time water 50 ml was added. The solution was cooled to room temperature and the solid precipitate collected by filtration. The solid was dissolved in dichloromethane, three drops of triethylamine were added and the solution chromatographed on silica using 1% acetone/dichloromethane as eluent. The major green/grey fraction was collected and evaporated to dryness. The naphthochlorin could not be induced to crystallize satisfactorily. Yield=60 mg; $\lambda_{max}$ 427, 534, 568, 618, 675 nm; MS(FAB) m/z 611 (M+H$^+$), $^1$H NMR (300 MHz), (CDCl$_3$) δ 0.036 (t, 3H, sp$^3$CH$_3$), 0.28 (t, 3H, sp$^3$CH$_3$), 0.63 (t, 3H, CH$_3$), 1.51 (t, 3H, sp$^3$CH$_3$), 1.66 (ot, 12H, CH$_3$), 2.55-2.8 (om, 4H, CH$_2$), 3.28 (m, 1H, CH), 3.6 (om, 11H, CH$_2$), 7.69 (t, 1H, Ar—H), 7.80 (t, 1H, Ar—H), 8.01(s, 1H, meso-H), 8.26(s, 1H, meso-H), 8.30 (d, 1H, Ar—H), 8.61(s, 1H, meso-H), 8.86(d, 1H, arH), 9.28 (s, 1H, Ar—H).

Dipyrromethane (13)

A mixture of 3,4-diethylpyrrole-2-carboxylate (6.94 g, 35.6 mmol), 2-formyl-N,N-dimethylbenzaldehyde (7.62 g, 35.6 mmol) and p-toluene sulfonic acid (10.1 g, 53.4 mmol) was warmed at 70° C. with mixing. Methanol (20 ml) was added and warmed on a water bath (70° C.) to make a clear solution. Methanol was removed under reduced pressure (rotovap) and the mixture continued heating on the evaporator under vacuum until complete as detected by TLC (5% acetone/dichloromethane). Methanol (125 ml) was added and the solution poured into ice water, basified with sodium bicarbonate and extracted with dichloromethane. The combined dichloromethane layers were dried over sodium sulfate and rotoevaporated. The residue was chromatographed on silica using 5% acetone/dichloromethane as eluent and the major fraction collected. Yield=7.3 g (40.5%).

Dipyrromethane (14)

To dipyrromethane (13) (269 mg, 0.5 mmol) was added ethylene glycol (3 ml) and sodium hydroxide (130 mg, 3.2 mmol). The mixture was refluxed under argon for 1 hour and 20 minutes after which the reaction was cooled and poured into water and extracted with dichloromethane. The dichloromethane layer was dried over sodium sulfate, filtered and removed by rotary evaporation. The residue was chromatographed on silica (10% acetone-dichloromethane) to give the desired compound. After evaporation of the solvent and drying the yield was 160 mg (82%).

Dipyrromethane (15)

To a cooled (−10° C.) solution of dipyrromethane (14) (160 mg, 0.41 mmol) in dimethylformamide was added $POCl_3$ (180 mg, 115 uL, 1.23 mmol) in drops under an argon atmosphere. The reaction was stirred for 50 minutes and left to warm to room temperature over an hour. The reaction solution was poured into ice water and the solution was made alkaline using 20% aqueous sodium hydroxide. The product precipitated from the mixture and was filtered. The crude material was columned on silica using 10% acetone dichloromethane, to give the diformyldipyrromethane. Yield=142 mg (78%).

Porphyrin (17)

Methanol was added to 3,3'-di(2-methoxycarbonylethyl)-3,5-dimethylpyrromethane (16) (620 mg) and the diformyl dipyrromethane (15) (450 mg) was added. The solution was degassed with argon for 15 minutes and toluene sulfonic acid (456 mg) added. The solution was stirred for 3 hours at room temperature under argon and refrigerated overnight. DDQ (885 mg) was added and the solution stirred at room temperature for 30 minutes. The solution was poured into water, neutralized with $NaHCO_3$, and extracted with dichloromethane. The combined dichloromethane layers were dried over anhydrous sodium sulfate, filtered, and evaporated to dryness. The residue was dissolved in dichloromethane and chromatographed on silica using 10% acetone/dichloromethane as eluent. The major red fraction was collected and evaporated to dryness. Yield=411 mg.

Porphyrin (18)

To a solution of porphyrin (17)(210 mg, 0.27 mmol) in ethanol was added ethyl bromide (1 ml). The solution was refluxed for 2 hours, after which additional ethyl bromide (1 ml) was added. The solution was refluxed overnight, cooled to room temperature, and the solvent was removed. The residue was chromatographed on silica, eluting initially with 10% acetone/dichloromethane to remove unreacted starting material, followed by 10% methanol/dichloromethane to elute the quaternary compound (108 mg). The quaternary porphyrin was dissolved in acetic acid (3 ml) and sodium acetate (70 mg) added. The solution was refluxed for 24 hours then poured into ice water and neutralized with sodium acetate. The solution was extracted with dichloromethane and the organic layers combined and dried over sodium sulfate. The organic layer was filtered, and the solvent was removed to give the desired compound (78 mg).

Napthochlorin (19)

Porphyrin (18) (100 mg) was heated at 90-100° C. in phosphoric acid (5 ml) for 2 hours. The solution was cooled to room temperature and then poured into water (30 ml). The solid precipitate was collected by filtration, air dried overnight, and dissolved in 5% $MeOH/H_2SO_4$ (15 ml). The solution was stirred at room temperature until complete by TLC and poured into ice water and neutralized with sodium bicarbonate. The aqueous layer was extracted with dichloromethane and the organic layer evaporated to dryness. The residue was dissolved in dichloromethane and chromatographed on silica using 1% acetone/dichloromethane as eluent. The major green fraction was collected and crystalized from methanol/dichloromethane. Yield=55%.

Dipyrromethane (20)

A mixture of 3,4-diethylpyrrole-2-carboxylate (6.94 g, 35.6 mmol), p-anisaldehyde (2.45 g, 17.8 mmol), p-toluene sulfonic acid (10.1 g, 53.4 mmol) and methanol (300 ml) was refluxed under nitrogen. After all starting materials had been consumed as indicated by TLC ($CH_2Cl_2$) the solvent was removed by rotary evaporation, redissolved in dichloromethane, and washed with sodium bicarbonate solution and water. The organic layer was dried, filtered, and evaporated to dryness. The residue was dissolved in ethylene glycol (100 ml) and NaOH was added (10 g). The resulting solution was refluxed under argon for 2 hours after which a dark brown oil had separated. The solution was cooled to room temperature, diluted with water, and extracted with dichloromethane. The organic layer was dried, filtered, and rotoevaporated to dryness. The crude residue was dissolved in dichloromethane and chromatographed rapidly on silica using dichloromethane as eluent to give the desired compound as an oil after rotoevaporation. Yield=4.3 g. The compound was stored under argon in the refrigerator where after several weeks it slowly crystallized.

Napthochlorin (12)

A mixture of 3,3',4,4'-tetraethyldipyyromethane (6.0 g, 21.8 mmol), p-anisaldehyde (1.48 g, 11 mmol) and 2-carbomethoxybenzaldehyde (3.57 g, 21.8 mmol) in methanol (100 ml) was degassed by bubbling with argon for 20 minutes. Toluene sulfonic acid (4.8 g) was added and the solution stirred for 2 hours at room temperature and then refrigerated overnight. A solution of DDQ (4.0 g in methanol, 50 ml) was added and the solution stirred for a further 2 hours at room temperature. The solution was evaporated to dryness and redissolved in dichloromethane (200 ml). The organic layer was washed repeatedly with sodium bicarbonate solution and water and the organic layer evaporated to dryness. The residue was dissolved in dichloromethane (50 ml) and methanol (50 ml) was added. The dichloromethane was removed by rotary evaporation and the precipitated porphyrin collected by filtration. The crude porphyrin was chromatographed on silica, eluting initially with dichloromethane to elute the 5,15-bis(p-methoxyphenyl)porphyrin (250 mg), followed by 1% acetone/dichloromethane to elute the 5-(2'-carbomethoxyphenyl)-15-(p-methoxyphenyl)porphyrin (350 mg), followed by the 5,15-Bis(2'-carboxymethylphenyl)porphyrin (200 mg). The 5-(2'-carbomethoxyphenyl)-15-(p-methoxyphenyl)porphyrin was used directly.

To 5-(2'-carbomethoxyphenyl)-15-(p-methoxyphenyl) porphyrin (350 mg, 0.047 mmol) in dichloromethane (150 ml) cooled to 0° c. was added dropwise a solution of DibalH (20% wt, 0.1 mmol) and the solution stirred for 1 hour. The solution was left to warm to room temperature with stirring and ethylacetate (1 ml) was added. Phosphoric acid (10 ml) was added and the solvents removed by rotary evaporation. The phosphoric acid was heated at 110° C. for 3 hours after which time the solution was cooled to room temperature. A saturated solution of $NaHCO_3$ (10 ml) was added cautiously followed by water (50 ml). The solid precipitate was collected by filtration, air dried and columned on silica using 1% acetone dichloromethane as eluent. The major green fraction was collected and recrystallized from methanol/dichloromethane. Yield=205 mg.

It will be apparent to those skilled in the art that various modifications and variations can be made in the compounds and methods of the present invention without departing from the spirit or scope of the invention. Thus, it is intended that the present description cover the modifications and variations of this invention provided that they come within the scope of the appended claims and their equivalents.

What we claimed is:

1. A compound of formula IC:

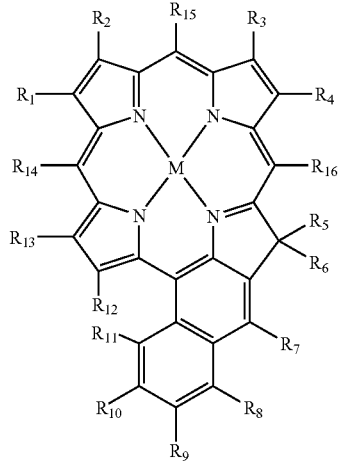

wherein:
$R_1$, $R_2$, $R_3$, $R_4$, $R_5$, $R_6$, $R_{12}$, $R_{13}$, $R_{14}$, $R_{15}$, and $R_{16}$ are independently selected from hydrogen, a halogen; unsubstituted or substituted alkyl, $C_3$-$C_6$ cycloalkyl, acetyl, aryl, alkenyl, alkynyl, amide groups, or ester groups; $NR_{17}R_{18}$; vinyl; $N(R_{17})(R_{18})(R_{19})^+Z^-$; $CH=CHNR_{17}R_{18}$; $CH_2CH_2NR_{17}R_{18}$; $CH=CHN(R_{17})(R_{18})(R_{19})^+Z^-$; $CH_2CH_2N(R_{17})(R_{18})(R_{19})^+Z^-$; $CHOHCH_3$; $CHOR_{17}CH_3$; CN; OH; $OR_{17}$; CHO; $CH=CHCO_2R_{17}$; $(CH_2)_nOH$; $(CH_2)_nSH$; $(CH_2)_nO$-alkoxy; $(CH_2)_nSR_{17}$; $(CH_2)_nOR_{17}$; $(CH_2)_nCO_2R_{17}$; $(CH_2)_nCONHR_{17}$; $(CH_2)_nCON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $SO_2N(R_{17})(R_{18})$; and $SO_2N(R_{17})(R_{18})(R_{19})^+Z^-$;

$R_{15}$ may be additionally selected from a cycloalkyl, aromatic, or hetereoaromatic fused ring system;

$R_{17}$, $R_{18}$, and $R_{19}$ are independently selected from hydrogen, a physiologically acceptable salt; and unsubstituted or substituted $C_1$-$C_6$ alkyl, aryl, alkenyl, or alkynyl;

$Z^-$ is a pharmaceutically acceptable ion;

$R_7$, $R_8$, $R_9$, $R_{10}$, and $R_{11}$ are independently selected from hydrogen, an unsubstituted or substituted alkyl or aryl;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr;

provided that when $R_1$, $R_2$, $R_3$, $R_4$, $R_5$, $R_6$, $R_8$, $R_{10}$, $R_{11}$, $R_{12}$, and $R_{13}$ are hydrogen, and $R_9$ is selected from the group consisting of hydrogen and $OCH_3$, and M is Ni, and $R_7$ is selected from the group consisting of $CH_3$, $CO_2tBu$, $CO_2Et$, $CO_2iPr$, and $CO_2Bu$, then $R_{14}$, $R_{15}$, and $R_{16}$ cannot simultaneously be $C_6H_4X$ where X is selected from the group consisting of hydrogen and $OCH_3$.

2. The compound according to claim 1 wherein:
$R_1$, $R_2$, $R_3$, $R_4$, $R_5$, $R_6$, $R_{12}$, and $R_{13}$ are independently selected from hydrogen, methyl, ethyl, $(CH_2)_nOH$, $(CH_2)_nO$-alkoxy, $(CH_2)_nOR_{17}$, $(CH_2)_nCO_2R_{17}$, $(CH_2)_nCONHR_{17}$, and $(CH_2)_nCON(R_{17})(R_{18})$;

$R_7$, $R_8$, $R_9$, $R_{10}$, and $R_{11}$ are independently selected from hydrogen, $SO_3H$, $SO_3R_{17}$, $SO_2NHR_{17}$, $SO_2N(R_{17})(R_{18})$, and $SO_2N(R_{17}(R_{18})(R_{19})^+Z^-$;

$R_{14}$, $R_{15}$, and $R_{16}$ are hydrogen; and

M is selected from two hydrogens and a metal ion selected from In, Pd, Pt, Sn, Zn, Ga, Al, and Mg.

3. A compound of formula ID:

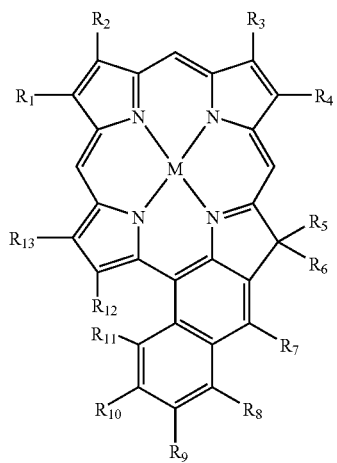

wherein:
$R_1$, $R_4$, $R_5$, $R_6$, $R_{12}$, and $R_{13}$ are independently selected from methyl and ethyl;

$R_7$, $R_8$, $R_9$, $R_{10}$, and $R_{11}$ are hydrogen, $R_2$ and $R_3$ are selected from methyl, ethyl, $(CH_2)_2OH$, $(CH_2)_2OMe$, $(CH_2)_3OH$, $(CH_2)_2CO_2Me$, $(CH_2)_2CO_2Na$, $(CH_2)_2CO_2K$ $(CH_2)_2CONHR_{17}$, $(CH_2)_2CON(R_{17})(R_{18})$, $(CH_2)_3OH$, $(CH_2)_3OMe$, $CH_2CO_2Me$, $CH_2CO_2Na$, and $CH_2CO_2K$;

where $R_{17}$ and $R_{18}$ are independently selected from $CH_3$, $CH_2CH_3$, $CH_2OCH_2OH$, $CH_2CH_2N(CH_3)_2$, and $CH_2CH_2$ (N $(CH_3)_3^+)S^=$, where $S^=$ is a physiologically acceptable ion; and M is selected from two hydrogens and a metal ion selected from In, Pd, Pt, Sn, Zn, Ga, Al, and Mg.

4. A compound of formula IE:

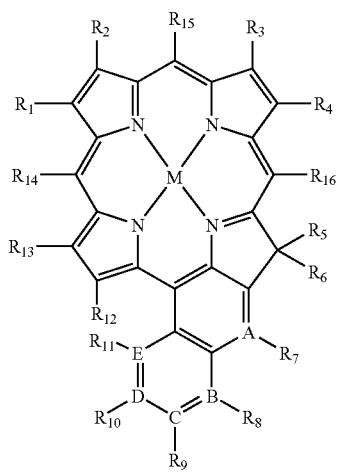

wherein:

$R_1$, $R_2$, $R_3$, $R_4$, $R_5$, $R_6$, $R_{12}$, $R_{13}$, $R_{14}$, $R_{15}$, and $R_{16}$ are independently selected from hydrogen, a halogen; unsubstituted or substituted alkyl, $C_3$-$C_6$ cycloalkyl, acetyl, aryl, alkenyl, alkynyl, amide groups, or ester groups; $NR_{17}R_{18}$; vinyl; $N(R_{17})(R_{18})(R_{19})^+Z^-$; $CH=CHNR_{17}R_{18}$; $CH_2CH_2NR_{17}R_{18}$; $CH=CHN(R_{17})(R_{18})(R_{19})+Z-$; $CH_2CH_2N(R_{17})(R_{18})(R_{19})^+Z^-$ $CHOHCH_3$; $CHOR_{17}CH_3$; CN; OH; $OR_{17}$; CHO; $CH=CHCO_2R_{17}$; $(CH_2)_nOH$; $(CH_2)_nSH$; $(CH_2)_nO$-alkoxy; $(CH_2)_nSR_{17}$; $(CH_2)_nOR_{17}$; $(CH_2)_nCO_2R_{17}$; $(CH_2)_nCONHR_{17}$; $(CH_2)CON(R_{17})(R_{18})$; $CO_2R_{17}$; $CONHR_{17}$; $CONR_{17}R_{18}$; $SR_{17}$; $SO_3H$; $SO_3R_{17}$; $SO_2NHR_{17}$; $_{SO2}N(R_{17})(R_{18})$; and $SO_2N(R_{17})(R_{18})(R_{19})^+Z^-$;

$R_{15}$ may be additionally selected from a cycloalkyl, aromatic, or heteroaromatic fused ring system;

$R_{17}$, $R_{18}$, and $R_{19}$ are independently selected from hydrogen, a physiologically acceptable salt; and unsubstituted or substituted $C_1$-$C_6$ alkyl, aryl, alkenyl, or alkynyl;

$Z^-$ is a pharmaceutically acceptable ion;

$R_7$, $R_8$, $R_9$, $R_{10}$, and $R_{11}$ are independently selected from hydrogen, an unsubstituted or substituted alkyl or aryl;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mg, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr;

A, B, C, D, and E are independently selected from carbon, nitrogen, sulfur, oxygen, $N+(R_{20})$ $Z^-$, Se+, and Te+; where $R_{20}$ is a functional group having a molecular weight of less than about 100,000 daltons and $Z'$ is a charge balancing ion;

provided that when $R_1$, $R_2$, $R_3$, $R_4$, $R_5$, $R_6$, $R_8$, $R_{10}$, $R_{11}$, $R_{12}$, and $R_{13}$ are hydrogen, and $R_9$ is selected from the group consisting of hydrogen and $OCH_3$, and A, B, C, D, and E are carbon, and M is Ni, and $R_7$ is selected from the group consisting of $CH_3$, $CO_2tBu$, $CO_2Et$, $CO_2iPr$, and $CO_2Bu$, then $R_{14}$, $R_{15}$, and $R_{16}$ cannot simultaneously be $C_6H_4X$ where X is selected from the group consisting of hydrogen and $OCH_3$.

5. The compound of claim 4 wherein:

$R_1$, $R_2$, $R_3$, $R_4$, $R_5$, $R_6$, $R_{12}$, and $R_{13}$ are independently selected from hydrogen, methyl, ethyl, $(CH_2)_nOH$, $(CH_2)_nO$-alkoxy, $(CH_2)_nOR_{17}$, $(CH_2)_nCO_2R_{17}$, $(CH_2)_nCONHR_{17}$, $(CH_2)_nCON(R_{17})(R_{18})$;

$R_7$, $R_8$, $R_9$, $R_{10}$, and $R_{11}$ are independently selected from hydrogen, an alkyl group, $SO_3H$, $SO_3R_{17}$, $SO_2NHR_{17}$, $SO_2N(R_{17})(R_{18})$, and $SO_2N(R_{17})(R_{18})(R_{19})^+Z'$;

$R_{14}$, $R_{15}$, and $R_{16}$ are hydrogen; and

M is selected from two hydrogens and a metal ion selected from In, Pd, Pt, Sn, Zn, Ga, Al, and Mg.

6. The compound of claim 5 wherein:

$R_1$ and $R_4$ are independently selected from methyl and ethyl;

$R_5$, $R_6$, $R_{12}$, and $R_{13}$, are independently selected from methyl and ethyl;

$R_7$, $R_{14}$, $R_{15}$, $R_{16}$ are hydrogen;

$R_2$ and $R_3$ are independently selected from $(CH_2)_2OH$, $(CH_2)_2OMe$, $(CH_2)_3OH$, $(CH_2)_3OMe$, $(CH_2)_2CO_2Me$, $(CH_2)_2CO_2Na$, $(CH_2)_2CO_2K$ $(CH_2)_2CONHR_{17}$, $(CH_2)_2CON(R_{17})(R_{18})$, $(CH_2)_3OH$, $CH_2CO_2Me$, $CH_2CO_2Na$, and $CH_2CO_2K$;

$R_{17}$ and $R_{18}$ are independently selected from $CH_3$, $CH_2CH_3$, $CH_2OCH_2OH$, $CH_2CH_2N(CH_3)_2$, and $CH_2CH_2(N(CH_3)_3^+)S^-$, where $S^-$ is a physiologically acceptable ion; and M is selected from two hydrogens and a metal ion selected from In, Pd, Pt, Sn, Zn, Ga, Al and Mg.

* * * * *